(12) United States Patent
Nishio et al.

(10) Patent No.: US 10,011,643 B2
(45) Date of Patent: Jul. 3, 2018

(54) FREEZE-DRIED PREPARATION CONTAINING HIGH-PURITY PTH AND METHOD FOR PRODUCING SAME

(71) Applicant: ASAHI KASEI PHARMA CORPORATION, Tokyo (JP)

(72) Inventors: Fumihide Nishio, Tokyo (JP); Takuji Maejima, Tokyo (JP); Yoshiro Mitome, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

(21) Appl. No.: 14/990,948

(22) Filed: Jan. 8, 2016

(65) Prior Publication Data

US 2016/0145316 A1    May 26, 2016

Related U.S. Application Data

(62) Division of application No. 14/116,483, filed as application No. PCT/JP2012/064229 on May 31, 2012, now abandoned.

(30) Foreign Application Priority Data

Jun. 7, 2011    (JP) ................................ 2011-127698

(51) Int. Cl.
| | |
|---|---|
| *A61K 38/22* | (2006.01) |
| *A61K 9/19* | (2006.01) |
| *C07K 14/635* | (2006.01) |
| *F26B 5/06* | (2006.01) |
| *G01N 30/88* | (2006.01) |
| *G01N 33/68* | (2006.01) |
| *A61K 38/29* | (2006.01) |
| *B65B 55/10* | (2006.01) |
| *B65B 55/12* | (2006.01) |
| *B65B 63/08* | (2006.01) |
| *G01N 30/72* | (2006.01) |

(52) U.S. Cl.
CPC .............. *C07K 14/635* (2013.01); *A61K 9/19* (2013.01); *A61K 38/29* (2013.01); *B65B 55/10* (2013.01); *B65B 55/12* (2013.01); *B65B 63/08* (2013.01); *G01N 30/7233* (2013.01)

(58) Field of Classification Search
None
See application file for complete search history.

(56) References Cited

U.S. PATENT DOCUMENTS

| 3,769,717 A | 11/1973 | Lorentzen et al. |
| 5,059,587 A | 10/1991 | Yamamoto et al. |
| 5,208,041 A | 5/1993 | Sindrey |
| 5,496,801 A | 3/1996 | Holthuis et al. |
| 5,563,122 A | 10/1996 | Endo et al. |
| 2002/0110871 A1 | 8/2002 | Zahradnik et al. |
| 2005/0107292 A1 | 5/2005 | Minamitake et al. |
| 2005/0209144 A1 | 9/2005 | Billger et al. |
| 2005/0256045 A1 | 11/2005 | Mahmoud et al. |
| 2006/0247181 A1 | 11/2006 | Fawzi |
| 2010/0242300 A1 | 9/2010 | Debo et al. |
| 2011/0034399 A1 | 2/2011 | Nourrisson |

FOREIGN PATENT DOCUMENTS

| AU | 1604992 B | 8/1993 |
| CA | 2052375 C | 3/1992 |
| CN | 1142772 A | 2/1997 |
| CN | 1440294 A | 9/2003 |
| CN | 1861790 A | 11/2006 |
| CN | 101535690 A | 9/2009 |
| EP | 302772 A1 | 2/1989 |
| EP | 515228 A2 | 11/1992 |
| EP | 619119 A1 | 10/1994 |
| EP | 1297842 A1 | 4/2003 |
| GB | 1370683 A | 10/1974 |
| JP | 5568572 | 5/1980 |
| JP | 55112980 | 9/1980 |
| JP | S62-67099 A | 3/1987 |
| JP | 6360940 | 3/1988 |
| JP | 6416799 | 1/1989 |
| JP | H02111 | 1/1990 |
| JP | H05306235 | 11/1993 |
| JP | 873376 A | 3/1996 |

(Continued)

OTHER PUBLICATIONS

Office Action dated May 10, 2016 in Chinese Application No. 201510024087.0.
Wu Songtao et al., The effects of PTH(1-34) on osseointegration of dental implant in osteoporosis rabbits, J Pract Stomatol, Mar. 31, 2011, pp. 181-184.
Office Action dated Sep. 7, 2016 in Japanese Application No. 2016-124400.
Notice of Grounds for Rejection as issued in Japanese Patent Application No. 2015-008625, dated Jun. 7, 2016.
"Guidance on the Manufacture of Sterile Pharmaceutical Products by Aseptic Processing," Ministry of Health, Labor and Welfare, Pharmaceutical and Food Safety Bureau, Compliance and Narcotics Division, Apr. 20, 2011, pp. 1-86, URL, <https://www.pmda.go.jp/files/000206144.pdf>.
Eyanagi, S., "Newest Trend of Sterilization System: A Case of the Decontamination Technology for Clean Room of of Pharmaceutical Manufacturing Factory with Peracetic Acid Disinfectant," Pharm Tech Japan, 2010, 26(10), 51-56.

(Continued)

*Primary Examiner* — Julie Ha
*Assistant Examiner* — Kristina M Hellman
(74) *Attorney, Agent, or Firm* — Pillsbury Winthrop Shaw Pittman, LLP

(57) ABSTRACT

[Problem] Provided is a freeze-dried preparation containing high-purity PTH peptide and a method for the production thereof. Also provided is a test method for PTH analogs to confirm the purity of a freeze-dried preparation containing PTH peptide, and the like.
[Solution] In the present invention, the presence of PTH analogs produced during the manufacturing process of a freeze-dried preparation containing PTH peptide was confirmed. The production of these PTH analogs was also discovered to be markedly prevented or reduced by controlling exposure of the solution containing PTH peptide and the like to air environments within a pharmaceutical production facility.

31 Claims, 16 Drawing Sheets

(56) References Cited

FOREIGN PATENT DOCUMENTS

| | | |
|---|---|---|
| JP | 9-506869 | 7/1997 |
| JP | 2002-512973 | 5/2002 |
| JP | 200395974 | 4/2003 |
| JP | 2008-533146 A | 8/2008 |
| JP | 2010-509563 | 3/2010 |
| JP | 2010216664 | 9/2010 |
| KR | 2003-0016315 | 2/2003 |
| WO | 9311247 A1 | 6/1993 |
| WO | 9517207 | 6/1995 |
| WO | PCT/EP1996/004503 | 10/1996 |
| WO | 200010596 | 3/2000 |
| WO | 200202136 | 1/2001 |
| WO | 0121198 A1 | 3/2001 |
| WO | 132144 A1 | 5/2001 |
| WO | 2007095288 | 8/2007 |
| WO | 2007147902 A2 | 12/2007 |
| WO | 2008063279 | 5/2008 |
| WO | 2010030670 | 3/2010 |

OTHER PUBLICATIONS

Eidai, N., et al., "Newest Trend of Sterilization System III: Practice by ozone fumigation sterilization of the clean room for production of sterile pharmaceuticals; Use of ozone gas as the substitute agent to the conventional formaldehyde," Pharm Tech Japan, 2010, 26(11), 95-103.
Office Action dated Nov. 4, 2016 in Japanese Application 2016-183055.
European Office Action dated Mar. 29, 2017 for Appln. No, 16199737.4.
Extended European Search Report dated Apr. 15, 2016 issued in European Application 15181579.2.
Shoyele, Sunday A. et al., The Effects of Excipients and Particle Engineering on the Biophysical Stability and Aerosol Performance of Parathyroid Hormone (1-34) Prepared as a Dry Powder for Inhalation, AAPS Pharmscitech, Springer New York LLC, US, vol. 12, No. 1, Mar. 2011, p. 304-311.
Office Action dated Mar. 7, 2016 in Japanese Patent Application 2013-519467.
Office Action dated Mar. 8, 2016 in Japanese Patent Application 2015-008625.
Office Action dated Dec. 2, 2015 in Korean Patent Application 10-2013-7030871.
Office Action dated Dec. 2, 2015 in Korean Patent Application 10-2015-7026789.
Office Action dated Dec. 2, 2015 in Korean Patent Application 10-2015-7026794.
"Akers, ""Sterile Drug Products: Formulation, Packaging, Manufacturing, and Quality""", Chpt. 13, Contamination control, pp. 194-210 (2010), published by Informa Healthcare."
Chinese Office Action issued with respect to Application No. 201280026213.0, dated Jul. 3, 2014.
International Search Report issued for PCT/JP2012/064229, dated Aug. 7, 2012.
Japanese Office Action issued with respect to Application No. 2013-519467, dated Nov. 18, 2014.
Ji et al., Journal of Pharmaceutical Sciences, 2009, vol. 98, No. 12, pp. 4485-4500.
Kadowaki and Kobayashi, PharmaTech Japan, 1993, vol. 9, No. 2, pp. 39 (183)-43 (187).
Kiso et al., "Opiod Activities of Enkephalin Analogs," from Peptide Chemistry 1980, 1981, pp. 187-192.
Merrifield, from Advances in Enzymology, "Solid-Phase Peptide Synthesis," 1969, vol. 32, pp. 221-296.
Miller, "Safety of Parathyroid Hormone for the Treatment of Osteoporosis", 2008, vol. 6, pp. 12-16.
Office Action dated May 19, 2015 in Chinese Application No. 201280026213.0.
Sung et al., J. Bioi. Chem, 1991, vol. 266, pp. 2831-2835.
Supplemental European Search Report dated Mar. 9, 2015 issued in EP Application No. 12796142.3.
Office Action dated Nov. 17, 2015 in Japanese Application No. 2015-179919.
Proos, Elizabeth et al., "Long-term stability and in vitro release of hPTH(1-34) from a multi-reservoir array", MicroCHIPS, Inc., Bedford, Massachusetts 01730, USA, Pharmaceutical Research, vol. 25, No. 6, Jun. 2008, pp. 1387-1395. DOI: 10.1007/s11095-008-9544-0.
Office Action dated Sep. 21, 2016 in Japanese Application No. 2016-124401.
Korean Office Action dated Mar. 2, 2017 for Appln. No. 10-2013-7030871-.
Korean Office Action dated Mar. 2, 2017 for Appln. No. 10-2015-7026789.
Korean Office Action dated Mar. 2, 2017 for Appln. No. 10-2015-7026794.
Korean Office Action dated Mar. 2, 2017 for Appln. No. 10-2016-7014677.
Submission of Observations by Third Party on Documents and the Like dated Aug. 18, 2016 in Japanese Application No. 2013-519467.
Request for Inspection of File Record submitted Aug. 29, 2016 in Japanese Application No. 2013-519467.
Exhibit 3, Medical Use Medicament Leaflet, Teriparatide Acetate for Intravenous Injection 100, "Asahi Kasei"; URL http://www.pmda.go.jp/PmdaSearch/iyakuDetail/ResultDataSetPDF/100968_7223403D1045_1_02, Jun. 2008.
Exhibit 4, YMC-Pack Protein-RP Product Information; URL http://www.ymc.co.jp/columns/ymc_pack_protein_rp/, downloaded Jul. 28, 2016.
Document Describing "Reasons for the Submission" , Aug. 18, 2016.
C. G. Dacke et al., Effects of Synthetic Bovine Parathyroid Hormone (1-34) and its Analogues on 45Ca Uptake and Andenylate Cyclase Activation in Bone and Plasma Calcium Levels in the Chick, Quarterly Journal of Experimental Physiology (1988), Great Britain, vol. 73, pp. 573-584.
David Goltzmann et al., Analysis of the Requirements for Parathyroid Hormone Action in Renal Membranes with the Use of Inhibiting Analogues, The Journal of Biological Chemistry, vol. 250, No. 8, Issue of Apr. 25, 1975, pp. 3199-3203.
Office Action dated Apr. 11, 2017 in Chinese Application 201510024087.0.
Office Action dated Feb. 8, 2017 in European Application 12796142.3.
Communication pursuant to Article 94(3) EPC, EP Application No. 15181579.2 dated Nov. 14, 2017.
Notice of Grounds for Rejection Japanese Patent Application No. 2016-183054 dated May 24, 2017 with English translation.
Notice of Grounds for Rejection Japanese Patent Application No. 2016-183054 dated Sep. 4, 2017 with English translation.
Decision of Patent Rejection Korean Patent Application No. 10-2016-7014677 dated Jan. 29, 2018 with English translation.
Third Notification of Office Action Chinese Patent Application No. 201510024087.0 dated Nov. 15, 2017 with English translation.

[Figure 16]
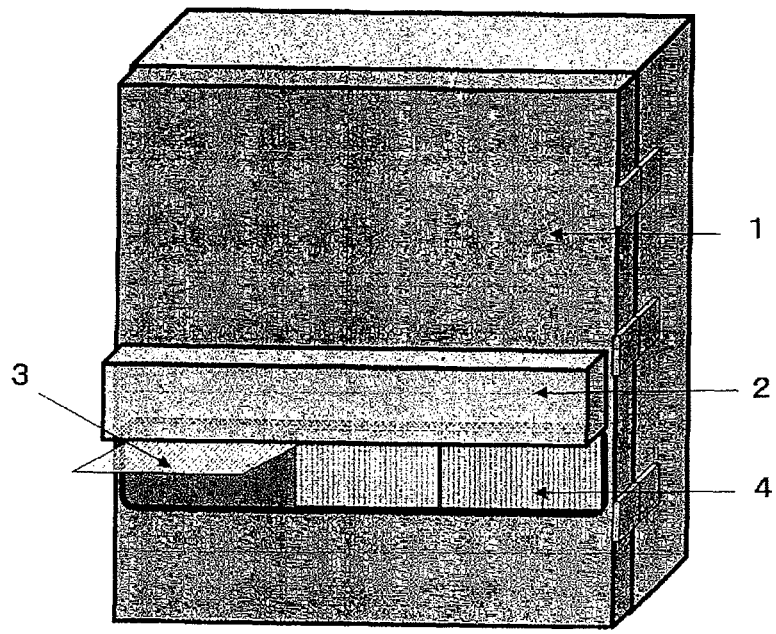
[Figure 17]
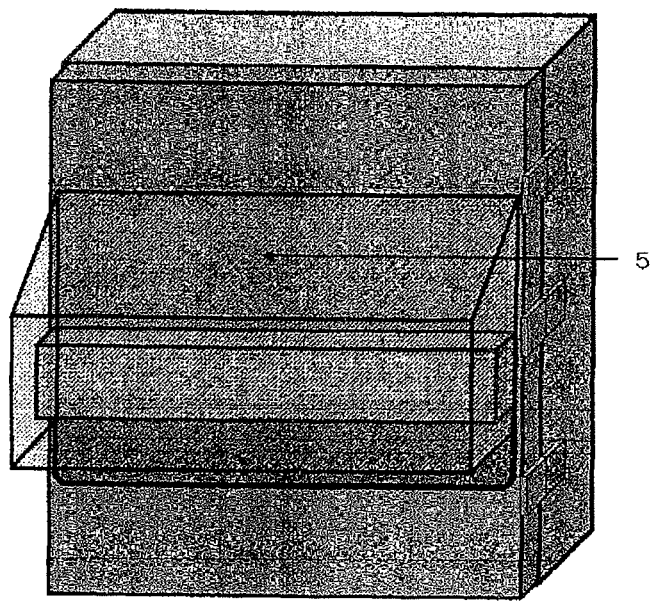

```
                         SEQUENCE LISTING

<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Trypsin-digested fragment of hPTH(1-34)

<400> SEQUENCE: 1

Ser Val Ser Glu Ile Gln Leu Met His Asn Leu Gly Lys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Trypsin-digested fragment of hPTH(1-34)

<400> SEQUENCE: 2

His Leu Asn Ser Met Glu Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Trypsin-digested fragment of hPTH(1-34)

<400> SEQUENCE: 3

Val Glu Trp Leu Arg
1               5

<210> SEQ ID NO 4
<211> LENGTH: 34
<212> TYPE: PRT
<213> ORGANISM: Artificial Sequence
<220> FEATURE:
<223> OTHER INFORMATION: hPTH(1-34)

<400> SEQUENCE: 4

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 5
<211> LENGTH: 7
<212> TYPE: PRT
```

```
<213> ORGANISM: Artificial Sequence
<220> FEATURE:
<223> OTHER INFORMATION: Trypsin-digested fragment of hPTH(1-34)

<400> SEQUENCE: 5

Leu Gln Asp Val His Asn Phe
1               5
```

FREEZE-DRIED PREPARATION CONTAINING HIGH-PURITY PTH AND METHOD FOR PRODUCING SAME

CROSS REFERENCE TO RELATED APPLICATION

This application is a divisional of U.S. application Ser. No. 14/116,483, filed Nov. 8, 2013, which is the U.S. National Stage under 35 USC § 371 of International Application No. PCT/JP2012/064229, filed on May 31, 2012, entitled "FREEZE-DRIED PREPARATION CONTAINING HIGH-PURITY PTH AND METHOD FOR PRODUCING SAME", which claims priority to JP 2011-127698, filed Jun. 7, 2011. Each hereby expressly incorporated by reference in its entirety.

TECHNICAL FIELD

The present invention relates to a freeze-dried preparation containing PTH (parathyroid hormone) or a substance of equivalent physiologic activity (collectively referred to hereinafter as "PTH peptide") as an active ingredient. The present invention also relates to a method for producing a freeze-dried preparation containing PTH peptide. The present invention also relates to a method for testing and assuring the quality of freeze-dried preparations containing PTH peptide.

BACKGROUND ART

Parathyroid hormone, together with calcitonins and vitamin Ds, is a hormone that participates in regulating the calcium concentration in the blood. Therefore, PTH peptide is used as a diagnostic for hypoparathyroidism. Parathyroid hormone is also known to accelerate the absorption of calcium in the intestine by increasing active vitamin D3 production in the kidneys (Non-patent Reference 1). A method of treating osteoporosis that increases the density of cancellous bone and does not decrease the density of the cortical bone of osteoporosis patients by subcutaneous administration of 100 or 200 units/time of PTH once a week over a period of 26 weeks to osteoporosis patients has also been disclosed (Patent Reference 7).

A method of combining mannitol or another such saccharide or gelatin or another such macromolecular substance as a stabilizer is generally used when making a trace of PTH peptide into a freeze-dried preparation to be dissolved at the time of use (Patent References 1 and 2). A freeze-dried pharmaceutical composition characterized in containing a monosaccharide or disaccharide and sodium chloride is also known (Patent Reference 3).

When a freeze-dried preparation such as the above is manufactured aseptically to produce a pharmaceutical, ordinary pharmaceutical production facilities utilize areas that achieve a sterile environment by a stream of aseptic air of a constant speed that has passed through HEPA filters. A manufacturing process in a pharmaceutical production facility under this sterile environment typically consists of a step for preparing an active ingredient solution, followed by a step for aseptically filtering of the solution and dispensing it into containers, a step for loading the filled containers into a freeze-drying chamber, and a step for sealing the containers (vials and the like) after the freeze-drying step.

PRIOR ART REFERENCES

Patent References

Patent Reference 1: JP Kokai 63-60940
Patent Reference 2: JP Kokai 2-111
Patent Reference 3: JP Kokai 5-306235
Patent Reference 4: JP Kokai 64-16799
Patent Reference 5: WO02/002136
Patent Reference 6: JP Kokai 2003-095974
Patent Reference 7: JP Kokai 8-73376
Patent Reference 8: WO00/10596
Patent Reference 9: WO10/30670

Non-Patent References

Non-Patent Reference 1: Current Osteoporosis Reports, Vol. 6, 12-16, 2008
Non-Patent Reference 2: Journal of pharmaceutical sciences, vol. 98, no. 12, p 4485-4500, 2009
Non-Patent Reference 3: ADVANCES IN ENZYMOLOGY, 32, 221-296, 1969
Non-Patent Reference 4: J. Biol. Chem., vol. 266, 2831-2835, 1991
Non-Patent Reference 5: M. Takei et al., Peptide Chemistry 1980, 187-192, 1981

SUMMARY OF INVENTION

Problems to be Solved by the Invention

The active ingredient of a pharmaceutical is obtained by chemical synthesis from raw materials, by isolation and refining of a biological product, by production by genetic engineering and isolation and refining of the product, and the like. It is generally difficult to obtain 100% purity of the pharmaceutical active ingredient produced due to the purity of the raw materials themselves, incomplete reactions, decomposition during isolation and refining, and other such factors, in any method, including genetic recombination. On the other hand, since the possibility of undesirable effects on diagnosis and treatment cannot be ruled out when diagnostic and therapeutic drugs contain more than the acceptable amount of impurities, the fact remains that obtaining a high-purity product is an important factor for producing a safe, effective drug. When preparations containing PTH peptide are used in the treatment/prevention of osteoporosis in particular, high purity can be said to be especially necessary for preparations containing PTH peptide because the duration of administration extends over a long period of time.

However, it was found that, when the freeze-dried preparation containing PTH peptide of the present invention is manufactured on an industrial scale by a typical production process such as the above, a preparation containing substances in which the chemical structure of the active ingredient (PTH peptide) has been changed (referred to hereinafter as "PTH analogs") is produced. Especially as the production scale increases, the problem faced is that there is concern that the amount of PTH analogs produced will rise to an essentially unacceptable level as the production volume increases. Furthermore, the amount of PTH analogs produced is not always constant but changes depending the production time and place, on differences in time, and the like. Since the factors that lead to the production of these PTH analogs had not been specified, a serious problem faced in practice was also that the amounts produced could not be controlled.

The purpose of the present invention is to provide a freeze-dried preparation containing PTH peptide of high purity, that is, in which the content of PTH analogs is kept to an acceptably low level. Another purpose of the present invention is to provide a method for producing this high-purity freeze-dried preparation containing PTH peptide. Yet another purpose of the present invention is to provide a test method for PTH analogs for purposes such as checking the purity of a freeze-dried preparation containing PTH peptide.

Means Used to Solve the Above-Mentioned Problems

The present inventors were concerned that the amount of PTH analogs produced would rise to an essentially unacceptable level as the production scale increased and the production volume rose and succeeded in isolating and characterizing these PTH analogs. They also discovered that controlling the exposure of solution containing PTH peptide and the like to air environments within a pharmaceutical production facility greatly inhibits and decreases the production of these PTH analogs.

While not being bound by the theory, it was assumed that, given the structural characteristics of the PTH analogs characterized as mentioned above and the fact that the production of these analogs is inhibited and decreased by controlling exposure to air environments within a pharmaceutical production facility, the cause of the production of these PTH analogs is substances having oxidizing capability present in air environments within a pharmaceutical production facility. Certainly, aside from those of high cleanliness (grade A and the like), air environments in pharmaceutical production facilities often can contain gaseous substances having oxidizing capability. Namely, pharmaceutical production facilities are fumigated and disinfected by formaldehyde, ozone, and other such sterilizing agents to more fully actualize an aseptic environment. One can therefore also come to think that gases having oxidizing capability such as formaldehyde and ozone can be contained as residues of this fumigation and disinfection. For that matter, ozone is present in a concentration of 0.001-0.02 ppm, approximately 0.02-0.1 ppm depending on the time, location, and season, in the atmosphere regardless of fumigation and disinfection.

The present inventors also confirmed that the production of the PTH analogs elucidated by the present invention can be reproduced by bringing PTH peptide into contact with air containing ozone.

The present invention therefore encompasses the following aspects and preferred embodiments.

[1] A freeze-dried preparation containing high-purity PTH peptide as an active ingredient, wherein "high-purity" means at least that the amount of at least one PTH analog versus the sum of the amount of PTH peptide and the total amount of PTH analogs in the preparation is 1.0% or less and/or that the total amount of PTH analogs versus the sum of the amount of PTH peptide and the total amount of PTH analogs is 5.0% or less; the freeze-dried preparation containing PTH peptide being produced by a method characterized in that the exposure of the solution containing PTH peptide prior to freeze drying to air environments within a pharmaceutical production facility is controlled.

[2] A freeze-dried preparation containing PTH peptide set forth in [1] wherein the PTH analog is at least one or more among 1) analog 1:

oxide of PTH peptide having a mass number 64 Da larger than the mass number of the PTH peptide contained in the preparation and producing digestion products corresponding to the following fragments (1-a) to (1-c) when the analog is digested by trypsin, (1-a) Mass number of Ser-Val-Ser-Glu-Ile-Gln-Leu-Met-His-Asn-Leu-Gly-Lys (SEQ ID NO: 1) +16 Da, (1-b) Mass number of His-Leu-Asn-Ser-Met-Glu-Arg (SEQ ID NO: 2) +16 Da, and (1-c) Mass number of Val-Glu-Trp-Leu-Arg (SEQ ID NO: 3) +4 Da;

2) analog 2:

oxide of PTH peptide having a mass number 36 Da larger than the mass number of the PTH peptide contained in the preparation and producing digestion products corresponding to the following fragments (2-a) to (2-c) when the analog is digested by trypsin, (2-a) Mass number of Ser-Val-Ser-Glu-Ile-Gln-Leu-Met-His-Asn-Leu-Gly-Lys (SEQ ID NO: 1) +16 Da, (2-b) Mass number of His-Leu-Asn-Ser-Met-Glu-Arg (SEQ ID NO: 2) +16 Da, and (2-c) Mass number of Val-Glu-Trp-Leu-Arg (SEQ ID NO: 3) +4 Da;

3) analog 3:

oxide of PTH peptide having a mass number 32 Da larger than the mass number of the PTH peptide contained in the preparation and producing digestion products corresponding to the following fragments (3-a) and (3-b) when the analog is digested by trypsin, (3-a) Mass number of Ser-Val-Ser-Glu-Ile-Gln-Leu-Met-His-Asn-Leu-Gly-Lys (SEQ ID NO: 1) +16 Da, (3-b) Mass number of His-Leu-Asn-Ser-Met-Glu-Arg (SEQ ID NO: 2) +16 Da;

4) analog 4:

oxide of PTH peptide having a mass number 48 Da larger than the mass number of the PTH peptide contained in the preparation and producing digestion products corresponding to the following fragments (4-a) and (4-b) when the analog is digested by trypsin, (4-a) Mass number of Ser-Val-Ser-Glu-Ile-Gln-Leu-Met-His-Asn-Leu-Gly-Lys (SEQ ID NO: 1) +16 Da, (4-b) Mass number of Val-Glu-Trp-Leu-Arg (SEQ ID NO: 3) +4 Da;

5) analog 5:

oxide of PTH peptide having a mass number 48 Da larger than the mass number of the PTH peptide contained in the preparation and producing digestion products corresponding to the following fragments (5-a) and (5-b) when the analog is digested by trypsin, (5-a) Mass number of His-Leu-Asn-Ser-Met-Glu-Arg (SEQ ID NO: 2) +16 Da, and (5-b) Mass number of Val-Glu-Trp-Leu-Arg (SEQ ID NO: 3) +4 Da;

6) analog 6:

oxide of PTH peptide having a mass number 20 Da larger than the mass number of the PTH peptide contained in the preparation and producing digestion products corresponding to the following fragments (6-a) and (6-b) when the analog is digested by trypsin, (6-a) Mass number of His-Leu-Asn-Ser-Met-Glu-Arg (SEQ ID NO: 2) +16 Da, and
(6-b) Mass number of Val-Glu-Trp-Leu-Arg (SEQ ID NO: 3) +4 Da;
7) analog 7:
oxide of PTH peptide having a mass number 16 Da larger than the mass number of the PTH peptide contained in the preparation and producing a digestion product corresponding to the following fragment (7-a) when the analog is digested by trypsin,
(7-a) Mass number of Ser-Val-Ser-Glu-Ile-Gln-Leu-Met-His-Asn-Leu-Gly-Lys (SEQ ID NO: 1) +16 Da;
8) analog 8:
oxide of PTH peptide having a mass number 16 Da larger than the mass number of the PTH peptide contained in the preparation and producing a digestion product corresponding to the following fragment (8-a) when the analog is digested by trypsin,
(8-a) Mass number of His-Leu-Asn-Ser-Met-Glu-Arg (SEQ ID NO: 2) +16 Da;
9) analog 9:
oxide of PTH peptide having a mass number 32 Da larger than the mass number of the PTH peptide contained in the preparation and producing a digestion product corresponding to the following fragment (9-a) when the analog is digested by trypsin,
(9-a) Mass number of Val-Glu-Trp-Leu-Arg (SEQ ID NO: 3) +4 Da;
10) analog 10:
oxide of PTH peptide having a mass number 16 Da larger than the mass number of the PTH peptide contained in the preparation and producing a digestion product corresponding to the following fragment (10-a) when the analog is digested by trypsin,
(10-a) Mass number of Val-Glu-Trp-Leu-Arg (SEQ ID NO: 3) +16 Da; or
11) analog 11:
oxide of PTH peptide having a mass number 4 Da larger than the mass number of the PTH peptide contained in the preparation and producing a digestion product corresponding to the following fragment (11-a) when the analog is digested by trypsin,
(11-a) Mass number of Val-Glu-Trp-Leu-Arg (SEQ ID NO: 3) +4 Da.

[3] A freeze-dried preparation containing PTH peptide set forth in [1] wherein the PTH analog is at least one or more among 1) analog 1':
oxide of PTH peptide in which residues corresponding to the position 8 and position 18 methionine of human PTH (1-34) have been changed into methionine sulfoxide residues and the residue corresponding to the position 23 tryptophan has been changed into a residue shown by the following structural formula (a);

[Chemical Formula 1]

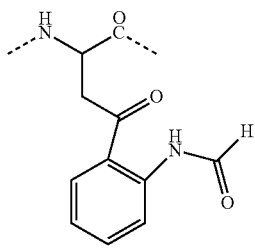

(a)

2) analog 2':
oxide of PTH peptide in which residues corresponding to the position 8 and position 18 methionine of human PTH (1-34) have been changed into methionine sulfoxide residues and the residue corresponding to the position 23 tryptophan has been changed into a residue shown by the following structural formula (b);

[Chemical Formula 2]

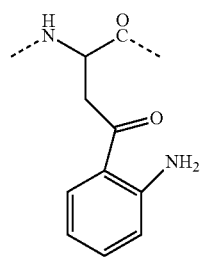

(b)

3) analog 3':
oxide of PTH peptide in which residues corresponding to the position 8 and position 18 methionine of human PTH (1-34) have been changed into methionine sulfoxide residues;
4) analog 4':
oxide of PTH peptide in which the residue corresponding to the position 8 methionine of human PTH (1-34) has been changed into a methionine sulfoxide residue and the residue corresponding to the position 23 tryptophan has been changed into a residue shown by the above structural formula (a);
5) analog 5':
oxide of PTH peptide in which the residue corresponding to the position 18 methionine of human PTH (1-34) has been changed into a methionine sulfoxide residue and the residue corresponding to the position 23 tryptophan has been changed into a residue shown by the above structural formula (a);
6) analog 6':
oxide of PTH peptide in which the residue corresponding to the position 18 methionine of human PTH (1-34) has been changed into a methionine sulfoxide residue and the residue corresponding to the position 23 tryptophan has been changed into a residue shown by the above structural formula (b);
7) analog 7':
oxide of PTH peptide in which the residue corresponding to the position 8 methionine of human PTH (1-34) has been changed into a methionine sulfoxide residue;
8) analog 8':
oxide of PTH peptide in which the residue corresponding to the position 18 methionine of human PTH (1-34) has been changed into a methionine sulfoxide residue;
9) analog 9':
oxide of PTH peptide in which the residue corresponding to the position 23 tryptophan of human PTH (1-34) has been changed into a residue shown by the above structural formula (a);
10) analog 10':
oxide of PTH peptide in which the residue corresponding to the position 23 tryptophan of human PTH (1-34) has been changed into a tryptophan monoxide residue shown by the following structural formula (c-1) or (c-2);

[Chemical Formula 3]

(c)-1

(c)-2

Or 11) analog 11':
oxide of PTH peptide in which the residue corresponding to the position 23 tryptophan of human PTH (1-34) has been changed into a residue shown by the above structural formula (b).

[4] The freeze-dried preparation containing PTH peptide set forth in [2] wherein high-purity means that the amount of at least one of the above analogs 1 to 11 versus the sum of the amount of PTH peptide and the total amount of PTH analogs in the preparation is 1.0% or less and/or that the total amount of the above analogs 1 to 11 versus the sum of the amount of PTH peptide and the total amount of PTH analogs is 5.0% or less.

[5] The freeze-dried preparation containing PTH peptide set forth in [3] wherein high-purity means that the amount of at least one of the above analogs 1' to 11' versus the sum of the amount of PTH peptide and the total amount of PTH analogs in the preparation is 1.0% or less and/or that the total amount of the above analogs 1' to 11' versus the sum of the amount of PTH peptide and the total amount of PTH analogs is 5.0% or less.

[6] The freeze-dried preparation containing PTH peptide according to any of [1] to [5] wherein the PTH peptide is human PTH (1-34).

[7] The freeze-dried preparation containing PTH peptide according to any of [1] to [6] wherein the freeze-dried preparation containing PTH peptide is housed in a glass vial.

[8] The freeze-dried preparation containing PTH peptide according to any of [1] to [7], characterized in that exposure of the solution containing PTH peptide to air environments within a pharmaceutical production facility prior to freeze drying is controlled in any one or more steps selected from a step for preparing a solution containing PTH peptide, an aseptic filtration step, a drug solution dispensing step, and a step for loading into a freeze drying means.

[9] The freeze-dried preparation containing PTH peptide set forth in [8] characterized in being produced using a method that also includes control of exposure of the freeze-dried product to air environments within a pharmaceutical production facility in a vial sealing step after freeze drying.

[10] The freeze-dried preparation containing PTH peptide according to any of [1] to [9] characterized in that exposure of the solution containing PTH peptide to air environments within a pharmaceutical production facility prior to freeze drying is controlled in the step for loading into the freeze drying means.

[11] The freeze-dried preparation containing PTH peptide set forth in [10] characterized in that the above exposure is controlled by using a freeze-drying chamber equipped with a means for controlling the entrance of air within a pharmaceutical production facility into the freeze-drying means.

[12] The freeze-dried preparation containing PTH peptide set forth in [11] characterized in that the freeze-drying means is a freeze-drying chamber having an easily openable and closable sub-door provided in an opening created in a small door unit opened when containers housing the solution containing PTH peptide prior to freeze drying are loaded into and unloaded from this means, thereby controlling exposure of the solution containing PTH peptide to air environments within a pharmaceutical production facility prior to freeze drying by opening this sub-door only during container loading and quickly closing the sub-door after loading.

[13] A freeze-dried preparation containing PTH peptide set forth in [11] wherein the freeze-drying means is a freeze-drying chamber having an opening created in a small door unit opened when containers housing the solution containing PTH peptide prior to freeze drying are loaded into and unloaded from this means, and the means for controlling the ingress of air within a pharmaceutical production facility into the freeze-drying means is an airflow-adjusting cover that can change the air flow to a direction not directed from this opening to the inside of the chamber.

[14] The freeze-dried preparation containing PTH peptide set forth in [10] characterized in that the loading step controls exposure of the solution containing PTH peptide to air environments within a pharmaceutical production facility prior to freeze drying by purging the inside of the freeze-drying means with an inert gas.

[15] The freeze-dried preparation containing PTH peptide set forth in [10] wherein the freeze-drying means is a freeze-drying chamber having an easily openable and closable sub-door provided in an opening created in a small door unit opened when containers housing the solution containing PTH peptide prior to freeze drying are loaded into and unloaded from this means, thereby controlling exposure of the solution containing PTH peptide to air environments within a pharmaceutical production facility prior to freeze drying by opening this sub-door only during container loading and quickly closing the sub-door after loading and purging the inside of the freeze-drying means with an inert gas in the loading step.

[16] The freeze-dried preparation containing PTH peptide set forth in [10] wherein the freeze-drying means is a freeze-drying chamber having an opening created in a small door unit opened when containers housing the solution containing PTH peptide prior to freeze drying are loaded into and unloaded from this means, this opening being equipped with an airflow-adjusting cover, thereby controlling exposure of the solution containing PTH peptide to air environments within a pharmaceutical production facility prior to freeze drying by changing the direction of the airflow-adjusting cover so that air is not directed into the chamber and purging the inside of the freeze-drying means with an inert gas in the loading step.

[17] A freeze-dried preparation containing PTH peptide according to any of [10] to [16] wherein the loading step is a step that spans three or more hours.

[18] The freeze-dried preparation containing PTH peptide according to any of [8] to [17] wherein time from the beginning of the step for preparing a solution containing PTH peptide to the end of the step for loading into the freeze-drying means spans three or more hours, and production is performed using a method for controlling exposure of the solution containing PTH peptide to an air environment within a pharmaceutical production facility in one or more steps during the time.

[19] A freeze-dried preparation containing PTH peptide according to any of [14] to [18] wherein the inert gas is nitrogen gas.

[20] A freeze-dried preparation containing high-purity PTH peptide as an active ingredient, the PTH-peptide-containing freeze-dried preparation manufactured using a method characterized in that exposure of a solution containing PTH peptide to air environments within a pharmaceutical production facility prior to freeze drying is controlled during loading into the freeze-drying means; wherein "high-purity" means at least that the amount of at least one PTH analog versus the sum of the amount of PTH peptide and the total amount of PTH analogs in the preparation is 1.0% or less and/or that the total amount of PTH analogs versus the sum of the amount of PTH peptide and the total amount of PTH analogs is 5.0% or less; the loading step is a step that spans three or more hours; the air environment is an environment that maintains one-way air flow of clean air that has passed through an HEPA filter downward from above; and the velocity of the air flow 20 cm directly under the HEPA filter is 0.2-1.0 m/s.

[21] A method for producing a freeze-dried preparation containing PTH peptide, the method being characterized in that exposure of the solution containing PTH peptide to air environments within a pharmaceutical production facility is controlled in one or more steps from the beginning of the step for preparing a solution containing PTH peptide to the end of the step for loading into a freeze-drying means.

[22] The method set forth in [21] wherein exposure of the freeze-dried product to air environments within a pharmaceutical production facility is also controlled in the step for sealing vials after freeze drying.

[23] The method set forth in [21] or [22] characterized in that exposure of the solution containing PTH peptide to air environments within a pharmaceutical production facility is controlled in the step for loading into a freeze-drying means.

[24] The method set forth in [23] characterized in that exposure is controlled using a freeze-drying chamber equipped with means for controlling the inflow of air within a pharmaceutical production facility into the freeze-drying means.

[25] The method set forth in [23] or [24] wherein the step for loading into the freeze-drying means is a step that spans three or more hours.

[26] The method set forth in [24] or [25] wherein the freeze-drying means is a freeze-drying chamber having an easily openable and closable sub-door provided in an opening created in a small door unit opened when containers housing the solution containing PTH peptide prior to freeze drying are loaded and unloaded, thereby controlling exposure of the solution containing PTH peptide to air environments within a pharmaceutical production facility prior to freeze drying by opening this sub-door only during container loading and quickly closing the sub-door after loading.

[27] The method set forth in [24] or [25] wherein the freeze-drying means is a freeze-drying chamber having an opening created in a small door unit opened when containers housing the solution containing PTH peptide prior to freeze drying are loaded into and unloaded from this means, and the means for controlling the ingress of air within a pharmaceutical production facility into the freeze-drying means is an airflow-adjusting cover that can change the air flow to a direction not directed from this opening to the inside of the chamber.

[28] The method set forth in [23] or [25] characterized in that exposure of the solution containing PTH peptide to air environments within a pharmaceutical production facility prior to freeze drying is controlled by purging the inside of the freeze-drying means with an inert gas.

[29] The method set forth in [23] or [25] characterized in that the freeze-drying means is a freeze-drying chamber having an easily openable and closable sub-door provided in an opening created in a small door unit opened when containers housing the solution containing PTH peptide prior to freeze drying are loaded and unloaded, thereby controlling exposure of the solution containing PTH peptide to air environments within a pharmaceutical production facility prior to freeze drying by opening this sub-door only during container loading and quickly closing the sub-door after loading and purging the inside of the freeze-drying means with an inert gas in the loading step.

[30] The method set forth in [23] or [25] characterized in that the freeze-drying means is a freeze-drying chamber having an opening created in a small door unit opened when containers housing the solution containing PTH peptide prior to freeze drying are loaded into and unloaded from this means, this opening being equipped with an airflow-adjusting cover, thereby controlling exposure of the solution containing PTH peptide to air environments within a pharmaceutical production facility prior to freeze drying by changing the airflow-adjusting cover to a direction in which the air flow is not directed into the chamber and purging the inside of the freeze-drying means with an inert gas in the loading step.

[31] The method set forth in any of [28] to [30] wherein the inert gas is nitrogen.

[32] The method set forth in any of [21] to [31] wherein the container housing the solution containing PTH peptide is a glass vial.

[33] The method set forth in any of [21] to [32] wherein the PTH is human PTH (1-34).

[34] The method set forth in any of [21] to [33] wherein the air environment within a pharmaceutical production facility is an air environment in which 1) the air is of grade A, 2) clean air that has passed through an HEPA filter having the ability to trap particles having a particle size of 0.3 μm at an efficiency of 99.97% or higher is maintained as a one-way air flow downward from above, and 3) the ozone concentration is 0.001-0.1 ppm.

[35] The method set forth in any of [21] to [34] wherein the air environment within a pharmaceutical production facility is an air environment containing a formaldehyde concentration of 0.1 ppm or less.

[36] The method set forth in any of [21] to [35] wherein the amount of at least one PTH analog versus the sum of the amount of PTH peptide and total amount of PTH analogs is 1.0% or less and/or the total amount of PTH analogs versus the sum of the amount of PTH peptide and total amount of PTH analogs is 5.0% or less in the freeze-dried preparation containing PTH peptide.

[37] The method set forth in any of [21] to [36] to control the production of PTH analogs 1 to 11 set forth in [2].

[38] The method set forth in any of [21] to [36] to control the production of PTH analogs 1' to 11' set forth in [3].

[39] A freeze-dried preparation containing PTH peptide manufactured using the method according to any of [21]-[38].

[40] A method for producing a freeze-dried preparation containing high-purity PTH peptide as an active ingredient, the method characterized in that exposure of a solution containing PTH peptide to air environments within a pharmaceutical production facility prior to freeze drying is controlled during loading into the freeze-drying means; wherein "high-purity" means at least that the amount of at least one PTH analog versus the sum of the amount of PTH peptide and the total amount of PTH analogs is 1.0% or less and/or that the total amount of PTH analogs versus the sum of the amount of PTH peptide and the total amount of PTH analogs is 5.0% or less in the preparation; the loading step is a step that spans three or more hours; the air environment is an environment in which clean air that has passed through an HEPA filter is maintained as a one-way air flow downward from above; and the velocity of the air flow 20 cm directly under the HEPA filter is 0.2-1.0 m/s.

The present invention also intends a test method that is important for compliance with laws and regulations and assurance of compatibility of the freeze-dried preparation containing PTH peptide as a pharmaceutical. This test method is characterized in confirming the presence of any one or more or all of the above PTH analogs and/or determines the amounts present. The following are also encompassed as aspects and preferred embodiments.

[41] A method for testing a freeze-dried preparation containing PTH peptide, the method being characterized in confirming the presence of at least one or more of the PTH analogs 1 to 11 of [2] and/or determining the amounts present in the freeze-dried preparation containing PTH peptide.

[42] A method for testing a freeze-dried preparation containing PTH peptide, the method being characterized in confirming the presence of at least one or more of the PTH analogs 1' to 11' of [3] and/or determining the amounts present in the freeze-dried preparation containing PTH peptide.

[43] The method set forth in [41] or [42] wherein determination of the PTH analogs includes calculating the area of the peak corresponding to the PTH analog on a chromatogram when the ultraviolet absorption of a sample derived from a freeze-dried preparation containing PTH peptide is measured by high-performance liquid chromatography.

[44] The method set forth in [43] including calculation of the purity of the PTH peptide in the freeze-dried preparation containing PTH peptide by comparing the area of a peak corresponding to a PTH analog on a chromatogram and the peak area corresponding to PTH peptide or the sum of the peak area of PTH peptide and the peak area of all other PTH analogs detected on the same chromatogram when the ultraviolet absorbance of a sample derived from a freeze-dried preparation containing PTH peptide is measured by high-performance liquid chromatography.

[45] The method set forth in [44] including calculation of the purity of the PTH peptide in a freeze-dried preparation containing PTH peptide by comparing the area of that peak and the peak area corresponding to PTH peptide or the sum of the peak area of PTH peptide and the peak area of all other PTH analogs detected on the same chromatogram when using chromatography conditions such that any two or more PTH analogs are detected as one or more single peaks on the chromatogram.

[46] The method set forth in any of [41] to [45] for ensuring that the amount of at least one PTH analog versus the sum of the amount of PTH peptide and the total amount of PTH analogs is 1.0% or less and/or the total amount of PTH analogs versus the sum of the amount of PTH peptide and the total amount of PTH analogs is 5.0% or less in a freeze-dried preparation containing PTH peptide.

[47] The method set forth in any of [41] to [46] including the detection of the mass number of the PTH analogs using a high-performance liquid chromatograph-mass spectrometer.

[48] The method set forth in any of [41] to [47] including fractionating a substance that gives a single peak on the chromatogram and identifying the mass number of the fragments produced by digesting this substance using trypsin.

[49] A method for producing a pharmaceutical comprising a freeze-dried preparation containing PTH peptide including a step to carry out the test method of any of [41] to [48].

The following aspects are also intended as preferred freeze-dried preparations containing PTH peptide of the present invention.

[50] A freeze-dried preparation containing PTH peptide, the freeze-dried preparation containing PTH peptide being characterized in that at least one or more PTH analogs is 1.0% or less versus the sum of the amount of PTH peptide and the total amount of PTH analogs and/or the total amount of PTH analogs is 5.0% or less versus the sum of the amount of PTH peptide and the total amount of PTH analogs.

[51] A freeze-dried preparation containing PTH peptide, the freeze-dried preparation containing PTH peptide being characterized in that any of the respective PTH analogs is 1.0% or less versus the sum of the amount of PTH peptide and the total amount of PTH analogs and/or the total amount of PTH analogs is 5.0% or less versus the sum of the amount of PTH peptide and the total amount of PTH analogs.

[52] A freeze-dried preparation containing PTH peptide set forth in [50] or [51] wherein the PTH analog is an analog set forth in [2].

[53] A freeze-dried preparation containing PTH peptide set forth in [50] or [51] wherein the PTH analog is an analog set forth in [3].

[54] A freeze-dried preparation containing PTH peptide set forth in [52] wherein the amount of analogs versus the sum of the amount of PTH peptide and the total amount of PTH analogs is in at least the following relationships:
 the amount of analog 1 is 0.04% or less;
 the total amount of analog 3 and analog 4 is 0.11% or less;
 the amount of analog 5 is 0.26% or less;
 the amount of analog 7 is 0.33% or less;
 the amount of analog 8 is a percentage selected arbitrarily from 0.21-1.00%; and
 the amount of analog 9 is 0.68% or less.

[55] A freeze-dried preparation containing PTH peptide set forth in [53] wherein the amount of analogs versus the sum of the amount of PTH peptide and the total amount of PTH analogs is in at least the following relationships:
 the amount of analog 1' is 0.04% or less;
 the total amount of analog 3' and analog 4' is 0.11% or less;
 the amount of analog 5' is 0.26% or less;
 the amount of analog 7' is 0.33% or less;

the amount of analog 8' is a percentage selected arbitrarily from 0.21-1.00%; and the amount of analog 9' is 0.68% or less.

[56] A freeze-dried preparation containing PTH peptide set forth in [52] wherein the amount of analog 1, amount of analog 2, total amount of analog 3 and analog 4, amount of analog 5, amount of analog 6, amount of analog 7, amount of analog 8, amount of analog 9, and total amount of analog 10 and analog 11 are all 1.0% or less versus the sum of the amount of PTH peptide and the total amount of PTH analogs.

[57] A freeze-dried preparation containing PTH peptide set forth in [53] wherein the amount of analog 1', amount of analog 2', total amount of analog 3' and analog 4', amount of analog 5', amount of analog 6', amount of analog 7', amount of analog 8', amount of analog 9', and total amount of analog 10' and analog 11' are all 1.0% or less versus the sum of the amount of PTH peptide and the total amount of PTH analogs.

[58] A freeze-dried preparation containing PTH peptide according to any of [50] to [57] wherein the freeze-dried preparation containing PTH peptide is a preparation housed in a stoppered glass container.

[59] A freeze-dried preparation containing PTH peptide according to any of [50] to [58] wherein the freeze-dried preparation containing PTH peptide is a glass vial preparation.

[60] A freeze-dried preparation containing PTH peptide according to any of [50] to [59] wherein the PTH peptide is human PTH (1-34)

A freeze-dried preparation containing high-purity PTH is provided by the present invention. Specifically, the production of PTH analogs characterized and confirmed to be produced in the freeze-dried preparation containing PTH which is undesirable during pharmaceutical manufacture is inhibited and decreased in the present invention. A preparation qualified as a pharmaceutical can also be produced while confirming and assuring the quality of the freeze-dried preparation containing PTH simply, rapidly, and accurately by determining the PTH analogs.

BRIEF DESCRIPTION OF THE DRAWINGS

FIG. 16 is a schematic diagram showing an example of preferred freeze-drying means of the present invention. The diagram shows a Large door (1), Small door (2), Sub-door (open)(3), and a Sub-door (closed)(4).

FIG. 17 is a schematic diagram showing an example of preferred freeze-drying means of the present invention. The diagram shows an Airflow-adjusting cover (5).

Figure 1:
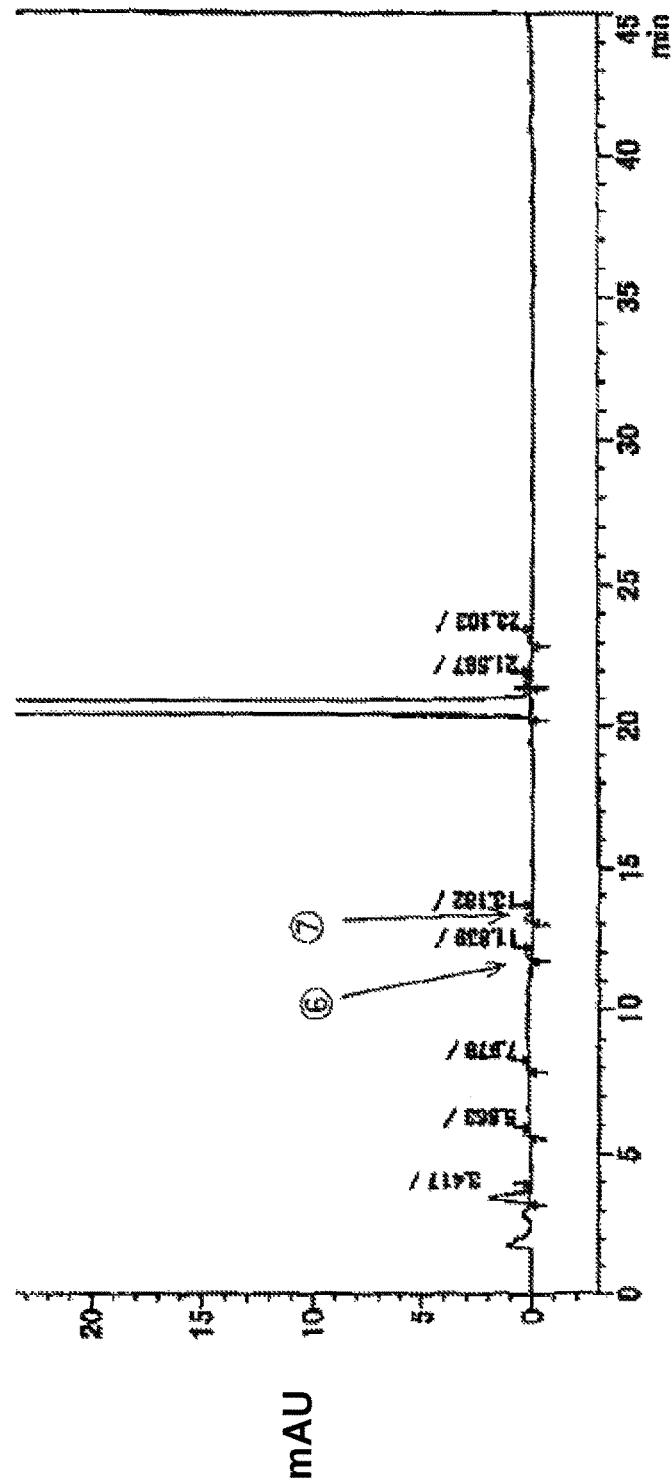
FIG. 1 shows the chromatograms when the ultraviolet (214 nm) absorbance was measured by high-performance liquid chromatography (HPLC) taking as the sample a PTH peptide used as a raw material of a PTH peptide freeze-dried preparation produced as a working example and comparative example. The horizontal axis represents the time (min), and the vertical axis represents the absorption intensity. The large peak appearing at approximately 20-21 minutes is human PTH (1-34). "6 (encircled number)" corresponds to analog 7', and "7 (encircled number)" corresponds to analog 8'.

The present invention shall now be described in further detail.

(1) PTH Peptide

The term "PTH peptide" in the present invention is used as a collective term for natural PTH and substances of equivalent physiologic activity. The physiologic activity of PTH is characterized as acting to raise the serum calcium. Preferred PTH peptides encompass natural PTH and partial peptides thereof, which may be peptides having a molecular weight of from about 4000 to 10,000. However, PTH peptides are those wherein any of the constituent amino acid residues have not been chemically modified at all in comparison to the natural form; they do not include the (2) PTH analogs discussed later. Concrete examples of partial peptides include human PTH (1-34), human PTH (1-35), human PTH (1-36), human PTH (1-37), human PTH (1-38), human PTH (1-84), and the like, all of which have a sequence of 34-84 amino acids. Specifically, human PTH (1-34) is a partial peptide of the natural form sequence corresponding to amino acids numbers 1-34 of natural human PTH. Human PTH (1-34) and human PTH (1-84) are preferred, and human PTH (1-34) is especially preferred. The amino acid sequence of human PTH (1-34) is as follows:

[Chemical Formula 4]

(SEQ ID NO: 4)
H-Ser-Val-Ser-Glu-Ile-Gln-Leu-Met-His-Asn-Leu-Gly-
Lys-His-Leu-Asn-Ser-Met-Glu-Arg-Val-Glu-Trp-Leu-
Arg-Lys-Lys-Leu-Gln-Asp-Val-His-Asn-Phe-OH

The PTH peptide of the present invention may also be present as a salt formed with one or more volatile organic acids. Examples of volatile organic acids include trifluoroacetic acid, formic acid, acetic acid, and the like. Acetic acid can be given as a preferred example, but preferred examples are not limited to this. The ratio of the two when free PTH peptide and a volatile organic acid form a salt is not particularly restricted as long as a salt forms. For example, since human PTH (1-34) has nine basic amino acid residues and four acidic amino acid residues in its molecule, taking into consideration salt formation in these molecules, the basic amino acid 5 residue can be made into a chemical equivalent of acetic acid. For example, if an acetic acid content represented by the acetic acid weight×100(%)/peptide weight of human PTH (1-34) is used as the amount of acetic acid, as one theory, the chemical equivalent of acetic acid versus free human PTH (1-34) becomes approximately 7.3% (wt %). In this specification, free human PTH (1-34) sometimes is also called "teriparatide," and the acetate of teriparatide is sometimes also called "teriparatide acetate." The acetic acid content in teriparatide acetate is not particularly restricted as long the teriparatide and acetic acid form a salt. For example, it may be 7.3%, which is the above theoretical chemical equivalent, or higher, or it may be from more than 0% to less than 1%. More concrete examples of the acetic acid content in teriparatide acetate are 1-7%, preferably 2-6%.

However, regardless of whether the PTH peptide of the present invention is a free compound or a salt thereof, the amount of PTH peptide in the preparation of the present invention, amount of various PTH analogs, amount of PTH analog mixture, and total PTH analogs can be determined by HPLC testing. It should be noted that in this case the PTH peptide and PTH analogs are all determined as free compounds.

(2) PTH Analogs

The term "PTH analog" in the present invention is defined in the broad sense as one detected as a peak different from the PTH peptide which is the active ingredient on the chromatogram when a sample from a freeze-dried preparation containing PTH peptide is subjected to HPLC. Therefore, if detected as one peak different from the original PTH peptide on the chromatogram, all of the chemical substances included in this peak may be regarded together as a single "PTH analog" even when two or more separate chemical substances are present in mixture within the peak. That is, for the purposes of general measurement and confirming the purity of a freeze-dried preparation, even a mixture of multiple chemical substances detectable as a single peak on the HPLC chromatogram is comprehensively termed an "analog" and confirmation of purity, calculation of purity, and the like are broadly performed regarding a single peak consisting of such a mixture as one "analog" for the sake of convenience. There is consequently no problem with regarding a mixture of multiple chemical substances detected as a single peak in HPLC under given conditions comprehensively as one type of "PTH analog."

In the present invention, the PTH analogs discovered to be produced during the production of a freeze-dried preparation containing PTH peptide were characterized as shown in Table 1 below.

TABLE 1

Characterization of PTH analogs

| Analog | Fragment changed (trypsin digestion) | Amino acid changed | Overview of changes | | Estimated structural changes |
|---|---|---|---|---|---|
| | | | Change in mass | Nature of change | |
| 1 | T1 | Met 8 | 16 Da | Oxidation | Human PTH (1-34)-Met 8 |
| | T2 | Met 18 | 16 Da | Oxidation | [O]-Met 18 [O]-Trp 23 |
| | T3 | Trp 23 | 32 Da | a) | [dioxidation] |
| 2 | T1 | Met 8 | 16 Da | Oxidation | Human PTH (1-34)-Met 8 |
| | T2 | Met 18 | 16 Da | Oxidation | [O]-Met 18 [O]-Trp 23 |
| | T3 | Trp 23 | 4 Da | b) | [dioxidation-formic acid elimination] |
| 3 | T1 | Met 8 | 16 Da | Oxidation | Human PTH (1-34)-Met 8 |
| | T2 | Met 18 | 16 Da | Oxidation | [O]-Met 18 [O] |

TABLE 1-continued

Characterization of PTH analogs

| Analog | Fragment changed (trypsin digestion) | Amino acid changed | Overview of changes | | Estimated structural changes |
|---|---|---|---|---|---|
| | | | Change in mass | Nature of change | |
| 4 | T1 | Met 8 | 16 Da | Oxidation | Human PTH (1-34)-Met 8 [O]-Trp 23 [dioxidation] |
| | T3 | Trp 23 | 32 Da | a) | |
| 5 | T2 | Met 18 | 16 Da | Oxidation | Human PTH (1-34)-Met 18 [O]-Trp 23 [dioxidation] |
| | T3 | Trp 23 | 32 Da | a) | |
| 6 | T2 | Met 18 | 16 Da | Oxidation | Human PTH (1-34)-Met 18 [O]-Trp 23 [dioxidation-formic acid elimination] |
| | T3 | Trp 23 | 4 Da | b) | |
| 7 | T1 | Met 8 | 16 Da | Oxidation | Human PTH (1-34)-Met 8 [O] |
| 8 | T2 | Met 18 | 16 Da | Oxidation | Human PTH (1-34)-Met 18 [O] |
| 9 | T3 | Trp 23 | 32 Da | a) | Human PTH (1-34)-Trp 23 [dioxidation] |
| 10 | T3 | Trp 23 | 16 Da | c) | Human PTH (1-34)-Trp 23 [monoxidation] |
| 11 | T3 | Trp 23 | 4 Da | b) | Human PTH (1-34)-Trp 23 [dioxidation-formic acid elimination] |

In the above Table 1, T1-T3 are typical fragments produced when each analog is digested by trypsin and are as follows when listed based on the amino acid sequence of the human PTH (1-34) sequence.

[Chemical Formula 5]

T1: (corresponding to positions 1-13 of human PTH (1-34) Ser-Val-Ser-Glu-Ile-Gln-Leu-Met-His-Asn-Leu-Gly-Lys (SEQ ID NO: 1)

T2: (corresponding to positions 14-20 of human PTH (1-34) His-Leu-Asn-Ser-Met-Glu-Arg (SEQ ID NO: 2)

T3: (corresponding to positions 21-25 of human PTH (1-34) Val-Glu-Trp-Leu-Arg (SEQ ID NO: 3)

The numbers of the amino acids changed in Table 1 are expressed as the corresponding amino acid numbers of the human PTH (1-34) sequence. The same notation is used in this specification unless otherwise indicated.

In the estimated structures of Table 1, human PTH (1-34)-Met 8 [O]-Met 18 [O]-Trp 23 [dioxidation] (analog 1') means a PTH analog in which the residues corresponding to the position 8 and 18 methionine of human PTH (1-34) are each methionine sulfoxide residues, the residue corresponding to the position 23 tryptophan is a residue shown by the following structure (a) (Trp 23 oxidation (a) residue), and the other structures are the same as the original PTH peptide.

[Chemical Formula 6]

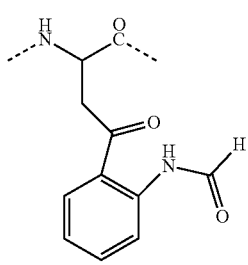

(a)

Human PTH (1-34)-Met 8 [O]-Met 18 [O]-Trp 23 [dioxidation-formic acid elimination] (analog 2') means a PTH analog in which the residues corresponding to the position 8 and 18 methionine of human PTH (1-34) are each methionine sulfoxide residues, the residue corresponding to the position 23 tryptophan is a residue shown by the following structure (b) (Trp 23 oxidation (b) residue), and the other structures are the same as the original PTH peptide.

[Chemical Formula 7]

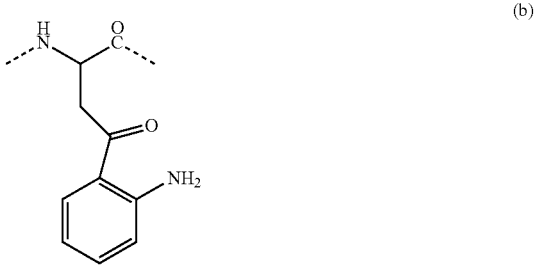

(b)

Similarly, human PTH (1-34)-Met 8 [O]-Met 18 [O] (analog 3') means a PTH analog in which residues corresponding to the position 8 and 18 methionine of human PTH (1-34) are each methionine sulfoxide residues and the other structures are the same as the original PTH peptide. Human PTH (1-34)-Met 8 [O]-Trp 23 [dioxidation] (analog 4') means a PTH analog in which the residue corresponding to the position 8 methionine of human PTH (1-34) is a methionine sulfoxide residue, the residue corresponding to the position 23 tryptophan is a Trp 23 oxidation (a) residue, and the other structures are the same as the original PTH peptide. Furthermore, analog 3' and analog 4' tend to be detected as a single peak, depending on the HPLC conditions. In this case, the PTH analog may be defined as a mixture of analog 3' and analog 4' as discussed above.

Human PTH (1-34)-Met 18 [O]-Trp 23 [dioxidation] (analog 5') means a PTH analog in which the residue corresponding to the position 18 methionine of human PTH (1-34) is a methionine sulfoxide residue, the residue corresponding to the position 23 tryptophan is a Trp 23 oxidation (a) residue, and the other structures are the same as the original PTH peptide.

Human PTH (1-34)-Met 18 [O]-Trp 23 [dioxidation-formic acid elimination] (analog 6') means a PTH analog in which the residue corresponding to the position 18 methionine of human PTH (1-34) is a methionine sulfoxide residue, the residue corresponding to the position 23 tryptophan is a Trp 23 oxidation (b) residue, and the other structures are the same as the original PTH peptide.

Human PTH (1-34)-Met 8 [O] (analog 7') means a PTH analog in which the residue corresponding to the position 8 methionine of human PTH (1-34) is a methionine sulfoxide residue and the other structures are the same as the original PTH peptide.

Human PTH (1-34)-Met 18 [O] (analog 8') means a PTH analog in which the residue corresponding to the position 18 methionine of human PTH (1-34) is a methionine sulfoxide residue and the other structures are the same as the original PTH peptide.

Human PTH (1-34)-Trp 23 [dioxidation] (analog 9') means a PTH analog in which the residue corresponding to the position 23 tryptophan of human PTH (1-34) is a Trp 23 oxidation (a) residue and the other structures are the same as the original PTH peptide.

Human PTH (1-34)-Trp 23 [monoxidation] (analog 10') means a PTH analog in which the residue corresponding to the position 23 tryptophan of human PTH (1-34) is a residue shown by the following structure (c)-1 or (c)-2 (Trp 23 oxidation (c) residue) residue and the other structures are the same as the original PTH peptide.

[Chemical Formula 8]

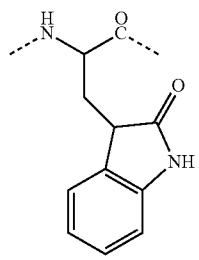

(c)-1

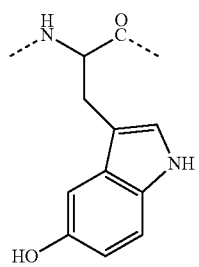

(c)-2

Human PTH (1-34)-Trp 23 [dioxidation-formic acid elimination] (analog 11') means a PTH analog in which the residue corresponding to the position 23 tryptophan of human PTH (1-34) is a Trp 23 oxidation (b) residue and the other structures are the same as the original PTH peptide. Furthermore, analog 10' and analog 11' tend to be detected as a single peak, depending on the HPLC conditions. In this case, the PTH analog may be defined as a mixture of analog 10' and analog 11' as discussed above In the above analogs 1' to 11', the PTH peptide changes in that modified amino acid residues produced by oxidation of either methionine or tryptophan are introduced. It is therefore logical to assume that the production of the PTH analogs of the present invention is begun by contact between a substance having oxidizing capability and the PTH peptide. In this specification, a "substance having oxidizing capability" means a substance having the capacity to oxidize a structural amino acid of the PTH peptide, especially methionine or tryptophan. Given that ozone, formaldehyde, and other such oxidizing gaseous molecules are sometimes present in the air inside a pharmaceutical production facility, as discussed above, such substances capable of oxidizing methionine and tryptophan which may be contained in the air inside a pharmaceutical production facility are of interest as "substances having oxidizing capability" in this specification.

Furthermore, as is evident from the above, the above definition of PTH analogs can be applied even when the PTH peptide contained as an active ingredient is other than human PTH (1-34). For example, when human PTH (1-84) is used as an active ingredient, the corresponding analog 1' can also be expressed as human PTH (1-84)-Met 8 [O]-Met 18 [O]-Trp 23 [dioxidation]. In this case, the analog can be specified as one in which the position 8 and 18 methionine residues of human PTH (1-84) are each methionine sulfoxide residues, the position 23 tryptophan residue is a Trp 23 oxidation (a) residue, and the other structures are the same as human PTH (1-84).

(3) Detection and Determination of PTH Analogs

The PTH analogs in a freeze-dried preparation containing PTH can be detected or determined by producing a sample by dissolving the preparation in a suitable solvent (phosphate buffer containing benzalkonium chloride or the like) and subjecting this sample to HPLC under, for example, the following conditions.

<HPLC Conditions> a) Detector: Ultraviolet absorptiometer (measurement wavelength: 214 nm)

b) Column: Stainless steel tube 150 mm long having an inner diameter of 4.6 mm packed with 3.5 μm of octadecylsilylated silica gel for liquid chromatography (Zorbax 300SB-C18 manufactured by Agilent Technologies or an equivalent product)

c) Column temperature: Constant temperature near 40° C.

d) Mobile phase:

Mobile phase A: Dissolve 28.4 g of anhydrous sodium sulfate in 900 mL of water and bring to 1000 mL by adding water after adding phosphoric acid to adjust the pH to 2.3. Add 100 mL of acetonitrile to this 900 mL of liquid.

Mobile phase B: Dissolve 28.4 g of anhydrous sodium sulfate in 900 mL of water and bring to 1000 mL by adding water after adding phosphoric acid to adjust the pH to 2.3 Add 500 mL of acetonitrile to 500 mL of this liquid.

e) Mobile phase feed: Concentration gradient control is provided by varying the mixture ratio of mobile phase A and mobile phase B as shown in Table 2.

TABLE 2

Concentration gradient control

| Time after sample injection (min) | Mobile phase A (vol %) | Mobile phase B (vol %) |
|---|---|---|
| 0-5 | 100→65 | 0→35 |
| 5-35 | 65→60 | 35→40 |
| 35-45 | 60→0 | 40→100 | f) Flow rate: 1.0 mL/min
g) Detection time: 45 minutes after injection of the sample solution. However, this is from the back of the solvent peak.

Since the PTH peptide and PTH analogs of the present invention have substantial absorbance in the ultraviolet region, monitoring the ultraviolet absorption is advantageous for their detection and determination. The measurement wavelength is not particularly restricted as long as it allows detection of the PTH peptide and PTH analogs. One or more wavelengths may be selected, for example, in the range of 210-360 nm, preferably 210-280 nm, and more preferably 210-254 nm. One example of a suitable wavelength is 214 nm. A chromatogram can be produced based on the measured values of this ultraviolet absorption.

The amount of each PTH analog and the amount of PTH peptide can be determined by calculating each peak area (e.g., by automatic integration) on the chromatogram based on the chromatogram obtained by performing HPLC as discussed above. The amount of each PTH analog (%) and the total amount of PTH analogs (%) can then be determined and compared based on the calculated values by the following formulas 1 and 2. Furthermore, the "total peak area" in the formulas is a value determined by adding the peak area of PTH peptide and the peak areas of all other PTH analogs detected on the chromatogram. Therefore, the "total peak area" corresponds to the "sum of the amount of PTH peptide and total amount of PTH analogs." In addition, unless specifically indicated otherwise, "%" has the meaning of the following formula in the present invention.

Amount of each PTH analog (%)=(peak area of each analog/total peak area)×100  <Formula 1>

Total amount of PTH analogs (%)=(sum total of peak areas of each analog/total peak area)×100  <Formula 2>

Furthermore, analogs 3 and 4 (analogs 3' and 4') produced from human PTH (1-34) elute as a single peak, as was mentioned above, when HPLC is carried out under the above conditions. Since regarding this single peak as one analog does not affect the results when used to confirm the purity or measure the preparation in this case, the mixed peak of analogs 3 and 4 (analogs 3' and 4') may be regarded as one analog. The same is also true of analogs 10 and 11 (analogs 10' and 11').

Table 3 below shows a typical measurement example when HPLC was performed under the above conditions on a sample derived from a freeze-dried preparation containing human PTH (1-34). Furthermore, the notation "approximate relative retention time" in the table is because the relative retention time also sometimes changes depending on the column used or the mobile phase flow rate. Nonetheless, each analog can be identified and determined based on the pattern of the chromatogram taking this relative retention time as a criterion even in this case.

TABLE 3

HPLC measurement example

| PTH analog | Approximate relative retention time, taking the retention time of human PTH (1-34) as 1.00 |
|---|---|
| (1) Human PTH (1-34)-Met 8 [O]-Met 18 [O]-Trp 23 [dioxidation] | 0.49 |
| (2) Human PTH (1-34)-Met 8 [O]-Met 18 [O]-Trp 23 [dioxidation-formic acid elimination] | 0.50 |
| (3) Mixture containing human PTH (1-34)-Met 8 [O]-Met 18 [O] and human PTH (1-34)-Met 8 [O]-Trp 23 [dioxidation] | 0.52 |
| (4) Human PTH (1-34)-Met 18 [O]-Trp 23 [dioxidation] | 0.55 |
| (5) Human PTH (1-34)-Met 18 [O]-Trp 23 [dioxidation-formic acid elimination] | 0.57 |
| (6) Human PTH (1-34)-Met 8 [O] | 0.60 |
| (7) Human PTH (1-34)-Met 18 [O] | 0.66 |
| (8) Human PTH (1-34)-Trp 23 [dioxidation] | 0.69 |
| (9) Mixture containing human PTH (1-34)-Trp 23 [monoxidation] and human PTH (1-34)-Trp 23 [dioxidation-formic acid elimination] | 0.74 |

(4) Freeze-Dried Preparation Containing PTH Peptide

A freeze-dried preparation containing PTH peptide of the present invention means a freeze-dried preparation containing PTH peptide as an active ingredient.

One embodiment of the freeze-dried preparation containing PTH peptide of the present invention is a freeze-dried preparation containing PTH peptide wherein the amount of a PTH analog in the preparation is 1.0% or less versus the "sum of the amount of PTH peptide and total amount of PTH analogs" and/or the total amount of PTH analogs in the preparation is 5.0% or lower versus the "sum of the amount of PTH peptide and total amount of PTH analogs."

Another embodiment of the freeze-dried preparation containing PTH peptide of the present invention is a freeze-dried preparation containing PTH peptide wherein the amount of any of the respective PTH analogs is 1.0% or less versus the "sum of the amount of PTH peptide and total amount of PTH analogs" and/or the total amount of PTH analogs in the preparation is 5.0% or lower versus the "sum of the amount of PTH peptide and total amount of PTH analogs." Furthermore, "1.0% or less" and "5.0% or less" mean when absolutely no PTH analogs are contained in the freeze-dried preparation containing PTH peptide of the present invention or when that % or less is contained.

Preferably, the freeze-dried preparation containing PTH peptide of the present invention does not contain any more than 1.0% of at least one or more PTH analogs versus the "sum of the amount of PTH peptide and total amount of PTH analogs," and more preferably does not contain more than 1.0% of any PTH analog versus the "sum of the amount of PTH peptide and total amount of PTH analogs." In addition, when two analogs give a single peak on the chromatogram, as mentioned above, the single peak is regarded as one analog, and the analog regarded in this way is more preferably not contained in an amount exceeding 1.0% versus the "sum of the amount of PTH peptide and total amount of PTH analogs." The amount of each PTH analog in the preparation is preferably "1.0% or less," but 0.9% or less, 0.8% or less, 0.7% or less, and 0.6% or less are also preferred. Moreover, the total amount of PTH analogs is preferably "5.0% or less," but 4.5% or less, 4.0% or less, 3.5% or less, and 3.0% or less are also preferred.

An example of a suitable freeze-dried preparation containing PTH peptide of the present invention appears below as Table 4. (Furthermore, the "total amount of PTHs" in the table means the "sum of the amount of PTH peptide and total amount of PTH analogs.)

TABLE 4

Suitable freeze-dried preparation containing PTH peptide of the present invention

| PTH analog | Content versus total amount of PTHs (%) |
|---|---|
| (1) PTH-Met 8 [O]-Met 18 [O]-Trp 23 [dioxidation] (e.g. Human PTH (1-34)-Met 8 [O]-Met 18 [O]-Trp 23 [dioxidation]) | 0.04% or less, preferably 0.03% or less |
| (3) Mixture containing PTH-Met 8 [O]-Met 18 [O] and PTH-Met 8 [O]-Trp 23 [dioxidation] (e.g., Mixture containing human PTH (1-34)-Met 8 [O]-Met 18 [O] and human PTH (1-34)-Met 8 [O]-Trp 23 [dioxidation]) | 0.11% or less, preferably 0.10% or less, most preferably 0.03% or less |
| (4) PTH-Met 18 [O]- Trp 23 [dioxidation] (e.g., Human PTH (1-34)-Met 18 [O]-Trp 23 [dioxidation]) | 0.26% or less, preferably 0.20% or less, most preferably 0.06% or less |
| (6) PTH-Met 8 [O] (e.g., Human PTH (1-34)-Met 8 [O]) | 0.33% or less, preferably 0.30% or less, most preferably 0.23% or less |
| (7) PTH-Met 18 [O] (e.g., Human PTH (1-34)-Met 18 [O]) | Arbitrary percentage selected from 1.01-2.00% or less, preferably 1.00% or less, more preferably 0.50% or less, most preferably 0.36% or less |
| (8) PTH-Trp 23 [dioxidation] (e.g., Human PTH (1-34)-Trp 23 [dioxidation]) | 0.68% or less, preferably 0.50% or less, most preferably 0.11% or less |

To further explain the freeze-dried preparation containing PTH peptide of the present invention, the freeze-dried preparation containing PTH peptide of the present invention can contain various additives. Examples of additives include sugars, amino acids, sodium chloride, and the like. When sugars are used as additives, mannitol, glucose, sorbitol, inositol, sucrose, maltose, lactose, or trehalose is preferably added in an amount of 1 weight or more (preferably 50-1000 weights) per weight of PTH peptide. When sugars and sodium chloride are used as additives, sodium chloride is preferably added in an amount of 1/1000-1/5 weight (preferably 1/100 to 1/10 weight) per weight of sugars.

(5) Container of the Freeze-Dried Preparation Containing PTH Peptide of the Present Invention The container used for the freeze-dried preparation containing PTH peptide of the present invention is not particularly restricted, but the preparation is preferably a freeze-dried preparation containing PTH peptide housed in a stoppered glass container. The material of the stopper is not particularly restricted, but rubber is preferred. The stopper is preferably washed, sterilized, and/or dried.

The freeze-dried preparation containing PTH peptide of the present invention housed in a stoppered glass container is, for example, a freeze-dried preparation containing PTH peptide housed in a glass vial having a rubber stopper (glass vial preparation), kit preparation comprising a freeze-dried preparation containing PTH peptide housed in a glass vial having a rubber stopper and an ampule sterilely filled with aqueous solution for dissolution, kit preparation comprising a freeze-dried preparation containing PTH peptide and pre-filled syringe sterilely filled with aqueous solution for dissolution, or glass double chamber preparation (two chambers are present in one syringe, one chamber containing freeze-dried preparation containing PTH peptide and the other containing aqueous solution for dissolution). A glass vial preparation is most preferred as the freeze-dried preparation containing PTH peptide of the present invention. Examples of the material of the rubber stopper include chlorinated butyl rubber, normal butyl rubber, butadiene rubber, isoprene rubber, silicone rubber, elastomer, and the like. Silicate glass is preferred as the glass.

(6) Production of a Freeze-Dried Preparation Containing PTH Peptide

A freeze-dried preparation is produced by a process typically including any or all of the following steps, depending on its use. Unless particularly stated otherwise, the freeze-dried preparation containing PTH peptide of the present invention can also be produced according to the following steps. Specifically the production scheme of the freeze-dried preparation containing PTH peptide of the present invention includes at least an active ingredient-containing solution preparation step and a freeze drying step explained below. It usually includes an active ingredient-containing solution preparation step, loading step, and freeze drying step, and preferably includes an active ingredient-containing solution preparation step, aseptic filtration and drug solution dispensing step, loading step, freeze drying step, and packaging step.

1) Active Ingredient Solution Preparation Step

This step dissolves a bulk compound of the active ingredient and various additives as needed in a solvent (e.g., water for injection). Adjustment of the pH of the solution, adjustment of the volume of the solution, and the like may be performed as needed. The time necessary for this step is not particularly restricted as long as it is within the acceptable range for industrial production, but it may be 0.5-5 hours, usually about 1-3 hours.

When the PTH peptide of the present invention is the active ingredient, it is preferable to dissolve the bulk PTH peptide in advance and add it to a solution in which the various additives have been dissolved. Examples of additives include excipients, stabilizers, dissolution auxiliaries, antioxidants, analgesics, isotonifying agents, pH regulators, and preservatives.

2) Aseptic Filtration and Drug Solution Dispensing Step

This step includes aseptic filtration of the active ingredient-containing solution prepared in the above step and filling a container suited to the performance of the freeze drying step explained below with this aseptic filtered solution (drug solution).

In a typical step, aseptic filtration is carried out using a filter. Various commercial products can be used as the filter for aseptic filtration. The pore size of the filter is preferably 0.2 μm or less or 0.22 μm or less. Specific equipment and the like for performing aseptic filtration is well known to those skilled in the art. Such aseptic filtration makes it possible to prepare a drug solution for producing a freeze-dried preparation to be utilized as a pharmaceutical.

Typical drug solution filling in this step is also well known to those skilled in the art. Usually, individual containers are filled directly with drug solution after aseptic filtration of the solution of the active ingredient. Alternatively, a large amount of solution may be aseptically filtered at once and subsequently dispensed into containers suited to use in the following step. An example of these containers is a glass vial that can be stoppered by a rubber stopper or the like. The use of such glass vials is advantageous in the production of a preparation in a glass vial.

The time necessary for this step is also not particularly restricted as long as it is within the acceptable range for industrial production, but it may be 0.5-2 hours, usually 0.5-1 hour, as the filtration step and 3-10 hours, usually 6-10 hours, as the filling step.

Furthermore, when the freeze-dried preparation containing PTH peptide of the present invention is made into a preparation in a glass vial, one glass vial can be filled, for example, with about 1 g (preferably 0.3-3 g, more preferably 0.5-0.6 g) of aseptically filtered solution containing PTH peptide.

3) Loading Step

The term loading step here means a series of steps whereby the filled containers prepared as described above are transported (transferred) to the freeze-drying means used in the next step and loaded and placed in that means.

The stoppers of the filled containers are usually open or partially open to dry by vacuum the filled solution frozen in a subsequent step in the production of a freeze-dried preparation. An open stopper means that the stopper is completely open, and a partially open stopper means that the stopper is not open but not closed. This makes it possible to vacuum dry the drug solution in the container after freezing. For example, when the product is a preparation in a glass vial, a partially open stoppered state as above is created by stoppering the filled vial partially using a rubber stopper after filling the glass vial by aseptically filtered solution (drug solution). When the freeze-dried preparation containing PTH peptide of the present invention is made as a preparation in a glass vial or the like, a step to provide partial stoppering in this way is also included in this loading step.

A freeze drying means is means making it possible to dry the frozen solution under vacuum. Means for industrial production is preferably also provided with an adequate cooling function to freeze the solution or preferably provided with a function to properly heat the material to be freeze dried during this treatment to accelerate freeze drying. Since the material to be freeze dried is loaded into a chamber in a typical freeze-drying means suited to industrial production, this means has a large door (also referred to as "large door" hereinafter) corresponding to basically its entire front surface. A typical freeze-drying means is a freeze-drying chamber (also called a "freeze dryer"), and many forms of these are marketed.

To explain this step by way of example, taking a preparation in glass vials as an example of the preparation to be produced, a process whereby glass vials filled with drug solution obtained in the above step "2)" are partially stoppered and transported to the freeze-drying means and each vial is loaded sequentially or a quantity unit is loaded together at one time into the freeze-drying chamber and placed therein corresponds to this step. Furthermore, when it is noted here that each vial is "loaded sequentially," depending on the layout of the pharmaceutical production facility, this can mean that each vial is filled one after another continuously by the above drug solution dispensing step, and each vial is then sequentially partially stoppered and transferred (transported) to the freeze-drying means. Usually, however, since the process moves to the next freeze-drying step after all of the vials that can be treated at once by the freeze-drying means have been loaded into the freeze-drying means, each of the vials transported as described above is introduced one after another (that is, "sequential loading") and placed into the freeze-drying means until reaching the quantity that can be treated at once. However, in the case of such "sequential loading," the "loading step" of the present invention means a step that begins with a certain (first) vial after the drug solution dispensing step has been completed until the final vial to be freeze dried together with this (first) vial (that is, at once) has been loaded and placed in the freeze-drying means.

Loading the vials "in a quantity unit together at one time" can mean, for example, that there are multiple trays in the freeze-drying chamber and multiple drug solution-filled vials are placed together on each tray when placing them in the freeze-drying chamber, and sometimes these trays can be moved up and down for the sake of convenience when loading the drug solution-filled vials. In this case as well, the "loading step" of the present invention means a step that begins with a certain (first) vial after the drug solution dispensing step has been completed until the final vial to be freeze dried together with this (first) vial has been loaded and placed in the freeze-drying means. In any case, the drug solution-filled vials are left in a partially open state in this step until the subsequent freeze drying step begins and may be exposed to the air environment within a pharmaceutical production facility explained below.

The time necessary for this step also is not particularly restricted as long as it is within the range acceptable for industrial production, but is 3-10 hours, usually about 6-10 hours.

4) Freeze Drying Step

This is a step for sublimating water from the frozen material to be dried under reduced pressure by the above freeze drying means. When a freeze-dried preparation is produced in glass vials, the vials can be placed in an open or partially open state under reduced pressure (for example, with the vials partially stoppered), and sealed at the end of freeze drying after the space in the vial has been purged by nitrogen.

The time necessary for this step varies depending on the capabilities of the freeze drying means, amount of substance to be freeze dried, and the like and should be within the range acceptable for industrial production. It is usually about 24-72 hours.

5) Closing Step

This step can be included when producing a freeze-dried preparation in a glass vial. Specifically, it is a step whereby the freeze-dried glass vials obtained in the above step "4)" are closed by an aluminum cap by a press-type capping machine, or the like.

6) Packaging Step

This is a step that attaches a label to the preparation and packages it in a paper box or the like.

When a freeze-dried preparation is produced as a pharmaceutical, the production facility must be a facility that meets the pharmaceutical GMP. This facility has drug solution preparation equipment, aseptic filtration equipment, and freeze drying equipment (means) and, in addition to these, water for injection production equipment, vial filling and stoppering equipment, capping machines, labelers, and the like to implement the steps explained above.

When a freeze-dried preparation is produced as a pharmaceutical, all of the above steps 1)-6) or at least from the end of the aseptic filtration step to the beginning of the freeze drying step should be carried out in air environments within a pharmaceutical production facility. That is, the air environment of the pharmaceutical production facility differs from the simple outside air environment. Specifically, it is required that the air environment inside a facility for production of a sterile injection (pharmaceutical) be "a critical area of high cleanliness (the content of suspended microparticles 0.5 µm or greater in size per $m^3$ of air is to be 3520 or fewer during both work and non-work times)." This air quality corresponds to grade A (termed class 100 or ISO 5) according to current, commonly-used domestic and international air quality standards.

The air environment inside the facility that produces a freeze-dried preparation containing PTH peptide of the present invention should be at least equivalent to the air environment inside the above sterile injection production facility, more preferably an environment that maintains a unidirectional flow downward from above of clean air that has passed through HEPA filters capable of trapping particles of 0.3 µm in size at an efficiency of 99.97% or greater. The air flow speed is preferably 0.2-1.0 m/s at a location 20 cm below the HEPA filter and 0.1-0.8 m/s at the location where the production work is carried out, more preferably 0.4-0.7 m/s at a location 20 cm below the HEPA filter and 0.3-0.5 m/s at the location where the production work is carried out.

To create a more sterile air environment inside a pharmaceutical production facility, bacteria suspended in the air and bacteria adhered to machinery, walls, floors, and other such installations are sterilized using ozone or formaldehyde or chemicals having oxidizing capability, such as hydrogen peroxide, peracetic acid, chlorine dioxide, glutaraldehyde, and the like, as disinfectants. The residual formaldehyde concentration after fumigation and sterilization by formaldehyde should usually be kept to 0.1 ppm or lower, preferably 0.08 ppm or lower. Furthermore, in terms of ozone, ozone is usually present even in the outside air in a concentration of 0.001-0.02 ppm as an average daily value. Concentrations of approximately 0.02-0.1 ppm are also sometimes present temporarily depending on the time, location, and season.

As one embodiment of the present invention, a method for producing a freeze-dried preparation containing PTH peptide is characterized in that exposure of the solution containing PTH peptide to the air environment within a pharmaceutical production facility is controlled during the process of the course when a substantial time is required under the air environment within a pharmaceutical production facility as described above at the beginning of the step for preparing a solution of PTH peptide (active ingredient), especially from the end of the drug solution dispensing step to the beginning of the drug solution freeze drying step (that is, loading step).

In the present invention, "exposure to air environments within a pharmaceutical production facility is controlled" and "control of exposure to air environments within a pharmaceutical production facility" mean both that at least one or more of the PTH peptide bulk drug, solution containing PTH peptide, and PTH peptide freeze-dried preparation have absolutely no contact with air environments within a pharmaceutical production facility and that this contact is substantially (e.g., time and level of contact) restricted. For example, in the case of an environment in which clean air that has passed through HEPA filters as described above is maintained as a unidirectional flow in a direction downward from above (referred to hereinafter as "flowing air"), this includes provision of a means to control the time in contact with this flowing air and the contacted air flow rate. Specific examples appear below.

(A) Means to Control Contact of the Solution Containing PTH Peptide with Flowing Air As described above, the present inventors discovered that the generation of impurities (PTH analogs) in solution containing PTH peptide can be controlled by providing means for controlling contact of the solution containing PTH peptide with flowing air. Since flow of the air within the facility is maintained in an ordinary pharmaceutical production facility, it can be deduced that a large amount of air that pours down as air flow comes into contact with the solution containing PTH peptide and that gaseous substances having oxidizing capability (ozone and the like) contained in this air flow increase the PTH analogs in the solution by causing reactions and the like with the PTH peptide in the solution.

The means for controlling contact of the solution containing PTH peptide with flowing air in the present invention is not particularly restricted. Examples include a means for controlling the fluidity and flow of the air in the vicinity of the solution containing PTH peptide and a means for purging the vicinity of the solution containing PTH peptide with an inert gas.

It was also discovered that it is advantageous to provide means for controlling contact of the solution containing PTH peptide with flowing air in the loading step into the freeze-drying chamber.

To explain the above embodiment based on a non-limiting example, an ordinary freeze-drying chamber has a door in the front surface for loading the containers filled with the solution to be freeze dried. This door is often a door (large door) that can cover the entire front surface of the freeze-drying chamber. The present invention, however, at a part of the large door, additionally provides a small door of a size roughly corresponding to one of the trays placed in the freeze-drying chamber (with the filled containers to be freeze dried disposed on top of it), and a freeze-drying chamber having a small door that can be opened and closed easily to load the containers is preferred.

A more preferred example is the above freeze-drying chamber with a small door having sub-doors that can be opened and closed easily provided with openings for loading (also referred to hereinafter as "small door openings") to create small door units to open when loading and unloading the containers filled with the material to be freeze dried into the freeze-drying chamber and a means to open the sub-door only during container loading without leaving it constantly open and to close it quickly after loading. These sub-doors are provided divided into 2-5 levels among the zones corresponding to the small door openings so that only the necessary unit may be opened for loading. Sub-doors that make it possible to open only the necessary location for loading the containers are preferred, and division into 2-3 levels is preferred. Examples of sub-doors that can opened and closed easily include a sub-door that provides a hinge (hinge) at the top of the sub-door and is installed in the small door opening, a sub-door that slides to the right and left, a sub-door that slides up and down, and the like.

Preferred examples of other means of controlling contact of the solution containing PTH peptide and the like with flowing air include sealing the equipment for preparation (tank or container and the like) after the PTH peptide has been dissolved in the solvent in the solution containing PTH peptide preparation step or purging the interior of the container used for preparation by an inert gas during preparation.

The inside of the preparation equipment (tank or container and the like) is sometimes pressurized and the prepared solution containing PTH peptide is passed through a sterile filter and fed to the container or tank for dispensing in the aseptic filtration and drug solution dispensing step. Another preferred example of a means for controlling contact of the solution containing PTH peptide with flowing air is to use an inert gas as the gas for pressurization in this case.

Another preferred example of a means for controlling contact of the solution containing PTH peptide with flowing air is to purge the air inside the drug solution dispensing equipment (tank or container and the like) with an inert gas in advance in the aseptic filtration-drug solution dispensing step and to purge the glass container to be filled with the solution containing PTH peptide with an inert gas in advance.

Alternatively, another preferred example of means for controlling contact of the solution containing PTH peptide with flowing air is to purge the space inside the glass container (part containing air and no drug solution) filled with the solution containing PTH peptide with an inert gas in the aseptic filtration-drug solution dispensing step.

Furthermore, the glass containers filled with the solution containing PTH peptide are sometimes transported from the aseptic filtration-drug solution dispensing equipment to near the freeze-drying chamber during the time after the end of the aseptic filtration-drug solution dispensing step up to loading of the solution containing PTH peptide housed in the open or partially open glass containers into the freeze drying means. Placing the environment during transport under an inert gas flow can also be given as a preferred example of a means for controlling contact of the solution containing PTH peptide with flowing air in such cases.

Alternatively, a flap or airflow-adjusting cover (FIG. 17) that can change the flow of the flowing air from the opening into the chamber can be installed to control the influx of flowing air from the small opening of the freeze-drying chamber into the freeze-drying chamber as a means for controlling contact of the solution containing PTH peptide with flowing air. The shape of this flap or airflow-adjusting cover can be selected as is appropriate to the size of the freeze dryer and small door opening. It may be made of a vinyl sheet, metal, resin, or the like. Furthermore, controlling the influx of flowing air from the small door opening of the freeze-drying chamber into the freeze-drying chamber means that the influx of flowing air is controlled to the point that contact between the solution containing PTH peptide and flowing air is substantially controlled, preferably controlled so that the inflow speed of flowing air from the small door opening is 0.2 m/s or less, more preferably 0.1 m/s or less, and most preferably 0.0 m/s or less. This control can be achieved by proper placement of a flap or airflow-adjusting cover or the like near the small door.

In addition to purging means using inert gas as described above, the means for purging the vicinity of the solution containing PTH peptide with inert gas can be means for purging the air inside the freeze-drying chamber used in the freeze drying step using an inert gas or means for causing an inert gas to flow from the loading port into the freeze-drying chamber when loading the containers of solution containing PTH peptide into the freeze-drying chamber used in the freeze drying step. The flow rate of the inert gas during influx is preferably 0.1-5 $Nm^3$/min, more preferably 0.2-3 $Nm^3$/min, and most preferably 0.3-1 $Nm^3$/min. Examples of the inert gas in purging by an inert gas include nitrogen and argon; nitrogen can be given as a preferred example.

(B) Step that Provides Means for Controlling Contact of the Solution Containing PTH Peptide with Flowing Air The "means for controlling contact of the solution containing PTH peptide with flowing air" of (A) above can be provided in all or some steps included from the beginning of the step for preparing a solution containing PTH peptide to the beginning of the freeze drying step of this solution, and may be provided from the beginning of the step for preparing a solution containing PTH peptide. When the method for producing a freeze-dried preparation containing PTH peptide as a pharmaceutical of the present invention includes a step for preparing a solution containing PTH peptide, a step for loading this solution housed in open or partially open glass containers into a freeze-drying chamber, and a freeze drying step, the means of (A) above can be provided in some or all of the step for loading this solution housed in open or partially open glass containers into a freeze-drying chamber.

(C) Duration of the Step that Provides Means for Controlling Contact of the Solution Containing PTH Peptide with Flowing Air The duration of the step that provides "means for controlling contact of the solution containing PTH peptide with flowing air" of (A) above can have, for example, as the lower limit, one hour or more, preferably three hours or more, and more preferably six hours or more, and, as the upper limit, 20 hours or less, preferably 12 hours or less, more preferably 10 hours or less, and most preferably nine hours or less. Examples of the duration of the step that provides a means of (A) above include 1-20 hours, preferably 3-12 hours, more preferably 6-10 hours, and most preferably 6-9 hours.

(7) Use of the Freeze-Dried Preparation Containing PTH Peptide

The freeze-dried preparation containing PTH peptide of the present invention can contain a pharmaceutically effective amount of PTH peptide and, for example, the freeze-dried preparation can be dissolved in a suitable solvent at the time of use to make an injection and used in the treatment of osteoporosis.

(8) Method for Controlling the Production of PTH Analogs in Solution Containing PTH Peptide The method for controlling the production of PTH analogs of the present invention is a method that provides means for controlling contact of at least one of the PTH peptide bulk drug, solution containing PTH peptide, and freeze-dried preparation containing PTH peptide with substances having oxidizing capability, especially with air containing these substances. A preferred example of a method for controlling the production of PTH analogs is to provide a means for purging air in contact with solution containing PTH peptide by an inert gas (preferably nitrogen). A more preferred example is a method for controlling the production of any one or more PTH analogs among the aforementioned analogs 1 to 11 and analogs 1' to 11' by means for controlling contact of the solution containing PTH peptide with flowing air or means for purging the air in contact with the solution containing PTH peptide by an inert gas (preferably nitrogen).

These production control methods can be implemented in freeze-dried preparation production facilities in air environments within pharmaceutical production facilities as described above. For example, their production in the solution can be controlled by means for controlling contact of the solution with flowing air during the course of the process for a predetermined time or longer from the beginning of the step for preparing a solution containing PTH peptide to the beginning of the freeze drying step of this solution. Preferred embodiments of this means are the same as the preferred embodiments of the corresponding methods for production a freeze-dried preparation containing PTH peptide of the present invention.

EXAMPLES

The present invention is explained more concretely below through examples, reference examples, and test examples without limiting the scope of the invention.

Example 1

Approximately 18 kg of approximately 25° C. water for injection was placed in a 50 L stainless steel container. A quantity of 540 g of sucrose and 27 g of sodium chloride were weighed out into the container and dissolved. Next, 3541 mg of human PTH (1-34) as an acetate (lot A; 860 mg, lot B; 2591 mg, lot C; 90 mg) was added and dissolved. A PTH peptide-containing aqueous solution was then obtained by adding water for injection and correcting the weight to 27 kg. The PTH peptide-containing aqueous solution obtained was aseptically filtered using a filter while pressurizing by nitrogen and fed to a 50 L stainless steel filling tank previously filled with nitrogen. Within a zone having a grade A (air speed approximately 0.2-0.4 m/s) environment within a pharmaceutical production facility, washed and dried glass vials were filled with 0.56 g of this aseptically filtered PTH peptide-containing aqueous solution, and partially open vials were obtained using washed and dried rubber stoppers. Approximately 1000 vials each were lined up on stainless steel trays, and the trays were then transferred to in front of a freeze-drying chamber manufactured by Ulvac (model: DFB, tray areas: 24 m$^2$) previously filled with nitrogen in a grade A zone. While purging the inside of the freeze-drying chamber by nitrogen, a sub-door that matched the width of the trays (a door equivalent to the sub-door of FIG. 16 fitted in-house to the above commercial freeze-drying chamber), provided in the opening when the small door of the above freeze-drying chamber was open, was opened, and the sub-door was shut quickly after the tray had been loaded into the freeze-drying chamber. The same procedure was repeated, and the partially open vials were loaded into the freeze-drying chamber over approximately nine hours. The solution containing PTH was frozen and freeze dried to sublimate off the water under reduced pressure. After the interiors of the glass vials were purged with nitrogen after drying had been completed, the vials were sealed with the rubber stoppers, and capped with aluminum caps, resulting in a freeze-dried preparation containing PTH peptide.

Example 2

Approximately 10 kg of approximately 25° C. water for injection was placed in a 20 L stainless steel container. A quantity of 280 g of sucrose and 14 g of sodium chloride were weighed out into the container and dissolved. Next, the weight was corrected to 14 kg by adding water for injection, and an additive solution was prepared. A PTH peptide-containing aqueous solution was obtained by weighing out 1780 mg (lot D) of human PTH (1-34) as an acetate and dissolving it in 13 kg of the additive solution. The PTH peptide-containing aqueous solution obtained was aseptically filtered using a filter while pressurizing by nitrogen and fed to a 50 L stainless steel filling tank previously filled with nitrogen. Within a zone having a grade A (air speed approximately 0.2-0.4 m/s) environment within a pharmaceutical production facility, washed and dried glass vials were filled with 0.56 g of this aseptically filtered PTH peptide-containing aqueous solution, and partially open vials were obtained using washed and dried rubber stoppers. Approximately 1000 vials each were lined up on stainless steel trays, and the trays were then transferred to in front of a freeze-drying chamber manufactured by Ulvac (model: DFB, tray areas: 24 m$^2$) previously filled with nitrogen in a grade A zone. While purging the inside of the freeze-drying chamber with nitrogen, a sub-door that matched the width of the trays (a door equivalent to the sub-door of FIG. 16 fitted in-house to the above commercial freeze-drying chamber), provided in the opening when the small door of the above freeze-drying chamber was opened, and the sub-door was closed quickly after the tray had been loaded into the freeze-drying chamber. The same procedure was repeated, and the partially open vials were loaded into the freeze-drying chamber over approximately six hours. The solution containing PTH peptide was frozen and freeze dried to sublimate off the water under reduced pressure. After the interiors of the glass vials were purged with nitrogen after drying had been completed, the vials were sealed with the rubber stoppers, capped with aluminum caps, and a freeze-dried preparation containing PTH peptide was obtained.

Example 3

Approximately 19 kg of approximately 25° C. water for injection was placed in a 30 L stainless steel container. A quantity of 460 g of sucrose and 23 g of sodium chloride were weighed out into the container and dissolved. Next, the weight was corrected to 23 kg by adding water for injection, and a placebo solution was prepared. A PTH peptide-containing aqueous solution was obtained by weighing out 2979 mg (lot D) of human PTH (1-34) as an acetate and dissolving it in 22 kg of the placebo solution. The PTH peptide-containing aqueous solution obtained was aseptically filtered using a filter while pressurizing by nitrogen and fed to a stainless steel filling tank previously filled with nitrogen. Within a zone having a grade A (air speed approximately 0.2-0.4 m/s) environment within a pharmaceutical production facility, washed and dried glass vials were filled with 0.56 g of this aseptically filtered PTH peptide-containing aqueous solution, and partially open vials were obtained using washed and dried rubber stoppers. The partially open vials were transferred to a grade A zone, and all of the vials were loaded over approximately six hours into a freeze-drying chamber manufactured by Ulvac (model: DFB, tray areas: 22 m$^2$) previously filled with nitrogen made so that air flow from the opening of the small door does not enter the freeze-drying chamber using a vinyl sheet (a sheet equivalent to the airflow-adjusting cover of FIG. 17 fitted in-house to the above commercial freeze-drying chamber) capable of changing the flow of the flowing air to the opposite direction from the opening of the small door of the freeze-drying chamber. Furthermore, this vinyl sheet capable of changing the flow of the flowing air was also fitted in-house to the above commercial freeze-drying chamber; a vinyl sheet was stretched obliquely downward from the upper part of the opening of the small door, and flowing air was prevented from entering from the opening by changing the direction of the flowing air flowing from above to below. The solution containing PTH peptide was frozen and freeze dried to sublimate off the water under reduced pressure. After the interiors of the glass vials were purged with nitrogen once drying had been completed, the vials were sealed with the rubber stoppers, capped with aluminum caps, and a freeze-dried preparation containing PTH peptide was obtained.

Example 4

Approximately 18 kg of approximately 25° C. water for injection was placed in a 50 L stainless steel container. A quantity of 540 g of sucrose and 27 g of sodium chloride were weighed out into the container and dissolved. Next, 3525 mg of human PTH (1-34) as an acetate (lot C; 1880 mg, lot E; 1645 mg) was added and dissolved. A PTH peptide-containing aqueous solution was then obtained by adding water for injection and correcting the weight to 27 kg. The PTH peptide-containing aqueous solution obtained was aseptically filtered using a filter while pressurizing by nitrogen and fed to a 50 L stainless steel filling tank previously filled with nitrogen. Within a zone having a grade A (air speed approximately 0.2-0.4 m/s) environment and a formalin concentration brought to 0.08 ppm or lower within a pharmaceutical production facility, washed and dried glass vials were filled with 0.56 g of this PTH peptide-containing aqueous solution, and partially open vials were obtained using washed and dried rubber stoppers. Approximately 1000 vials each were lined up on stainless steel trays, and the trays were then transferred to in front of a freeze-drying chamber manufactured by Ulvac (model: DFB, tray areas: 24 m$^2$) previously filled with nitrogen in a grade A zone. While purging the inside of the freeze-drying chamber with nitrogen, a sub-door that matched the width of the trays (a door equivalent to the sub-door of FIG. 16 fitted in-house to the above commercial freeze-drying chamber), provided in the opening when the small door of the above freeze-drying chamber was open, was opened, and the sub-door was closed quickly after the tray had been loaded into the freeze-drying chamber over approximately eight hours. The solution containing PTH peptide was frozen and freeze dried to sublimate off the water under reduced pressure. After the interiors of the glass vials were purged with nitrogen once drying had been completed, the vials were sealed with the rubber stoppers, capped by aluminum caps, and a freeze-dried preparation containing PTH peptide was obtained.

Example 5

Approximately 18 kg of approximately 25° C. water for injection was placed in a 50 L stainless steel container. A quantity of 540 g of sucrose and 27 g of sodium chloride were weighed out into the container and dissolved. Next, 3566 mg of human PTH (1-34) as an acetate (lot H) was added and dissolved. A PTH peptide-containing aqueous solution was then obtained by adding water for injection and correcting the weight to 27 kg. The PTH peptide-containing aqueous solution obtained was aseptically filtered using a filter while pressurizing by nitrogen and fed to a 50 L stainless steel filling tank previously filled with nitrogen. Within a zone having a grade A (air speed approximately 0.2-0.4 m/s) environment and a formalin concentration brought to 0.08 ppm or lower within a pharmaceutical production facility, washed and dried glass vials were filled with 0.56 g of this PTH peptide-containing aqueous solution, and partially open vials were obtained using washed and dried rubber stoppers. Approximately 1000 vials each were lined up on stainless steel trays, and the trays were then transferred to in front of a freeze-drying chamber manufactured by Ulvac (model: DFB, tray areas: 24 m$^2$) previously filled with nitrogen in a grade A zone. While purging the inside of the freeze-drying chamber with nitrogen, a sub-door that matched the width of the trays (a door equivalent to the sub-door of FIG. 16 fitted in-house to the above commercial freeze-drying chamber), provided in the opening when the small door of the above freeze-drying chamber was open, was opened, and the sub-door was closed quickly after the tray had been loaded into the freeze-drying chamber. The same step was repeated, and the partially open vials were loaded into the freeze-drying chamber over approximately seven hours. The solution containing PTH peptide was frozen and freeze dried to sublimate off the water under reduced pressure. After the interiors of the glass vials were purged with nitrogen once drying had been completed, the vials were sealed with the rubber stoppers, capped by aluminum caps, and a freeze-dried preparation containing PTH peptide was obtained.

Comparative Example 1

Approximately 5000 g of approximately 25° C. water for injection was placed in a 10 L stainless steel container. A quantity of 120 g of sucrose and 6 g of sodium chloride were weighed out into the container and dissolved. Next, 909 mg of human PTH (1-34) as an acetate (lot F; 335 mg, lot G; 574 mg) was added and dissolved. A PTH peptide-containing aqueous solution was then obtained by adding water for injection and correcting the weight to 6000 g. The PTH peptide-containing aqueous solution obtained was aseptically filtered using a filter while pressurizing by nitrogen and fed to a stainless steel filling tank. Within a zone having a grade A (air speed approximately 0.2-0.4 m/s) environment within a pharmaceutical production facility, washed and dried vials were filled with 0.56 g of this PTH peptide-containing aqueous solution, and partially open vials were obtained using washed and dried rubber stoppers. The partially open vials were transferred to a grade A zone, and all were sequentially loaded over approximately four hours into a freeze-drying chamber manufactured by Ulvac (model: DFB, tray areas: 22 m$^2$) having a small door. The solution containing PTH peptide was frozen and freeze dried to sublimate off the water under reduced pressure. After the interiors of the glass vials were purged with nitrogen once drying had been completed, the vials were sealed with the rubber stoppers, capped with aluminum caps, and a freeze-dried preparation containing PTH peptide was obtained.

Comparative Example 2

Approximately 2000 g of approximately 25° C. water for injection was placed in a 10 L stainless steel container.

Quantities of 100 g of sucrose and 5 g of sodium chloride were weighed out into the container and dissolved. Next, 515 mg of human PTH (1-34) as an acetate (lot D) was added and dissolved. A PTH peptide-containing aqueous solution was then obtained by adding water for injection and correcting the weight to 4000 g. The PTH peptide-containing aqueous solution obtained was aseptically filtered using a filter while pressurizing by nitrogen and fed to a 5 L stainless steel filling tank. Within a zone having a grade A (air speed approximately 0.2-0.4 m/s) environment within a pharmaceutical production facility, washed and dried vials were filled with 0.56 g of this PTH peptide-containing aqueous solution, and partially open vials were obtained using washed and dried rubber stoppers. The partially open vials were transferred to a grade A zone, and all were sequentially loaded over approximately three hours into a freeze-drying chamber having a small door (Kyowa Vacuum Engineering Co., Ltd. (model: RL, tray area: 9 m$^2$)). The solution containing PTH peptide was frozen and freeze dried to sublimate off the water under reduced pressure. After the interiors of the glass vials were purged with nitrogen once drying had been completed, the vials were sealed with the rubber stoppers, capped with aluminum caps, and a freeze-dried preparation containing PTH peptide was obtained.

Test Example 1

The area percentage method using HPLC is a simple method for assessing the purity of a freeze-dried preparation containing PTH peptide and the amount of analogs. A solution obtained by weighing out 0.25 g of benzalkonium chloride and bringing it to 50 mL by adding 50 mM sulfate buffer (pH 2.3) serves as the loading buffer. Each preparation of the examples and comparative examples is dissolved by 1 mL of physiological saline solution, and a 9:1 mixture of this solution and the loading buffer serves as the sample solution. A quantity of 100 µL of sample solution is tested by HPLC under the following conditions. Furthermore, benzalkonium chloride was used to prevent the peptide that is the target of measurement from attaching to the instrument and the like.

<Test Conditions>

Detector: Ultraviolet absorptiometer (measurement wavelength: 214 nm)

Column: Stainless steel tube 150 mm long having an inner diameter of 4.6 mm packed with 3.5 µm of octadecylsilylated silica gel Column temperature: Constant temperature near 40° C.

Mobile phase: Mobile phase A: Dissolve 28.4 g of anhydrous sodium sulfate in 900 mL of water and bring to 1000 mL by adding water after adding phosphoric acid to adjust the pH to 2.3. Add 100 mL of acetonitrile to this 900 mL of liquid.

Mobile phase B: Dissolve 28.4 g of anhydrous sodium sulfate in 900 mL of water and bring to 1000 mL by adding water after adding phosphoric acid to adjust the pH to 2.3 Add 500 mL of acetonitrile to 500 mL of this liquid.

Mobile phase feed: Concentration gradient control is provided by varying the mixture ratio of mobile phase A and mobile phase B as follows.

Time after injection:

TABLE 5

| Concentration gradient control | | |
|---|---|---|
| Time after sample injection (min) | Mobile phase A (vol %) | Mobile phase B (vol %) |
| 0-5 | 100→65 | 0→35 |
| 5-35 | 65→60 | 35→40 |
| 35-45 | 60→0 | 40→100 |

Flow rate: 1.0 mL/min

Sample temperature: Constant temperature near 5° C.

Detection time: 45 minutes after injection of the sample solution. However, this is from the back of the solvent peak.

Calculation method: The amount of each PTH analog and the total amount thereof was determined by performing liquid chromatography under the above conditions, measuring each peak area by automatic integration, and performing calculation using Formulas 1 and 2. Furthermore, the total peak area was the sum total of the area of all peaks detected by performing liquid chromatography under the above conditions. In other words, the total peak area shows the sum total of PTH peptide and all PTH analogs in the preparation.

Amount of each PTH analog (%)=(peak area of each analog/total peak area)×100    Formula 1:

Total amount of PTH analogs (%)=(sum total of peak areas of each analog/total peak area)×100    Formula 2:

<Results>

Figure 2:
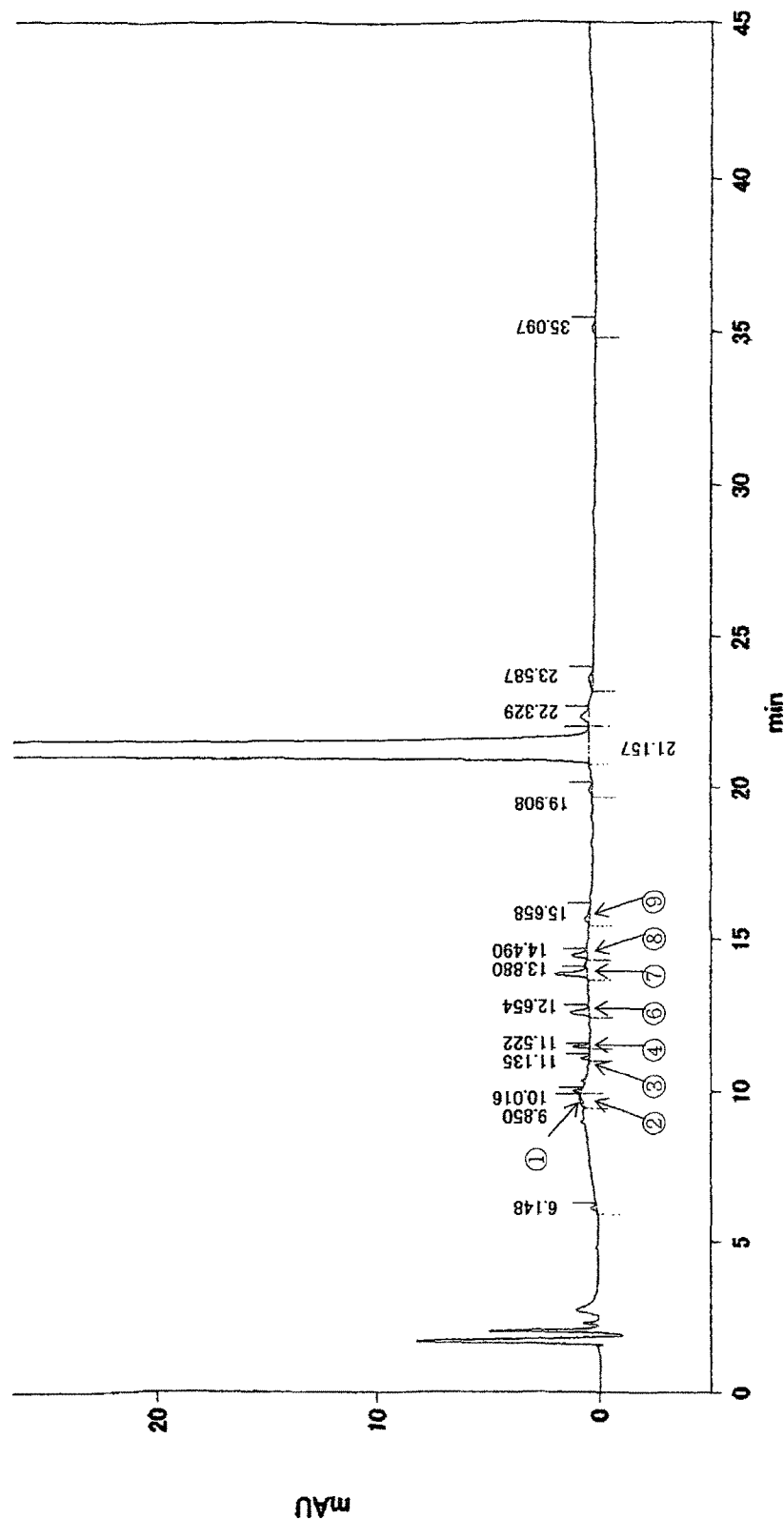
FIG. 2 shows the chromatogram when the ultraviolet (214 nm) absorbance was measured by high-performance liquid chromatography (HPLC) taking as the sample a PTH peptide freeze-dried preparation produced as Example 1. The horizontal axis represents the time (min), and the vertical axis represents the absorption intensity. The large peak appearing at 21.157 min (retention time) is human PTH (1-34). "1 (encircled number)" corresponds to analog 1'; "2 (encircled number)" corresponds to analog 2'; "3 (encircled number)" corresponds to a mixture of analog 3' and analog 4'; "4 (encircled number)" corresponds to analog 5'; "6 (encircled number)" corresponds to analog 7'; "7 (encircled number)" corresponds to analog 8'; "8 (encircled number)" corresponds to analog 9'; "9 (encircled number)" corresponds to a mixture of analog 10' and mixture 11'.
Figure 3:
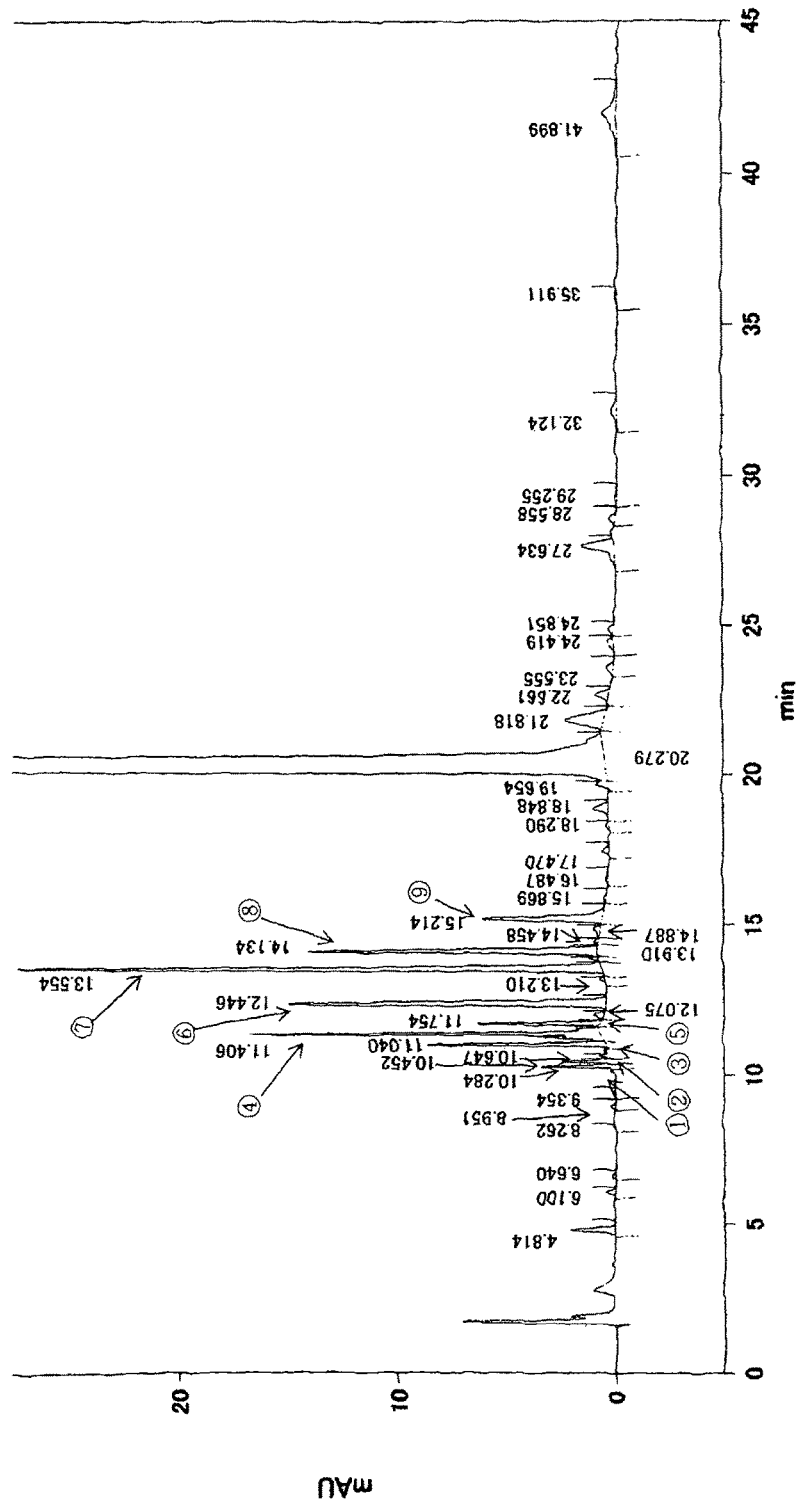
FIG. 3 shows the chromatogram when the ultraviolet (214 nm) absorbance was measured by high-performance liquid chromatography (HPLC) taking as the sample a PTH peptide freeze-dried preparation produced as Comparative Example 1. The horizontal axis represents the time (min), and the vertical axis represents the absorption intensity. The large peak appearing at 20.279 min (retention time) is human PTH (1-34). "5 (encircled number)" corresponds to analog 6'; the meaning of the other encircled numbers is the same as in FIG. 2.

Table 6 shows the results obtained by assessing the amount of analogs of the human PTH (1-34) (bulk drug) used in the examples. FIG. 1 shows an HPLC chart. Table 7 shows the results obtained by assessing the purity of the freeze-dried preparations containing PTH peptide and the amount of analogs in the test example. FIG. 2 shows an HPLC chart of Example 1, and FIG. 3 shows an HPLC chart of Comparative Example 1. The structure of each analog in Table 6 was obtained by estimation using Test Example 2 below.

TABLE 6

| Amount of each analog (%) in human PTH (1-34) used as a bulk drug | | | | | | | | |
|---|---|---|---|---|---|---|---|---|
| | A | B | C | D | E | F | G | H |
| Use in examples and comparative examples | Ex. 1 | Ex. 1 | Ex. 1, 4 | Ex. 2, CEx 2 | Ex. 4 | CEx 1 | CEx 1 | Ex. 5 |
| (1) Human PTH (1-34)-Met 8 [O]-Met 18 [O]-Trp 23 [dioxidation] | ND | ND | ND | ND | ND | ND | ND | ND |
| (2) Human PTH (1-34)-Met 8 [O]-Met 18 [O]-Trp 23 [dioxidation-formic acid elimination] | ND | ND | ND | ND | ND | ND | ND | ND |
| (3) Mixture containing human PTH (1-34)-Met 8 [O]-Met 18 [O] and human PTH (1-34)-Met 8 [O]-Trp 23 [dioxidation] | ND | ND | ND | ND | ND | ND | ND | ND |

TABLE 6-continued

Amount of each analog (%) in human PTH (1-34) used as a bulk drug

|  | A | B | C | D | E | F | G | H |
|---|---|---|---|---|---|---|---|---|
| (4) Human PTH (1-34)-Met 18 [O]-Trp 23 [dioxidation] | ND | ND | ND | ND | ND | ND | ND | ND |
| (5) Human PTH (1-34)-Met 18 [O]-Trp 23 [dioxidation-formic acid elimination] | ND | ND | ND | ND | ND | ND | ND | ND |
| (6) Human PTH (1-34)-Met 8 [O] | 0.08 | 0.07 | 0.11 | 0.05 | 0.05 | 0.14 | 0.17 | 0.06 |
| (7) Human PTH (1-34)-Met 18 [O] | 0.13 | 0.09 | 0.16 | 0.06 | 0.07 | 0.21 | 0.23 | 0.09 |
| (8) Human PTH (1-34)-Trp 23 [dioxidation] | ND | ND | ND | ND | ND | ND | ND | ND |
| (9) Mixture containing human PTH (1-34)-Trp 23 [monoxidation] and human PTH (1-34)-Trp 23 [dioxidation-formic acid elimination] | ND | ND | ND | ND | ND | ND | ND | ND |

Ex.: Example;
CEx.: Comparative Example

TABLE 7

Total amount of analogs (total amount) and amount of each analog (%)

|  | Ex. 1 | Ex. 2 | Ex. 3 | Ex. 4 | Ex. 5 | CEx. 1 | CEx. 2 |
|---|---|---|---|---|---|---|---|
| Total amount (%) | 0.88 | 0.76 | 1.51 | 0.95 | 0.72 | 6.27 | 3.09 |
| (1) Human PTH (1-34)-Met 8 [O]-Met 18 [O]-Trp 23 [dioxidation] | 0.03 | ND | ND | ND | ND | 0.10 | 0.05 |
| (2) Human PTH (1-34)-Met 8 [O]-Met 18 [O]-Trp 23 [dioxidation-formic acid elimination] | 0.02 | ND | ND | ND | ND | 0.07 | ND |
| (3) Mixture containing human PTH (1-34)-Met 8 [O]-Met 18 [O] and human PTH (1-34)-Met 8 [O]-Trp 23 [dioxidation] | 0.03 | ND | ND | 0.03 | 0.03 | 0.29 | 0.12 |
| (4) Human PTH (1-34)-Met 18 [O]-Trp 23 [dioxidation] | 0.06 | 0.02 | 0.03 | 0.05 | ND | 0.69 | 0.27 |
| (5) Human PTH (1-34)-Met 18 [O]-Trp 23 [dioxidation-formic acid elimination] | ND | ND | 0.03 | ND | ND | 0.19 | ND |
| (6) Human PTH (1-34)-Met 8 [O] | 0.14 | 0.09 | 0.24 | 0.15 | 0.09 | 0.93 | 0.34 |
| (7) Human PTH (1-34)-Met 18 [O] | 0.19 | 0.15 | 0.36 | 0.25 | 0.10 | 1.42 | 1.08 |
| (8) Human PTH (1-34)-Trp 23 [dioxidation] | 0.09 | 0.04 | 0.10 | 0.11 | 0.04 | 0.74 | 0.69 |
| (9) Mixture containing human PTH (1-34)-Trp 23 [monoxidation] and human PTH (1-34)-Trp 23 [dioxidation-formic acid elimination] | 0.05 | ND | 0.09 | 0.04 | 0.02 | 0.40 | 0.08 |

Ex.: Example;
CEx.: Comparative Example

Test Example 2

Human PTH (1-34) analogs were produced and fractionated, and the fractions were analyzed to estimate the structures of each analog obtained in Test Example 1.

(1) Production and Fractionation of Each Analog

A quantity of 4.00 g of sucrose and 0.20 g of sodium chloride were weighed out and dissolved by adding water for injection to make a placebo solution. Human PTH (1-34) was weighed out exactly and dissolved by adding 100 mL of placebo solution to make a reaction stock solution. An environment having an ozone concentration of approximately 0.08 ppm by ozone concentration meter was produced using an ozone generator and a blower (initial wind speed approximately 7.2 m/s) to circulate the ozone and make the concentration uniform in a tray having a 40 cm long×90 cm wide×100 cm high glass door. Approximately 15 mL of the reaction stock solution was dispensed into each 20 mL vial. A stirrer was introduced into the vial, and degradation was carried out while stirring by stirrer until the purity was approximately 20% (in other words, the total amount of human PTH (1-34) analogs was 80%) by exposure (for about 20 hours) to an ozone atmosphere of approximately 0.08 ppm. Furthermore, the purity was confirmed in accordance with the test conditions of Test Example 1. The degraded solution was freeze dried, and a solution dissolved by a suitable amount of water for injection was taken as a forced-degradation solution. The analogs were fractionated under the following conditions using this solution.

<Test Conditions>

The test conditions other than the following were the same as the test conditions in Test Example 1.

<Conditions Different from Test Example 1>

Column: Stainless steel tube 250 mm long having an inner diameter of 9.4 mm packed with 5 μm of octadecylsilylated silica gel Flow rate: 6.0 mL/min Furthermore, no major differences in the chromatogram pattern were observed despite the fact that the above conditions differed from those of Test Example 1.

Nine analogs were fractionated under the above chromatography conditions. They were desalted and concentrated, and the freeze-dried products were dissolved in distilled water to obtain each analog (undigested compound). Each analog (undigested compound) and the forced-degradation solution were analyzed by HPLC under the test conditions of Test Example 1, and the relative retention time of each analog (undigested compound) was calculated, taking the retention time of human PTH (1-34) in the forced-degradation solution as 1.

<Results>

Figure 4:
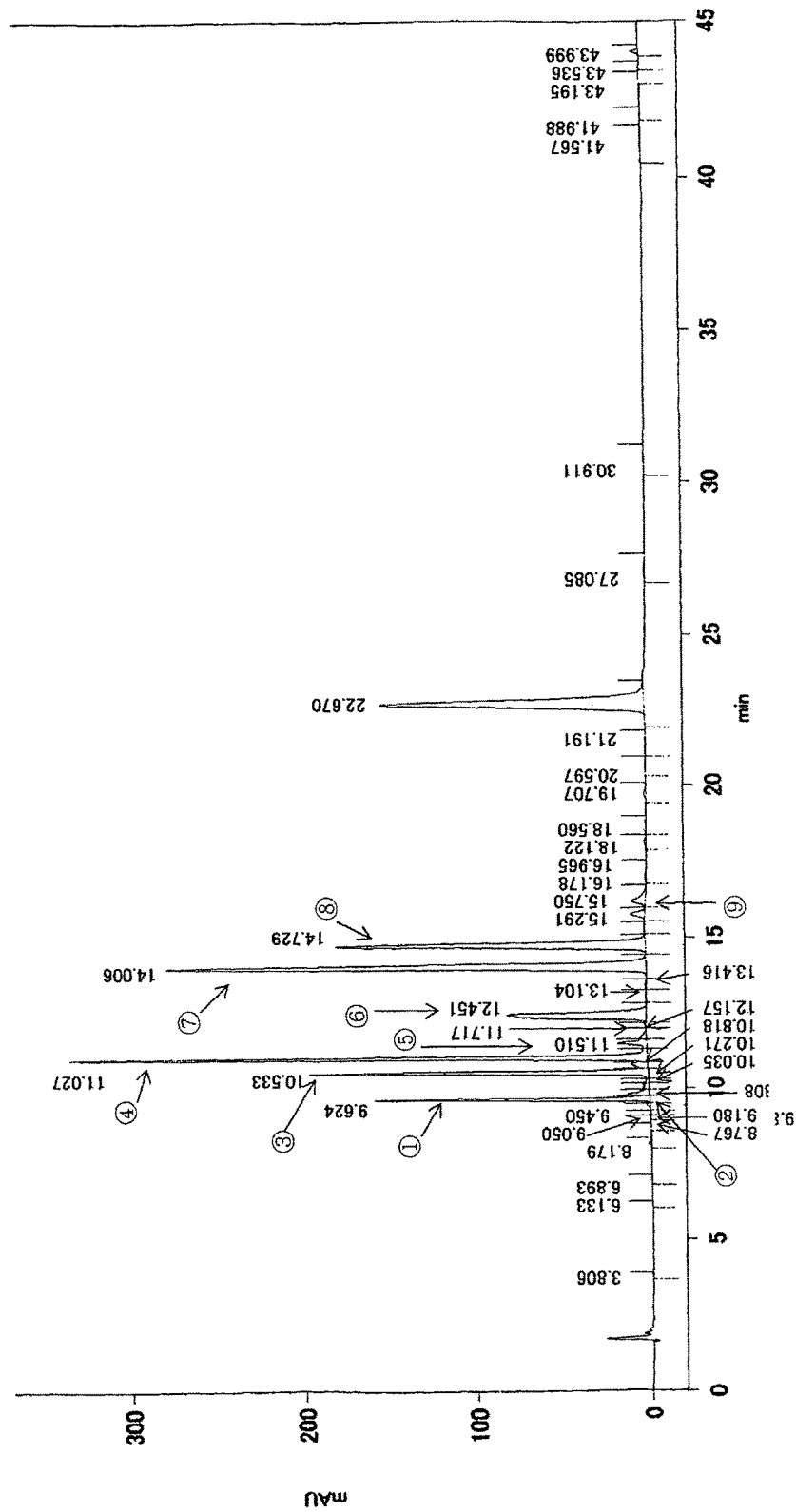
FIG. 4 shows the chromatogram when the ultraviolet (214 nm) absorbance was measured by high-performance liquid chromatography (HPLC) taking as the sample a PTH peptide freeze-dried preparation exposed to ozone as in Test Example 2. The horizontal axis represents the time (min), and the vertical axis represents the absorption intensity. The large peak appearing at 22.670 min (retention time) is human PTH (1-34). The meaning of the encircled numbers is the same as in FIG. 2.

Basically complete agreement with the relative retention time of each analog in the forced-degradation solution was confirmed. Table 8 shows the results on the relative retention times. FIG. 4 shows a chromatogram of the forced-degradation solution. The elution times of the human PTH (1-34) peaks differ slightly owing to the differing compositions of the charged solutions in FIGS. 3 and 4, but the corresponding analogs of FIGS. 3 and 4 were assumed to be the same given that the elution patterns and weight percent of each analog were the same on each chart. Based on these results, the ozone exposure test here appeared to be a test that substantially reproduces the PTH analog production reactions triggered when solution containing PTH peptide is produced in an air environment inside a pharmaceutical production facility.

TABLE 8

Comparison of the relative retention time of the relevant peaks of analogs (undigested compounds) and forced-degradation solution

| | Analog (undigested compound) | Forced-degradation solution |
|---|---|---|
| Human PTH (1-34) | — | 1.00 |
| Analog (1) | 0.43 | 0.42 |
| Analog (2) | 0.44 | 0.43 |
| Analog (3) | 0.46 | 0.46 |
| Analog (4) | 0.49 | 0.49 |
| Analog (5) | 0.51 | 0.51 |
| Analog (6) | 0.55 | 0.55 |
| Analog (7) | 0.62 | 0.62 |
| Analog (8) | 0.65 | 0.65 |
| Analog (9) | 0.70 | 0.70 |

(2) Structural Estimation Analysis of Each Analog

Each of the above analogs (undigested compounds) and human PTH (1-34) standard were digested by trypsin to produce analogs (digested compounds) and standard solution (digested compound). Ten of these samples were analyzed by LC/MS/MS under the following conditions.

<LC/MS/MS Conditions>

Detector: Ultraviolet absorptiometer (measurement wavelength: 210 nm)

Column: Stainless steel tube 150 mm long having an inner diameter of 1.5 mm packed with 5 μm of octadecylsilylated silica gel Column temperature: Constant temperature near 40° C.

Mobile phase: Mobile phase A: Mixed aqueous solution containing trifluoroacetic acid (1:1000)

Mobile phase B: Acetonitrile

Mobile phase feed: Concentration gradient control is provided by varying the mixture ratio of mobile phase A and mobile phase B as follows.

Time after injection:

TABLE 9

| Concentration gradient control | | |
|---|---|---|
| Time after sample injection (min) | Mobile phase A (vol %) | Mobile phase B (vol %) |
| 0-30 | 95→55 | 5→45 |
| 30-40 | 55 | 45 |

Flow rate: 0.1 mL/min

Sample temperature: Constant temperature near 5° C.

Detection time: 45 minutes after injection of the sample solution. However, this is from the back of the solvent peak Ionization Mode: ES+

Each analog (undigested compound) was analyzed by LC/MS under the following conditions.

<LC/MS Test Conditions>

Conditions other than the following were the same as the LC/MS/MS conditions.

Mobile phase feed: Concentration gradient control is provided by varying the mixture ratio of mobile phase A and mobile phase B as follows.

Time after injection:

TABLE 10

| Concentration gradient control | | |
|---|---|---|
| Time after sample injection (min) | Mobile phase A (vol %) | Mobile phase B (vol %) |
| 0-30 | 85→55 | 15→45 |
| 30-40 | 55 | 45 |

<Results>

The results of structural analysis of the nine analogs in Test Example 2 were as follows.

<Human PTH (1-34)>

Table 11 shows the expected fragments of human PTH (1-34) produced by trypsin digestion.

TABLE 11

| Expected fragments of human PTH (1-34) | | |
|---|---|---|
| Fragment No. | Estimated structure | Amino acid sequence |
| T1 | PTH (1-13) | Ser-Val-Ser-Glu-Ile-Gln-Leu-Met-His-Asn-Leu-Gly-Lys SEQ ID NO: 1 |
| T2 | PTH (14-20) | His-Leu-Asn-Ser-Met-Glu-Arg SEQ ID NO: 2 |
| T3 | PTH (21-25) | Val-Glu-Trp-Leu-Arg SEQ ID NO: 3 |
| T4 | PTH (26) | Lys |
| T5 | PTH (27) | Lys |
| T6 | PTH (28-34) | Leu-Gln-Asp-Val-His-Asn-Phe SEQ ID NO: 5 |

Table 12 shows the results of measurement of the mass of each fragment confirmed in LC/MS/MS of the standard solution (digested compound). The measured values of each fragment in the standard solution (digested compound) were compared with the calculated mass, and it was confirmed that five fragments of estimated structure were obtained in human PTH (1-34).

TABLE 12

Results of mass measurement of standard solution (digested compound)

| Retention time | Measured mass Mass (mono.) | Calculated mass Mass (mono.) | Estimated structure | Fragment No. |
|---|---|---|---|---|
| 13.423 | 885.4984 | 885.4127 | PTH (14-20) | T2 |
| 18.371 | 871.5030 | 871.4188 | PTH (28-34) | T6 |
| 18.371 | 999.6100 | 999.5138 | PTH (27-34) | T5-6 |
| 21.222 | 701.4508 | 701.3861 | PTH (21-25) | T3 |
| 22.618 | 1454.8715 | 1454.7551 | PTH (1-13) | T1 |

<Analog 1>

The analog showing a retention time=0.43 in the column "Analogs (undigested compounds)" in Table 8 was taken as analog 1, and Table 13 shows the results of mass measurement in LC/MS/MS of analog 1 (digested compound). Changes in mass of +16 Da in T2, +4 Da in T3, and +16 Da in T1 were confirmed in analog 1 (digested compound) by comparison with the measured values of the relevant fragments in the standard solution (digested compound).

TABLE 13

Results of mass measurement of analog 1 (digested compound)

| Retention time | Analog 1 | Standard solution | | Difference in mass |
|---|---|---|---|---|
| (min) | Mass (mono.) | Frag. No. | Mass (mono.) | (F = 0, 4/5) |
| 9.578 | 901.4622 | T2 | 885.4984 | +16 Da |
| 18.409 | 871.4731 | T6 | 871.5030 | 0 |
| 18.409 | 999.5720 | T5-6 | 999.6100 | 0 |
| 19.096 | 705.4228 | T3 | 701.4508 | +4 Da |
| 19.323 | 1470.8297 | T1 | 1454.8715 | +16 Da |

Table 14 shows the results obtained by MS/MS analysis of fragments confirmed to have changes in mass. As a result of comparison with the standard solution (digested compound), changes in mass of +16 Da in Met 18 in T2, +4 Da in Trp 23 in T3, and +16 Da in Met 8 in T1 were confirmed.

TABLE 14

Results of MS/MS analysis of analog 1 (digested compound)

| Frag-ment No. | Mass observed on MS/MS spectrum | | Estimated structure | Amino acid with change in mass |
|---|---|---|---|---|
| | Analog 1 (mono.) | Standard solution (mono.) | | |
| T2 | 304.1896 | 304.1960 | PTH (19-20) | Met 18 +16 Da |
| | 434.2278 | — | PTH (18-20) +16 Da | |
| | — | 418.2120 | PTH (18-20) | |
| T3 | 271.2070 | 271.2085 | PTH (24-25) | Trp 23 +4 Da |
| | 478.2979 | — | PTH (23-25) +4 Da | |
| | — | 474.3203 | PTH (23-25) | |
| T1 | 568.3508 | 568.3636 | PTH (9-13) | Met 8 +16 Da |
| | 715.3823 | — | PTH (8-13) +16 Da | |
| | — | 699.4180 | PTH (8-13) | |

Figure 7:
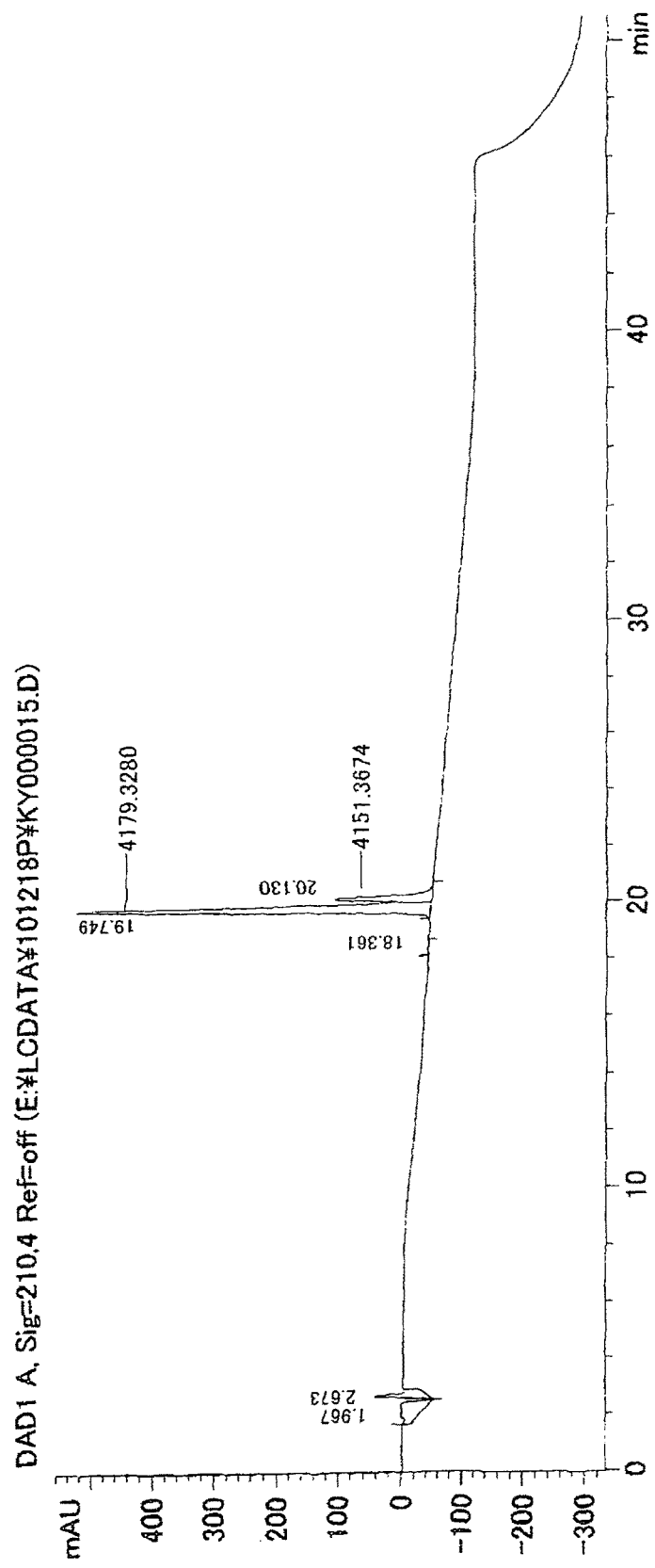
FIG. 7 shows the results of high-performance liquid chromatography-mass spectrometry (LC/MS) of analog 1. The horizontal axis represents the time (min), and the vertical axis represents the detection intensity.

Table 15 shows the results obtained by comparing the mass of analog 1 (undigested compound) obtained by LC/MS with the calculated value of 4115.1309 of human PTH (1-34). In analog 1 (undigested compound) peaks of +64 Da and +36 Da were confirmed in comparison to the calculated mass, and the +64 Da peak appeared to be the main peak based on the size of the peaks, as shown in FIG. 7. The molecular weight of the undigested compound is approximately 4000 Da, but since the mass of a multivalent ion is obtained as the measured value in LC/MS, an error of about ±1 Da was anticipated in the process of calculating the mass of the undigested compound from the mass of the multivalent ion. Corrected values are listed in parentheses for estimated differences in mass when an error arose in structural analysis. The same is true in subsequent structural analyses.

TABLE 15

Results of mass measurement of analog 1 (undigested compound)

| Retention time (min) | Measured mass Mass (mono.) | Calculated mass Mass (mono.) | Difference in mass (F = 0, 4/5) |
|---|---|---|---|
| 19.749 | 4179.3280 | 4115.1309 | +64 Da |
| 20.130 | 4151.3674 | 4115.1309 | +36 Da |

Based on the results of MS/MS analysis, it was estimated that human PTH (1-34) +36 Da=(Met 18+16 Da)+(Trp 23+4 Da)+(Met 8+16 Da). The structure of the +4 Da changed form in Trp is b) in FIG. 6, and the change in mass of its precursor a) was expected to be +32 Da. Trp 23 was assumed to have changed from a) to b) in the course of trypsin digestion and other such procedures, and the main peak of analog 1 (undigested compound) was estimated to be human PTH (1-34) +64 Da=(Met 18+16 Da)+(Trp 23+32 Da)+(Met 8+16 Da). In other words, analog 1 was estimated to be human PTH (1-34)-Met 8 [O]-Met 18 [O]-Trp 23 [dioxidation].

<Analog 2>

The analog showing a retention time=0.44 in the column "Analogs (undigested compounds)" in Table 8 was taken as analog 2, and Table 16 shows the results of mass measurement in LC/MS/MS of analog 2 (digested compound). Changes in mass of +16 Da in T2, +4 Da in T3, and +16 Da in T1 were confirmed in analog 2 (digested compound) by comparison with the measured values of the relevant fragments in the standard solution (digested compound).

TABLE 16

Results of mass measurement of analog 2 (digested compound)

| Retention time | Analog 2 | Standard solution | | Difference in mass |
|---|---|---|---|---|
| (min) | Mass (mono.) | Frag. No. | Mass (mono.) | (F = 0, 4/5) |
| 9.58 | 901.4695 | T2 | 885.4984 | +16 Da |
| 18.348 | 871.4788 | T6 | 871.5030 | 0 |
| 18.348 | 999.5874 | T5-6 | 999.6100 | 0 |
| 19.059 | 705.4333 | T3 | 701.4508 | +4 Da |
| 19.222 | 1470.8492 | T1 | 1454.8715 | +16 Da |

Figure 8:
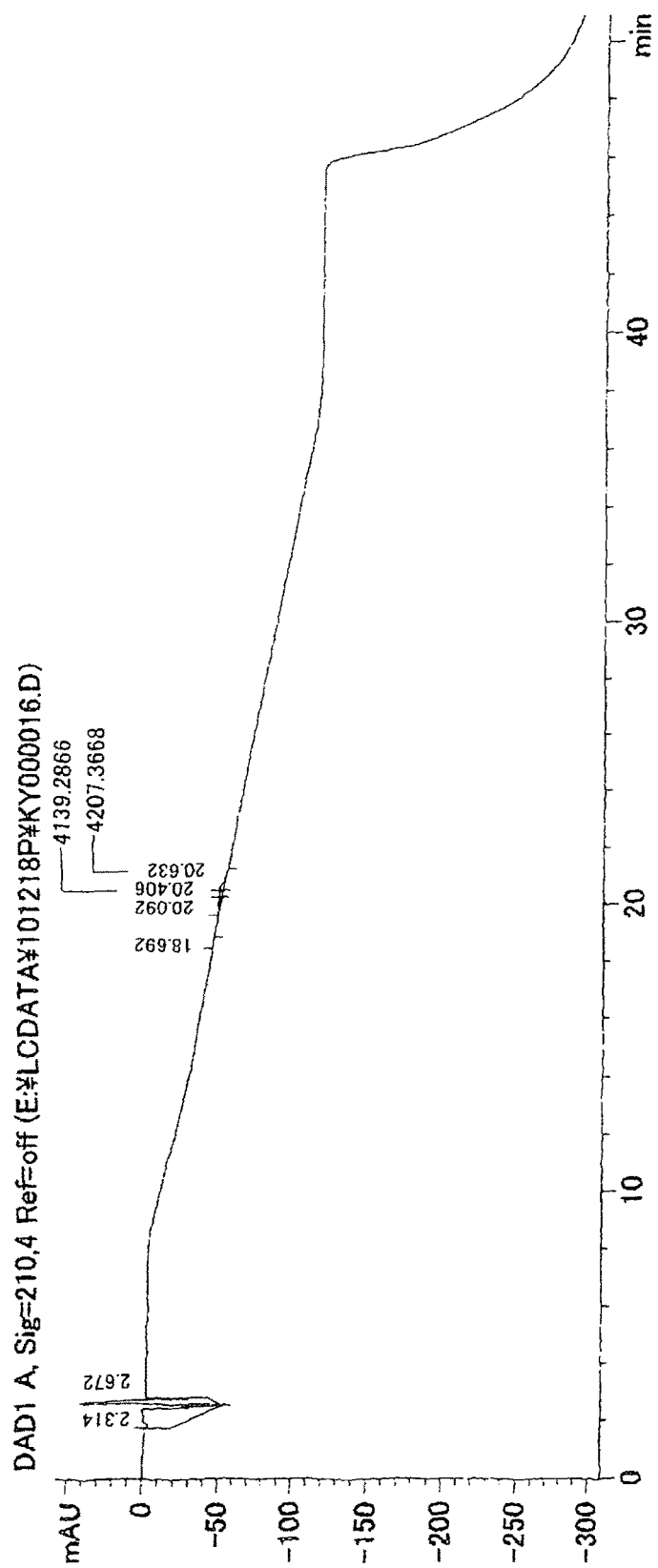
FIG. 8 shows the results of high-performance liquid chromatography-mass spectrometry (LC/MS) of analog 2. The horizontal axis represents the time (min), and the vertical axis represents the detection intensity.

Changes in mass of +16 Da in Met 18 in T2, +4 Da in Trp 23 in T3, and +16 Da in Met 8 in T1 were confirmed, in the same way as in analog 1, as a result of MS/MS analysis of fragments confirmed to have changes in mass. Table 17 shows the results of comparing the mass of analog 2 (undigested compound) obtained by LC/MS with the calculated mass of 4115.1309 of human PTH (1-34). In analog 2 (undigested compound), peaks of +24 Da and +92 Da were confirmed in comparison to the calculated masses, but the reliability of these confirmed masses appeared to be low since basically no peak shape was formed, as shown in FIG. 8, and no masses supporting the results of MS/MS analysis could be obtained.

TABLE 17

Results of mass measurement of analog 2 (undigested compound)

| Retention time (min) | Measured mass Mass (mono.) | Calculated mass Mass (mono.) | Difference in mass (F = 0, 4/5) |
|---|---|---|---|
| 20.092 | 4139.2866 | 4115.1309 | +24 Da |
| 20.632 | 4207.3668 | 4115.1309 | +92 Da |

Based on the results of MS/MS analysis, analog 2 was estimated to have undergone at least changes in mass of human PTH (1-34) +36 Da=(Met 18+16 Da)+(Trp 23+4 Da)+(Met 8+16 Da). In other words, analog 2 was estimated to be human PTH (1-34)-Met 8 [O]-Met 18 [O]-Trp 23 [dioxidation-formic acid elimination].

<Analogs 3 and 4>

The peak showing a retention time=0.46 in the column "Analogs (undigested compounds)" in Table 8 was derived from a mixture of analogs 3 and 4, as explained below. Table 18 shows the results of mass measurement in LC/MS/MS of a mixture of analogs 3 and 4 (digested compound). Changes in mass of +16 Da in T2, +4 Da in T3, and +16 Da in T1 were confirmed in the mixture of analogs 3 and 4 (digested compound) by comparison with the measured values of the relevant fragments in the standard solution (digested compound). T2 and T3 fragments not associated with changes in mass were also confirmed.

TABLE 18

Results of mass measurement of a mixture of analogs 3 and 4 (digested compound)

| Retention time (min) | Analog 3 Mass (mono.) | Standard solution Frag. No. | Standard solution Mass (mono.) | Difference in mass (F = 0, 4/5) |
|---|---|---|---|---|
| 9.813 | 901.4778 | T2 | 885.4984 | +16 Da |
| 13.475 | 885.4846 | T2 | 885.4984 | 0 |
| 18.326 | 871.4844 | T6 | 871.5030 | 0 |
| 18.326 | 999.5800 | T5-6 | 999.6100 | 0 |
| 18.959 | 705.4266 | T3 | 701.4508 | +4 Da |
| 19.223 | 1470.8373 | T1 | 1454.8715 | +16 Da |
| 21.195 | 701.4322 | T3 | 701.4508 | 0 |

Figure 9:
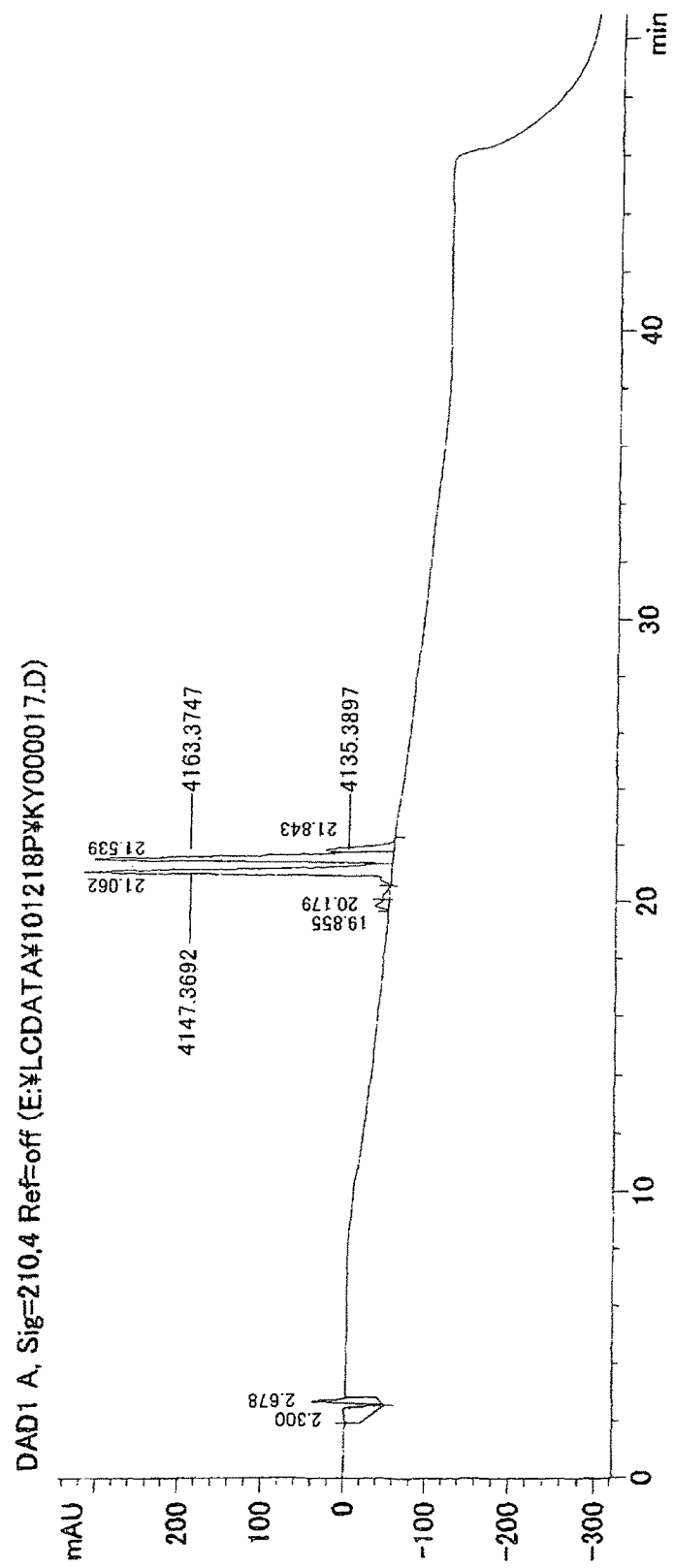
FIG. 9 shows the results of high-performance liquid chromatography-mass spectrometry (LC/MS) of a mixture of analog 3 and analog 4. The horizontal axis represents the time (min), and the vertical axis represents the detection intensity.

Changes in mass of +16 Da in Met 18 in T2, +4 Da in Trp 23 in T3, and +16 Da in Met 8 in T1 were confirmed, in the same way as in analog 1, as a result of MS/MS analysis of fragments confirmed to have changes in mass. Table 19 shows the results of comparing the mass of a mixture of analogs 3 and 4 (undigested compound) obtained by LC/MS with the calculated mass of 4115.1309 of human PTH (1-34). In the mixture of analogs 3 and 4 (undigested compound), peaks of +32 Da, +48 Da, and +20 Da were confirmed in comparison to the calculated masses, and +32 Da and +48 Da in an approximate ratio of 1:1 appeared to be the main peak based on the size of the peaks, as shown in FIG. 9.

TABLE 19

Results of mass measurement of a mixture of analogs 3 and 4 (undigested compound)

| Retention time (min) | Measured mass Mass (mono.) | Calculated mass Mass (mono.) | Difference in mass (F = 0, 4/5) |
|---|---|---|---|
| 21.062 | 4147.3692 | 4115.1309 | +32 Da |
| 21.539 | 4163.3747 | 4115.1309 | +48 Da |
| 21.843 | 4135.3897 | 4115.1309 | +20 Da |

On the LC/MS/MS chromatogram of a mixture of analogs 3 and 4 (digested compound), T2+16 Da: T2 and T3+4 Da: T3 were each present in an approximately 1:1 ratio, and T2+16 Da: T3+4 Da: T1+16 Da were present in an approximately 1:1:2 ratio. Based on the results of MS/MS analysis, it was estimated that human PTH (1-34) +32 Da=(Met 18+16 Da)+(Met 8+16 Da) and human PTH (1-34) +20 Da=(Trp 23+4 Da)+(Met 8+16 Da). With regard to the latter, Trp 23 was assumed to have undergone a change of a) to b) in the course of trypsin digestion and other such procedures, in the same way as analog 1, and it was estimated that human PTH (1-34) +48 Da=(Trp 23+32 Da)+(Met 8+16 Da). Analogs 3 and 4 were estimated to be human PTH (1-34) +32 Da and human PTH (1-34) +48 Da, respectively. In other words, the peak having a relative retention time=0.46 in Table 8 was estimated to be a peak of a mixture containing human PTH (1-34)-Met 8 [O]-Met 18 [O] and human PTH (1-34)-Met 8 [O]-Trp 23 [dioxidation].

<Analog 5>

The analog showing a retention time=0.49 in the column "Analogs (undigested compounds)" in Table 8 was taken as analog 5, and Table 20 shows the results of mass measurement in LC/MS/MS of analog 5 (digested compound). Changes in mass of +16 Da in T2 and +4 Da in T3 were confirmed in analog 5 (digested compound) by comparison with the measured values of the relevant fragments in the standard solution (digested compound).

TABLE 20

Results of mass measurement of analog 5 (digested compound)

| Retention time (min) | Analog 4 [sic] Mass (mono.) | Standard solution Frag. No. | Standard solution Mass (mono.) | Difference in mass (F = 0, 4/5) |
|---|---|---|---|---|
| 9.587 | 901.4664 | T2 | 885.4984 | +16 Da |
| 18.321 | 871.4904 | T6 | 871.5030 | 0 |
| 18.321 | 999.5957 | T5-6 | 999.6100 | 0 |
| 19.012 | 705.4388 | T3 | 701.4508 | +4 Da |
| 22.561 | 1454.8492 | T1 | 1454.8715 | 0 |

Figure 10:
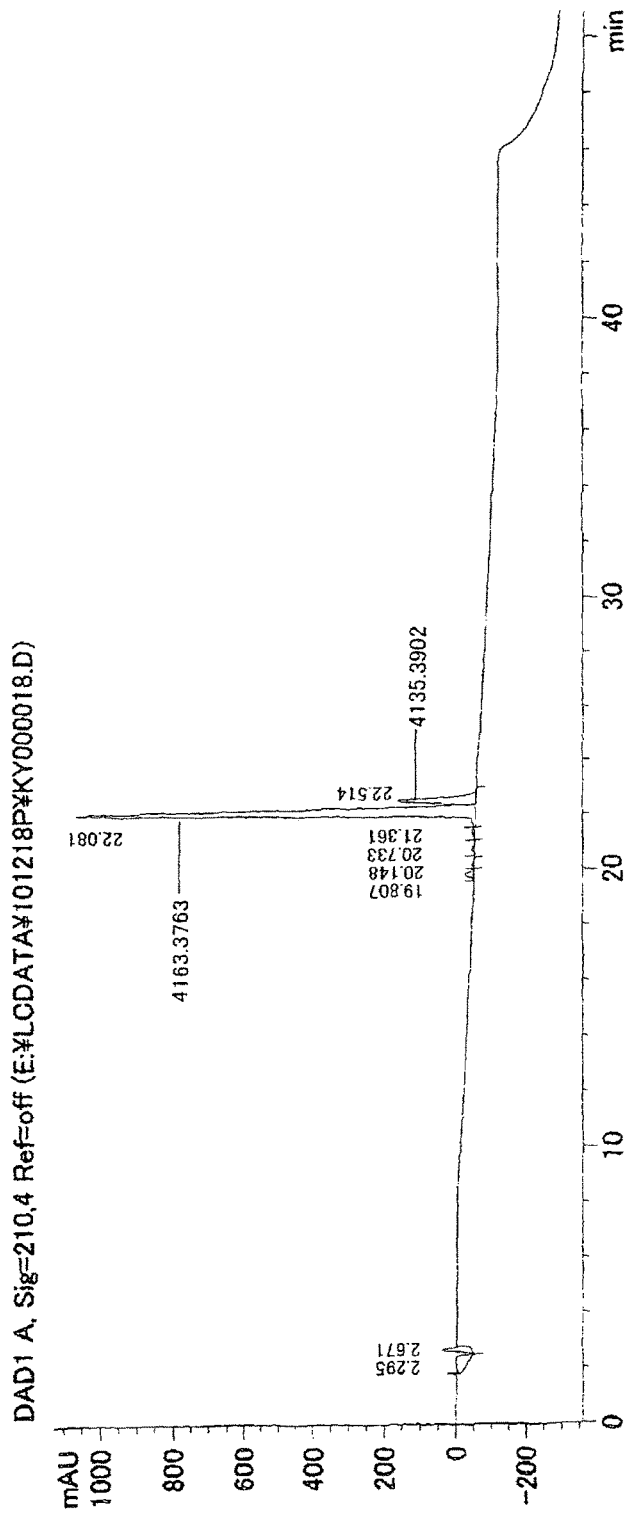
FIG. 10 shows the results of high-performance liquid chromatography-mass spectrometry (LC/MS) of analog 5. The horizontal axis represents the time (min), and the vertical axis represents the detection intensity.
Figure 11:
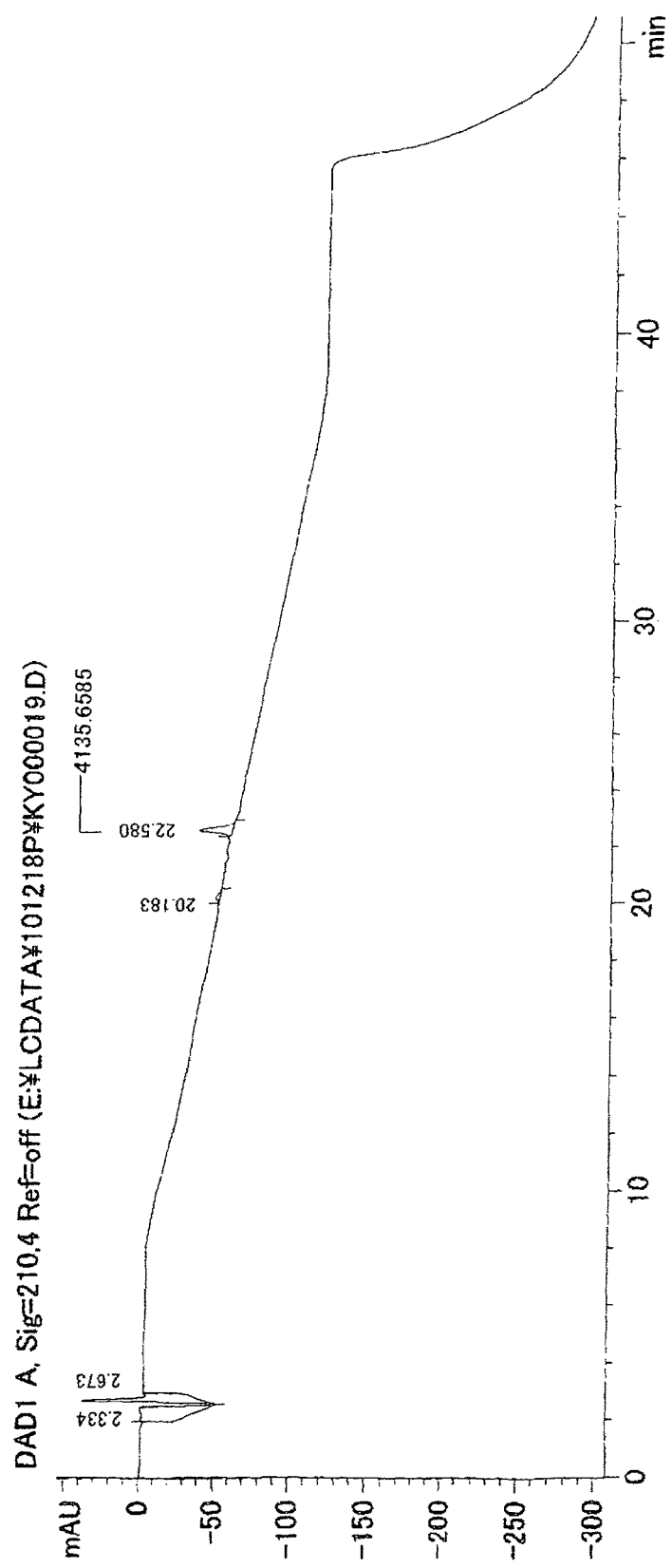
FIG. 11 shows the results of high-performance liquid chromatography-mass spectrometry (LC/MS) of analog 6. The horizontal axis represents the time (min), and the vertical axis represents the detection intensity.
Figure 12:
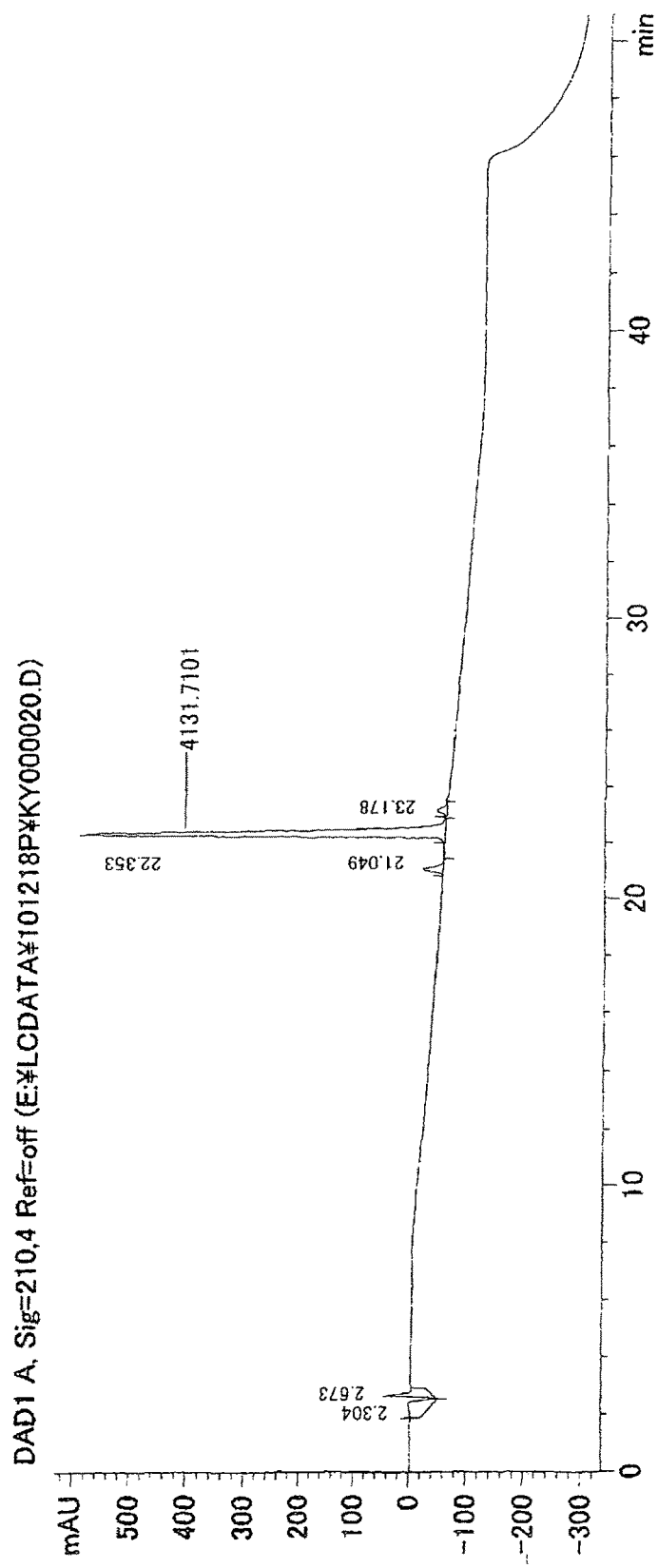
FIG. 12 shows the results of high-performance liquid chromatography-mass spectrometry (LC/MS) of analog 7. The horizontal axis represents the time (min), and the vertical axis represents the detection intensity.

Changes in mass of +16 Da in Met 18 in T2 and +4 Da in Trp 23 in T3 were confirmed, in the same way as in analog 1, as a result of MS/MS analysis of fragments confirmed to have changes in mass. Table 21 shows the results of comparing the mass of analog 5 (undigested compound) obtained by LC/MS with the calculated mass of 4115.1309 of human PTH (1-34). In analog 5 (undigested compound), peaks of +48 Da and +20 Da were confirmed in comparison to the calculated masses, and +48 Da appeared to be the main peak based on the size of the peaks, as shown in FIG. 10.

TABLE 21

Results of mass measurement of analog 5 (undigested compound)

| Retention time (min) | Measured mass Mass (mono.) | Calculated mass Mass (mono.) | Difference in mass (F = 0, 4/5) |
|---|---|---|---|
| 22.081 | 4163.3763 | 4115.1309 | +48 Da |
| 22.514 | 4135.3902 | 4115.1309 | +20 Da |

Based on the results of MS/MS analysis, it was estimated that human PTH (1-34) +20 Da=(Met 18+16 Da)+(Trp 23+4 Da). Trp 23 was assumed to have undergone a change of a) to b) in the course of trypsin digestion and other such procedures, in the same way as analog 1. The main peak of analog 5 (undigested compound) was estimated to be human PTH (1-34) +48 Da=(Met 18+16 Da)+(Trp 23+32 Da). In other words, analog 5 was estimated to be human PTH (1-34)-Met 18 [O]-Trp 23 [dioxidation].

<Analog 6>

The analog showing a retention time=0.51 in the column "Analogs (undigested compounds)" in Table 8 was taken as analog 6, and Table 22 shows the results of mass measurement in LC/MS/MS of analog 6 (digested compound). Changes in mass of +16 Da in T2 and +4 Da in T3 were confirmed in analog 6 (digested compound) by comparison with the measured values of the relevant fragments in the standard solution (digested compound). T1 fragments in which there was no change in mass were also confirmed.

TABLE 22

Results of mass measurement of analog 6 (digested compound)

| Retention time (min) | Analog 5 [sic] Mass (mono.) | Standard solution Frag. No. | Standard solution Mass (mono.) | Difference in mass (F = 0, 4/5) |
|---|---|---|---|---|
| 9.589 | 901.4699 | T2 | 885.4984 | +16 Da |
| 18.332 | 871.4912 | T6 | 871.5030 | 0 |
| 18.332 | 999.5869 | T5-6 | 999.6100 | 0 |
| 19.032 | 705.4321 | T3 | 701.4508 | +4 Da |
| 22.583 | 1454.8536 | T1 | 1454.8715 | 0 |

Changes in mass of +16 Da in Met 18 in T2 and +4 Da in Trp 23 in T3 were confirmed, in the same way as in analog 1, as a result of MS/MS analysis of fragments confirmed to have changes in mass. Table 23 shows the results of comparing the mass of analog 6 (undigested compound) obtained by LC/MS with the calculated mass of 4115.1309 of human PTH (1-34). In analog 6 (undigested compound), a peak of +20 Da was confirmed in comparison with the calculated mass.

TABLE 23

Results of mass measurement of analog 6 (undigested compound)

| Retention time (min) | Measured mass Mass (mono.) | Calculated mass Mass (mono.) | Difference in mass (F = 0, 4/5) |
|---|---|---|---|
| 22.580 | 4135.6585 | 4115.1309 | +21 Da (+20 Da) |

Based on the results of MS/MS analysis, analog 6 was estimated to be human PTH (1-34) +20 Da=(Met 18+16 Da)+(Trp 23+4 Da). In other words, analog 6 was estimated to be human PTH (1-34)-Met 18 [O]-Trp 23 [dioxidation-formic acid elimination].

<Analog 7>

The analog showing a retention time=0.55 in the column "Analogs (undigested compounds)" in Table 8 was taken as analog 7, and Table 24 shows the results of mass measurement in LC/MS/MS of analog 7 (digested compound). A change in mass of +16 Da in T1 was confirmed in analog 7 (digested compound) by comparison with the measured values of the relevant fragments in the standard solution (digested compound).

TABLE 24

Results of mass measurement of analog 7 (digested compound)

| Retention time (min) | Analog 6 [sic] Mass (mono.) | Standard solution Frag. No. | Standard solution Mass (mono.) | Difference in mass (F = 0, 4/5) |
|---|---|---|---|---|
| 13.405 | 855.4859 | T2 | 885.4984 | 0 |
| 18.374 | 871.4885 | T6 | 871.5030 | 0 |
| 18.374 | 999.5920 | T5-6 | 999.6100 | 0 |
| 19.296 | 1470.8591 | T1 | 1454.8715 | +16 Da |
| 21.225 | 701.4354 | T3 | 701.4508 | 0 |

A change in mass of +16 Da in Met 8 in T1 was confirmed, in the same way as in analog 1, as a result of MS/MS analysis of fragments confirmed to have changes in mass. Table 25 shows the results of comparing the mass of analog 7 (undigested compound) obtained by LC/MS with the calculated mass of 4115.1309 of human PTH (1-34). In analog 7 (undigested compound), a peak of +16 Da was confirmed in comparison with the calculated mass.

TABLE 25

Results of mass measurement of analog 7 (undigested compound)

| Retention time (min) | Measured mass Mass (mono.) | Calculated mass Mass (mono.) | Difference in mass (F = 0, 4/5) |
|---|---|---|---|
| 22.353 | 4131.7101 | 4115.1309 | +17 Da (+16 Da) |

Based on the results of MS/MS analysis, analog 7 was estimated to be human PTH (1-34) +16 Da=(Met 8+16 Da). In other words, analog 7 was estimated to be human PTH (1-34)-Met 8 [O].

<Analog 8>

The analog showing a retention time=0.62 in the column "Analogs (undigested compounds)" in Table 8 was taken as analog 8, and Table 26 shows the results of mass measurement in LC/MS/MS of analog 8 (digested compound). A change in mass of +16 Da in T2 was confirmed in analog 8 (digested compound) by comparison with the measured values of the relevant fragments in the standard solution (digested compound).

TABLE 26

Results of mass measurement of analog 8 (digested compound)

| Retention time (min) | Analog 7 [sic] Mass (mono.) | Standard solution Frag. No. | Standard solution Mass (mono.) | Difference in mass (F = 0, 4/5) |
|---|---|---|---|---|
| 9.709 | 901.4782 | T2 | 885.4984 | +16 Da |
| 18.356 | 871.4903 | T6 | 871.5030 | 0 |
| 18.356 | 999.5916 | T5-6 | 999.6100 | 0 |

TABLE 26-continued

Results of mass measurement of analog 8 (digested compound)

| Retention time (min) | Analog 7 [sic] Mass (mono.) | Standard solution | | Difference in mass (F = 0, 4/5) |
|---|---|---|---|---|
| | | Frag. No. | Mass (mono.) | |
| 21.228 | 701.4383 | T3 | 701.4508 | 0 |
| 22.636 | 1454.8592 | T1 | 1454.8715 | 0 |

Figure 13:
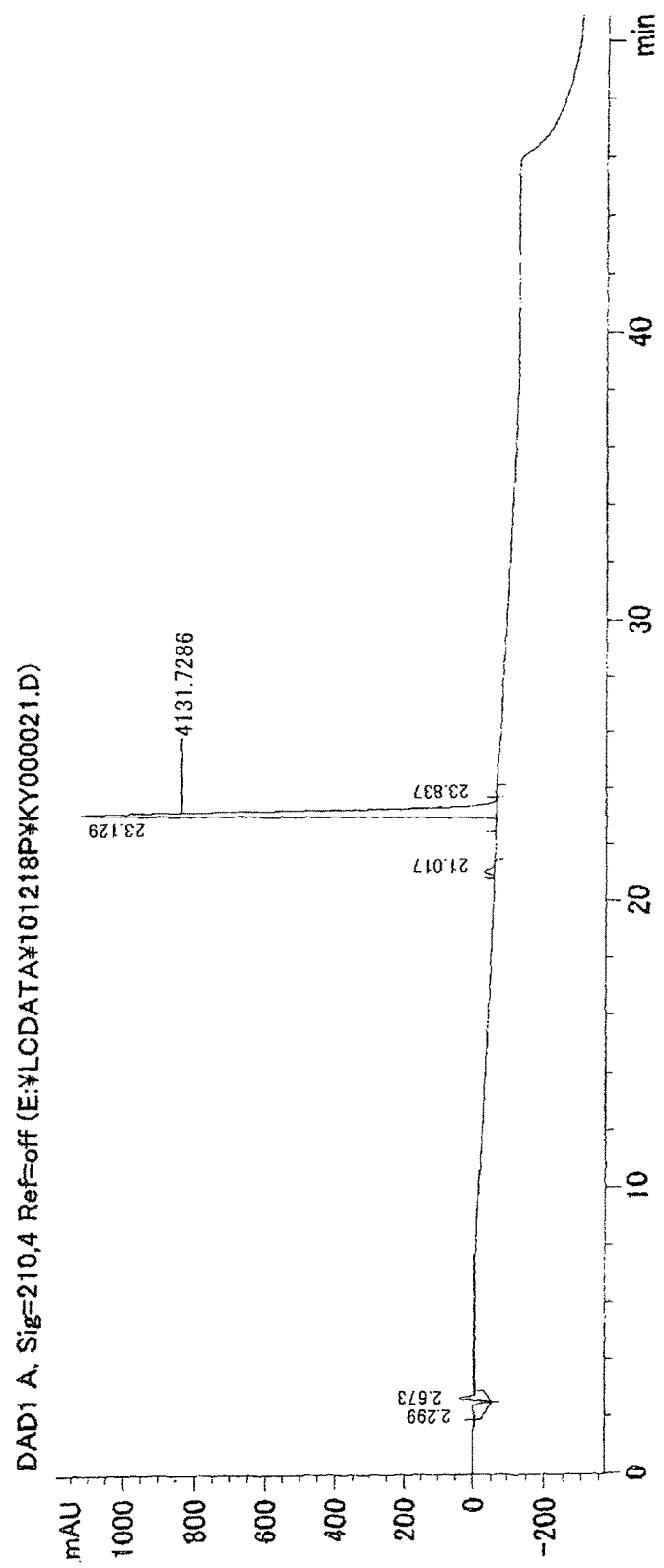
FIG. 13 shows the results of high-performance liquid chromatography-mass spectrometry (LC/MS) of analog 8. The horizontal axis represents the time (min), and the vertical axis represents the detection intensity.

A change in mass of +16 Da in Met 18 in T2 was confirmed, in the same way as in analog 1, as a result of MS/MS analysis of fragments confirmed to have changes in mass. Table 27 shows the results of comparing the mass of analog 8 (undigested compound) obtained by LC/MS with the calculated mass of 4115.1309 of human PTH (1-34). In analog 8 (undigested compound), a peak of +16 Da was confirmed in comparison with the calculated mass, as shown in FIG. 13.

TABLE 27

Results of mass measurement of analog 8 (undigested compound)

| Retention time (min) | Measured mass Mass (mono.) | Calculated mass Mass (mono.) | Difference in mass (F = 0, 4/5) |
|---|---|---|---|
| 23.129 | 4131.7286 | 4115.1309 | +17 Da (+16 Da) |

Based on the results of MS/MS analysis, analog 8 was estimated to be human PTH (1-34) +16 Da=(Met 18+16 Da). In other words, analog 8 was estimated to be human PTH (1-34)-Met 18 [O].

<Analog 9>

The analog showing a retention time=0.65 in the column "Analogs (undigested compounds)" in Table 8 was taken as analog 9, and Table 28 shows the results of mass measurement in LC/MS/MS of analog 9 (digested compound). A change in mass of +4 Da in T3 was confirmed in analog 9 (digested compound) by comparison with the measured values of the relevant fragments in the standard solution (digested compound).

TABLE 28

Results of mass measurement of analog 9 (digested compound)

| Retention time (min) | Analog 8[sic] Mass (mono.) | Standard solution | | Difference in mass (F = 0, 4/5) |
|---|---|---|---|---|
| | | Frag. No. | Mass (mono.) | |
| 13.392 | 885.4876 | T2 | 885.4984 | 0 |
| 18.329 | 871.4896 | T6 | 871.5030 | 0 |
| 18.329 | 999.5977 | T5-6 | 999.6100 | 0 |
| 19.023 | 705.4405 | T3 | 701.4508 | +4 Da |
| 22.567 | 1454.8638 | T1 | 1454.8715 | 0 |

A change in mass of +4 Da in Trp 23 in T3 was confirmed, in the same way as in analog 1, as a result of MS/MS analysis of fragments confirmed to have changes in mass.

Figure 14:
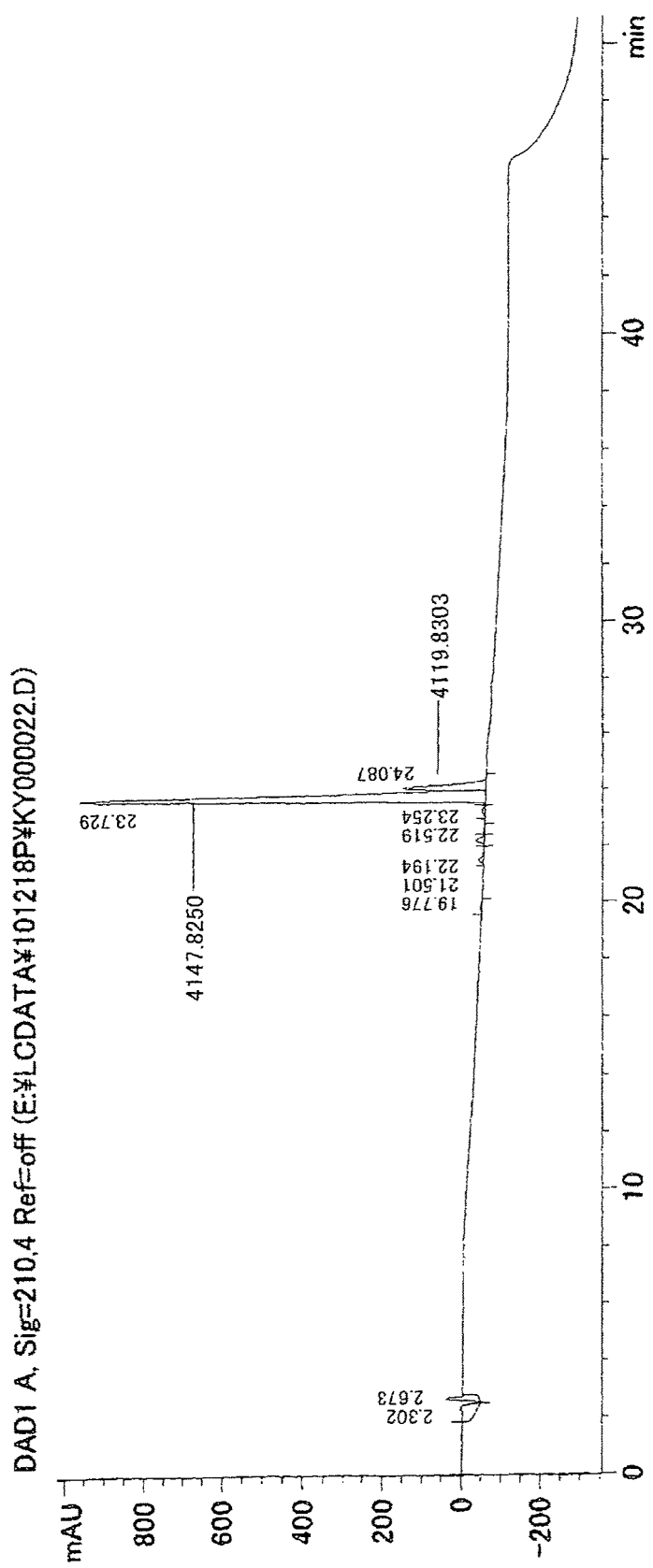
FIG. 14 shows the results of high-performance liquid chromatography-mass spectrometry (LC/MS) of analog 9. The horizontal axis represents the time (min), and the vertical axis represents the detection intensity.

Table 29 shows the results of comparing the mass of analog 9 (undigested compound) obtained by LC/MS with the calculated mass of 4115.1309 of human PTH (1-34). In analog 9 (undigested compound), peaks of +32 Da and +4 Da were confirmed in comparison with the calculated mass, and +32 Da appeared to be the main peak based on the size of the peaks, as shown in FIG. 14.

TABLE 29

Results of mass measurement of analog 9 (undigested compound)

| Retention time (min) | Measured mass Mass (mono.) | Calculated mass Mass (mono.) | Difference in mass (F = 0, 4/5) |
|---|---|---|---|
| 23.729 | 4147.8250 | 4115.1309 | +33 Da (+32 Da) |
| 24.087 | 4119.8303 | 4115.1309 | +5 Da (+4 Da) |

Based on the results of MS/MS analysis, it was estimated that human PTH (1-34) +4 Da=(Trp 23+4 Da). Trp 23 was assumed to have undergone a change of a) to b) in the course of trypsin digestion and other such procedures, in the same way as analog 1. The main peak of analog 9 (undigested compound) was estimated to be human PTH (1-34) +32 Da=(Trp 23+32 Da). In other words, analog 9 was estimated to be human PTH (1-34)-Trp 23 [dioxidation].

<Analogs 10 and 11>

The peak showing a retention time=0.70 in the column "Analogs (undigested compounds)" in Table 8 was derived from a mixture of analogs 10 and 11, as explained below. Table 30 shows the results of mass measurement in LC/MS/MS of a mixture of analogs 10 and 11 (digested compound). Changes in mass of +16 Da and +4 Da in T3 were confirmed as separate fragments in the mixture of analogs 10 and 11 (digested compound) by comparison with the measured values of the relevant fragments in the standard solution (digested compound).

TABLE 30

Results of mass measurement of a mixture of analogs 10 and 11 (digested compound)

| Retention time (min) | Analog 9 [sic] Mass (mono.) | Standard solution | | Difference in mass (F = 0, 4/5) |
|---|---|---|---|---|
| | | Frag. No. | Mass (mono.) | |
| 13.449 | 885.4893 | T2 | 885.4984 | 0 |
| 18.337 | 871.4925 | T6 | 871.5030 | 0 |
| 18.337 | 999.5985 | T5-6 | 999.6100 | 0 |
| 18.821 | 717.4391 | T3 | 701.4508 | +16 Da |
| 19.032 | 705.4407 | T3 | 701.4508 | +4 Da |
| 22.563 | 1454.8634 | T1 | 1454.8715 | 0 |

Table 31 shows the results obtained by MS/MS analysis of fragments confirmed to have changes in mass. A change in mass of +16 Da in Trp 23 in one T3 was confirmed as a result of comparison with the standard solution (digested compound). The structure of the changed form of +16 Da in Trp was expected to be c) in FIG. 6. Although data that made it possible to specify the amino acids changed in the other T3 could not be obtained, a change in mass of +4 Da in Trp 23 was estimated from the results of analysis of analogs 1-8.

TABLE 31

Results of MS/MS analysis of a mixture of analogs 10 and 11 (digested compound)

| Fragment No. | Mass observed on MS/MS spectrum | | Estimated structure | Amino acid with change in mass |
|---|---|---|---|---|
| | Analog 9 [sic] (mono.) | Standard solution (mono.) | | |
| T3 | 271.2131 | 271.2085 | PTH (24-25) | Trp 23 +16 Da |
| | 490.3079 | — | PTH (23-25) +16 Da | |
| | — | 474.3203 | PTH (23-25) | |

Figure 15:
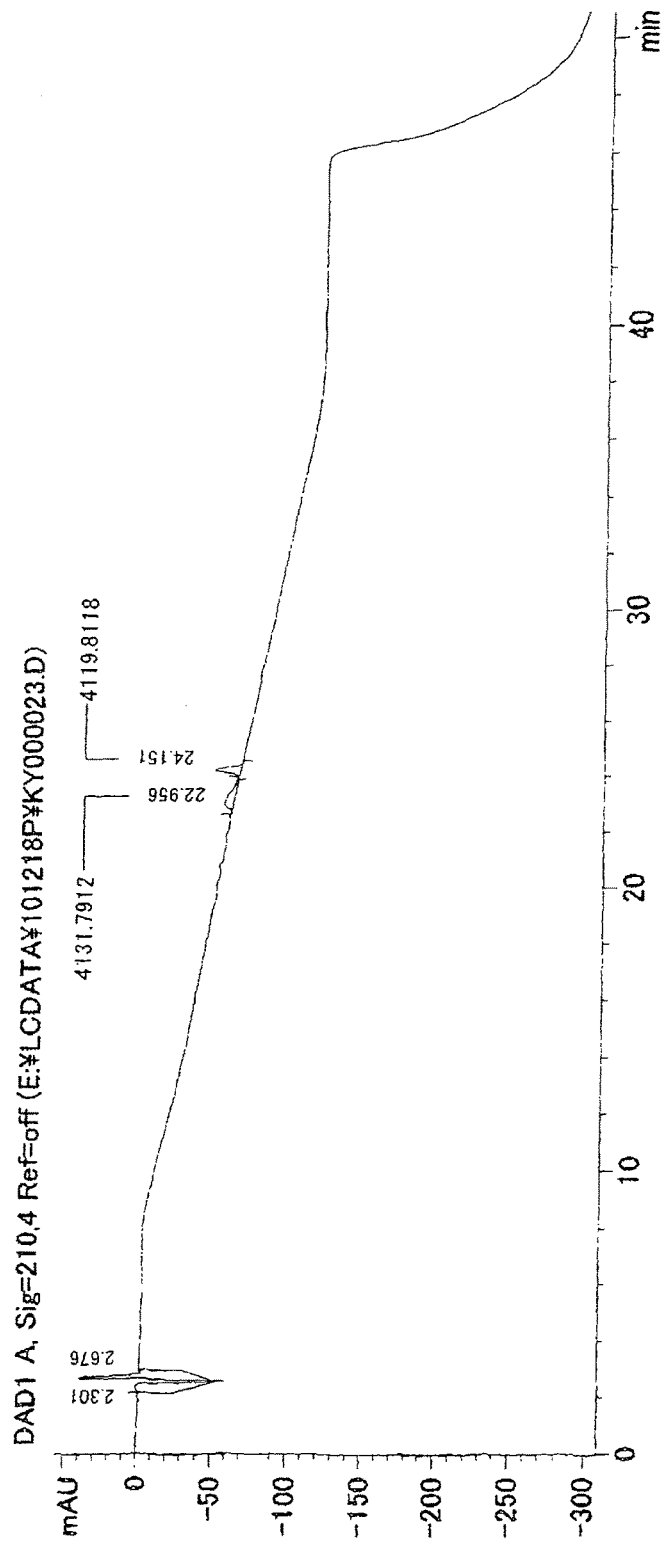
FIG. 15 shows the results of high-performance liquid chromatography-mass spectrometry (LC/MS) of a mixture of analogs 10 and 11. The horizontal axis represents the time (min), and the vertical axis represents the detection intensity.

Table 32 shows the results of comparing the mass of a mixture of analogs 10 and 11 (undigested compound) obtained by LC/MS with the calculated mass of 4115.1309 of human PTH (1-34). In the mixture of analogs 10 and 11 (undigested compound), peaks of +16 Da and +4 Da were observed comparison to the calculated masses, as shown in FIG. 15.

TABLE 32

Results of mass measurement of a mixture of analogs 10 and 11 (undigested compound)

| Retention time (min) | Measured mass Mass (mono.) | Calculated mass Mass (mono.) | Difference in mass (F = 0, 4/5) |
|---|---|---|---|
| 22.956 | 4131.7912 | 4115.1309 | +17 Da (+16 Da) |
| 24.151 | 4119.8118 | 4115.1309 | +5 Da (+4 Da) |

Based on the results of MS/MS analysis, these were attributed as human PTH (1-34) +16 Da=(Trp 23+16 Da) and human PTH (1-34) +4 Da=(Trp 23+4 Da), and the peak showing a retention time=0.70 in the column "Analogs (undigested compounds)" in Table 8 was estimated to be a mixture of analogs 10 and 11. In other words, analog 10 was estimated to be human PTH (1-34)-Trp 23 [monoxidation], and analog 11 was estimated to be human PTH (1-34)-Trp 23 [dioxidation-formic acid elimination].

<Summary of Structural Analysis>

Figure 5:
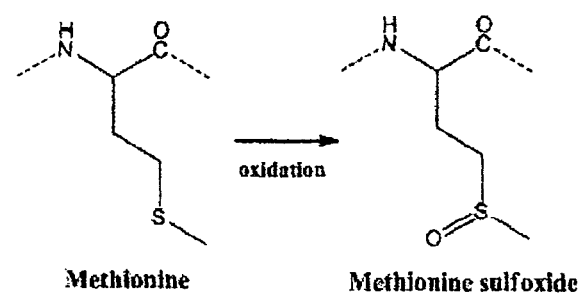
FIG. 5 shows the structure of a methionine oxide compound.
Figure 6:
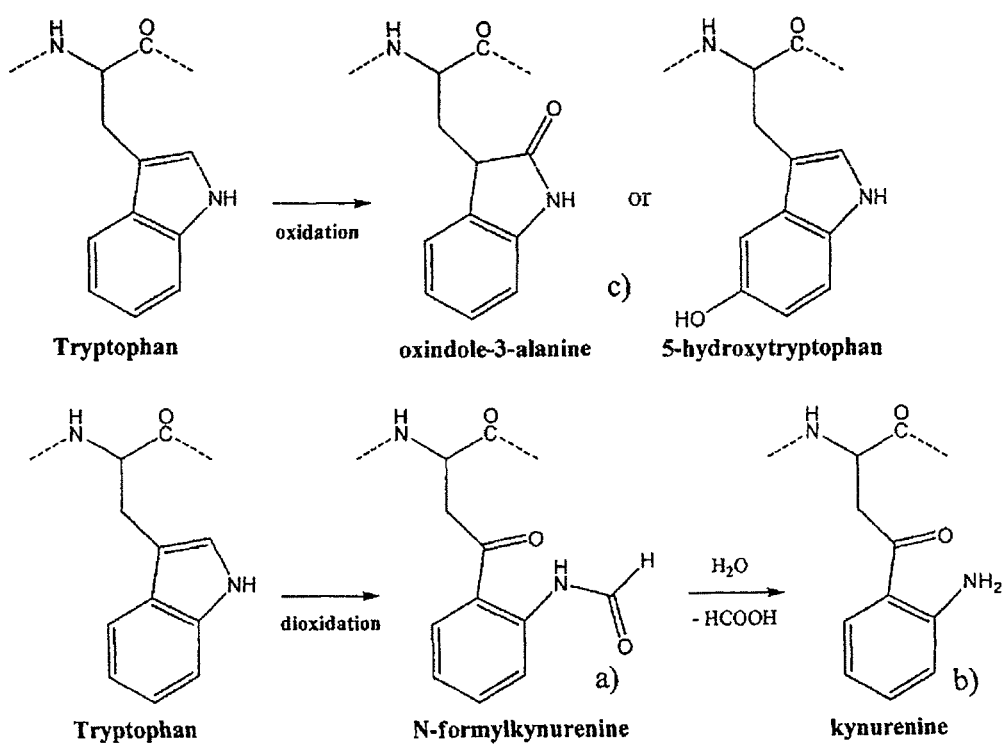
FIG. 6 shows the structure of a tryptophan variant.

Table 33 shows the relative retention time and estimated structure results of each analog. FIG. 5 shows the oxidation of the methionine residues in the table, and FIG. 6 shows a), b), and c) in the table. The relative retention time of each analog in the table shows the relative retention time taking the retention time of human PTH (1-34) as 1.

TABLE 33

Relative retention time and estimated structure of each analog

| No. | Relative retention time | Summary of change | | | Name of analog |
|---|---|---|---|---|---|
| | | Amino acid changed | Change in mass | Nature of change | |
| (1) | 0.42 | Met 8 | 16 Da | Oxidation | Human PTH (1-34)-Met 8 [O]- |
| | | Met 18 | 16 Da | Oxidation | Met 18 [O]-Trp 23 |
| | | Trp 23 | 32 Da | a) | [dioxidation] |
| (2) | 0.43 | Met 8 | 16 Da | Oxidation | Human PTH (1-34)-Met 8 [O]- |
| | | Met 18 | 16 Da | Oxidation | Met 18 [O]-Trp 23 |
| | | Trp 23 | 4 Da | b) | [dioxidation-formic acid elimination] |
| (3) | 0.46 | Met 8 | 16 Da | Oxidation | Mixture containing human |
| | | Met 18 | 16 Da | Oxidation | PTH (1-34)-Met 8 [O]-Met 18 |
| | 0.46 | Met 8 | 16 Da | Oxidation | [O] and |
| | | Trp 23 | 32 Da | a) | human PTH (1-34)-Met 8 [O]-Trp 23 [dioxidation] |
| (4) | 0.49 | Met 18 | 16 Da | Oxidation | Human PTH (1-34)-Met 18 |
| | | Trp 23 | 32 Da | a) | [O]-Trp 23 [dioxidation] |
| (5) | 0.51 | Met 18 | 16 Da | Oxidation | Human PTH (1-34)-Met 18 |
| | | Trp 23 | 4 Da | b) | [O]-Trp 23 [dioxidation-formic acid elimination] |
| (6) | 0.55 | Met 8 | 16 Da | Oxidation | Human PTH (1-34)-Met 8 [O] |
| (7) | 0.62 | Met 18 | 16 Da | Oxidation | Human PTH (1-34)-Met 18 [O] |
| (8) | 0.65 | Trp 23 | 32 Da | a) | Human PTH (1-34)-Trp 23 [dioxidation] |
| (9) | 0.7 | Trp 23 | 16 Da | c) | Mixture containing human |
| | 0.7 | Trp 23 | 4 Da | b) | PTH (1-34)-Trp 23 [monoxidation] and human PTH (1-34)-Trp 23 [dioxidation-formic acid elimination] |

INDUSTRIAL APPLICABILITY

Since a freeze-dried preparation containing high-purity PTH peptide is provided by the present invention, the present invention can be used in the pharmaceutical manufacturing industry.

EXPLANATION OF SYMBOLS

1: Large door
2: Small door
3: Sub-door (open)
4: Sub-door (closed)
5: Airflow-adjusting cover

The invention claimed is:

1. A method for producing a freeze-dried preparation containing human parathyroid hormone (PTH) (1-34) and one or more analogs thereof, wherein the method is conducted in a pharmaceutical production facility that is sterilized by a disinfectant, the method comprising:
preparing a solution containing the human PTH (1-34) and the one or more analogs thereof housed in one or more containers;
loading the one or more containers containing the human PTH (1-34) and the one or more analogs thereof into a freeze-drying apparatus while controlling exposure of the solution to air environments within a pharmaceutical production facility, wherein
the loading step comprises controlling inflow of air within the pharmaceutical production facility into the freeze-drying apparatus;
producing a freeze-dried preparation containing the human PTH (1-34) and the one or more analogs thereof; and
sealing the containers, wherein
(i) the freeze-drying apparatus comprises a freeze-drying chamber having an easily openable and closable sub-door provided in an opening created in a small door unit configured to be opened when the one or more containers are loaded into or are unloaded from the chamber, and the controlling the inflow of air within the pharmaceutical production facility into the freeze-drying apparatus comprises opening the sub-door only during the loading and quickly closing the sub-door after the loading, or
(ii) the freeze-drying apparatus comprises a freeze-drying chamber having an opening created in a small door unit configured to be opened when the one or more containers are loaded into or are unloaded from the chamber, and the controlling the inflow of air within the pharmaceutical production facility into the freeze-drying apparatus comprises directing air flow within the pharmaceutical production facility away from the opening to the inside of the chamber by means of an airflow-adjusting cover configured to alter the air flow away from the opening of the chamber thereby controlling the inflow of air within the pharmaceutical production facility into the freeze-drying apparatus.

2. The method of claim 1, wherein the one or more human PTH (1-34) analogs are selected from the group consisting of:
a) analog 1'
an oxide of the human PTH (1-34) in which residues corresponding to position 8 and position 18 methionine of the human PTH (1-34) are methionine sulfoxide residues and residue corresponding to a position 23 tryptophan is a residue of formula (a);
b) analog 2'
an oxide of the human PTH (1-34) in which the residues corresponding to the position 8 and position 18 methionine of the human PTH (1-34) are methionine sulfoxide residues and the residue corresponding to the position 23 tryptophan is a residue of formula (b);

c) analog 3'
an oxide of the human PTH (1-34) in which the residues corresponding to the position 8 and position 18 methionine of the human PTH (1-34) are methionine sulfoxide residues;

d) analog 4'
an oxide of the human PTH (1-34) in which the residue corresponding to the position 8 methionine of the human PTH (1-34) is a methionine sulfoxide residue and the residue corresponding to the position 23 tryptophan is the residue of formula (a);

e) analog 5'
an oxide of the human PTH (1-34) in which the residue corresponding to the position 18 methionine of the human PTH (1-34) is a methionine sulfoxide residue and the residue corresponding to the position 23 tryptophan is the residue of formula (a);

f) analog 6'
an oxide of the human PTH (1-34) in which the residue corresponding to the position 18 methionine of the human PTH (1-34) is a methionine sulfoxide residue and the residue corresponding to the position 23 tryptophan is the residue of formula (b);

g) analog 9'
an oxide of the human PTH (1-34) in which the residue corresponding to the position 23 tryptophan of the human PTH (1-34) is the residue of formula (a);

h) analog 10'
an oxide of the human PTH (1-34) in which the residue corresponding to the position 23 tryptophan of the human PTH (1-34) is a tryptophan monoxide residue of formula (c-1) or (c-2) below

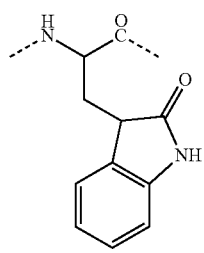

(c)-1

-continued (c)-2 i) analog 11'
   an oxide of the human PTH (1-34) in which the residue corresponding to the position 23 tryptophan of the human PTH (1-34) is the residue of formula (b);
j) analog 7'
   an oxide of the human PTH (1-34) in which the residue corresponding to the position 8 methionine of the human PTH (1-34) is a methionine sulfoxide residue; and
k) analog 8'
   an oxide of the human PTH (1-34) in which the residue corresponding to the position 18 methionine of the human PTH (1-34) is a methionine sulfoxide residue, wherein formula (a) is (a)

and formula (b) is (b)

3. The method of claim 2, wherein the one or more human PTH (1-34) analogs are: j) analog 7'; k) analog 8'; and one or more human PTH (1-34) analogs selected from the group consisting of a) analog 1', b) analog 2', c) analog 3', d) analog 4', e) analog 5', f) analog 6', g) analog 9', h) analog 10', and i) analog 11'.

4. The method of claim 2, wherein the freeze-dried preparation comprises the human PTH (1-34) j) analog 7', k) analog 8', and one or more human PTH (1-34) analogs selected from the group consisting of a) analog 1', b) analog 2', c) analog 3', d) analog 4', e) analog 5', f) analog 6', g) analog 9', h) analog 10', and i) analog 11', wherein the human PTH (1-34) is high-purity human PTH (1-34), wherein high-purity means that (i) an amount of each of the one or more human PTH (1-34) analogs versus the sum of an amount of the human PTH (1-34) and the total amount of the human PTH (1-34) analogs in the preparation is 1.0% or less, and (ii) the total amount of human PTH (1-34) analogs versus the sum of the amount of the human PTH (1-34) and the total amount of human PTH (1-34) analogs is 5.0% or less.

5. The method of claim 1, further comprising controlling exposure of the solution containing the human PTH (1-34) and the one or more analogs thereof to air environments within the pharmaceutical production after the step of freeze drying and during the step of sealing the containers.

6. The method of claim 1, wherein loading the one or more containers containing the human PTH (1-34) and the one or more analogs thereof into the freeze-drying apparatus is carried out for a period of time of three or more hours.

7. The method of claim 1, wherein an inside of the freeze-drying apparatus is purged with an inert gas.

8. The method of claim 7, wherein the inside of the freeze-drying apparatus is purged with the inert gas after loading the containers and prior to closing the sub-door.

9. The method of claim 7, wherein the inert gas is nitrogen.

10. The method of claim 1, wherein the containers are glass vials.

11. The method of claim 1, wherein the air environment within the pharmaceutical production facility is an air environment in which 1) the air is of grade A, 2) clean air that has passed through an HEPA filter configured to trap particles having a particle size of 0.3 μm at an efficiency of 99.97% or higher is maintained as a one-way air flow downward from above, and 3) the ozone concentration is 0.001-0.1 ppm.

12. The method of claim 1, wherein the air environment within the pharmaceutical production facility is an air environment containing a formaldehyde concentration of 0.1 ppm or less.

13. The method of claim 1, wherein (i) an amount of each of the one or more human PTH (1-34) analogs is 1.0% or less than the sum of an amount of the human PTH (1-34) and the total amount of the one or more human PTH (1-34) analogs, and (ii) the total amount of the one or more human PTH (1-34) analogs is 5.0% or less than a sum of the amount of the human PTH (1-34) and total amount of the one or more PTH (1-34) analogs in the freeze-dried preparation containing the human PTH (1-34).

14. A method for producing a freeze-dried preparation containing human parathyroid hormone (PTH) (1-34) and one or more analogs thereof, wherein the method is conducted in a pharmaceutical production facility that is sterilized by a disinfectant and comprises an air environment comprising substances having oxidizing capability, the method comprising:
   preparing a solution containing the human PTH (1-34) and one or more analogs thereof-housed in one or more containers;
   loading the one or more containers containing the human PTH (1-34) and one or more analogs thereof into a freeze-drying apparatus;
   producing a freeze-dried preparation containing the human PTH (1-34) and one or more analogs thereof; and
   sealing the containers; and wherein
the method further comprises controlling contact of the human PTH (1-34) and one or more analogs thereof with the substances having oxidizing capability in the air environments within the pharmaceutical production facility.

15. The method of claim 2, wherein the freeze-dried preparation in the sealed containers comprises one or more human PTH (1-34) analogs selected from the group consisting of analog 1', analog 2', analog 4', analog 5', analog 6', analog 9', analog 10', and analog 11', and
(i) an amount of each of the one or more human PTH (1-34) analogs versus the sum of an amount of the human PTH (1-34) and the total amount of the human PTH (1-34) analogs in the preparation is 1.0% or less, and
(ii) the total amount of human PTH (1-34) analogs versus the sum of the amount of the human PTH (1-34) and the total amount of human PTH (1-34) analogs is 5.0% or less.

16. The method of claim 14, wherein the one or more human PTH (1-34) analogs are selected from the group consisting of:
a) analog 1'
an oxide of the human PTH (1-34) in which residues corresponding to position 8 and position 18 methionine of the human PTH (1-34) are methionine sulfoxide residues and residue corresponding to a position 23 tryptophan is a residue of formula (a);
b) analog 2'
an oxide of the human PTH (1-34) in which the residues corresponding to the position 8 and position 18 methionine of the human PTH (1-34) are methionine sulfoxide residues and the residue corresponding to the position 23 tryptophan is a residue of formula (b);
c) analog 3'
an oxide of the human PTH (1-34) in which the residues corresponding to the position 8 and position 18 methionine of the human PTH (1-34) are methionine sulfoxide residues;
d) analog 4'
an oxide of the human PTH (1-34) in which the residue corresponding to the position 8 methionine of the human PTH (1-34) is a methionine sulfoxide residue and the residue corresponding to the position 23 tryptophan is the residue of formula (a);
e) analog 5'
an oxide of the human PTH (1-34) in which the residue corresponding to the position 18 methionine of the human PTH (1-34) is a methionine sulfoxide residue and the residue corresponding to the position 23 tryptophan is the residue of formula (a);
f) analog 6'
an oxide of the human PTH (1-34) in which the residue corresponding to the position 18 methionine of the human PTH (1-34) is a methionine sulfoxide residue and the residue corresponding to the position 23 tryptophan is the residue of formula (b);
g) analog 9'
an oxide of the human PTH (1-34) in which the residue corresponding to the position 23 tryptophan of the human PTH (1-34) is the residue of formula (a);
h) analog 10'
an oxide of the human PTH (1-34) in which the residue corresponding to the position 23 tryptophan of the human PTH (1-34) is a tryptophan monoxide residue of formula (c-1) or (c-2) below

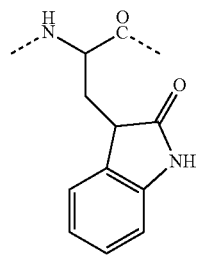

(c)-1

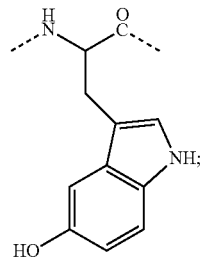

(c)-2 i) analog 11'
an oxide of the human PTH (1-34) in which the residue corresponding to the position 23 tryptophan of the human PTH (1-34) is the residue of formula (b);
j) analog 7'
an oxide of the human PTH (1-34) in which the residue corresponding to the position 8 methionine of the human PTH (1-34) is a methionine sulfoxide residue; and
k) analog 8'
an oxide of the human PTH (1-34) in which the residue corresponding to the position 18 methionine of the human PTH (1-34) is a methionine sulfoxide residue, wherein formula (a) is

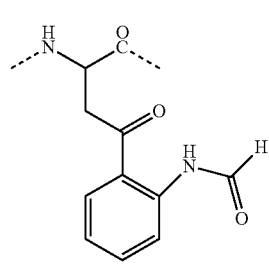

(a)

and formula (b) is

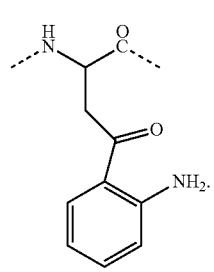

(b)

17. The method of claim 16, wherein the one or more human PTH (1-34) analogs are: j) analog 7'; k) analog 8'; and one or more human PTH (1-34) analogs selected from the group consisting of a) analog 1', b) analog 2', c) analog 3', d) analog 4', e) analog 5', f) analog 6', g) analog 9', h) analog 10', and i) analog 11'.

18. The method of claim 16, wherein the freeze-dried preparation comprises the human PTH (1-34) j) analog 7', k) analog 8', and one or more human PTH (1-34) analogs selected from the group consisting of a) analog 1', b) analog 2', c) analog 3', d) analog 4', e) analog 5', f) analog 6', g) analog 9', h) analog 10', and i) analog 11', wherein the human PTH (1-34) is high-purity human PTH (1-34), wherein high-purity means that (i) an amount of each of the one or more human PTH (1-34) analogs versus the sum of an amount of the human PTH (1-34) and the total amount of the human PTH (1-34) analogs in the preparation is 1.0% or less, and (ii) the total amount of human PTH (1-34) analogs versus the sum of the amount of the human PTH (1-34) and the total amount of human PTH (1-34) analogs is 5.0% or less.

19. The method of claim 14, further comprising controlling exposure of the solution containing the human PTH (1-34) and the one or more analogs thereof to air environments within the pharmaceutical production after the step of producing a freeze-dried preparation and during the step of sealing the containers.

20. The method of claim 14, wherein the loading step comprises controlling inflow of air within the pharmaceutical production facility into the freeze-drying apparatus.

21. The method of claim 14, wherein loading the one or more containers containing the human PTH (1-34) and the one or more analogs thereof into the freeze-drying apparatus is carried out for a period of time of three or more hours.

22. The method of claim 20, wherein the freeze-drying apparatus comprises a freeze-drying chamber having an easily openable and closable sub-door provided in an opening created in a small door unit configured to be opened when the one or more containers are loaded into or are unloaded from the chamber, and the controlling the inflow of air within the pharmaceutical production facility into the freeze-drying apparatus comprises opening the sub-door only during the loading and quickly closing the sub-door after the loading.

23. The method of claim 20, wherein the freeze-drying apparatus comprises a freeze-drying chamber having an opening created in a small door unit configured to be opened when the one or more containers are loaded into or are unloaded from the chamber, and the controlling the inflow of air within the pharmaceutical production facility into the freeze-drying apparatus comprises directing air flow within the pharmaceutical production facility away from the opening to the inside of the chamber by means of an airflow-adjusting cover configured to alter the air flow away from the opening of the chamber thereby controlling the inflow of air within the pharmaceutical production facility into the freeze-drying apparatus.

24. The method of claim 14, wherein an inside of the freeze-drying apparatus is purged with an inert gas.

25. The method of claim 22, wherein the inside of the freeze-drying apparatus is purged with the inert gas after loading the containers and prior to closing the sub-door.

26. The method of claim 24, wherein the inert gas is nitrogen.

27. The method of claim 14, wherein the containers are glass vials.

28. The method of claim 14, wherein the air environment within the pharmaceutical production facility is an air environment in which 1) the air is of grade A, 2) clean air that has passed through an HEPA filter configured to trap particles having a particle size of 0.3 µm at an efficiency of 99.97% or higher is maintained as a one-way air flow downward from above, and 3) the ozone concentration is 0.001-0.1 ppm.

29. The method of claim 14, wherein the air environment within the pharmaceutical production facility is an air environment containing a formaldehyde concentration of 0.1 ppm or less.

30. The method of claim 14, wherein (i) an amount of each of the one or more human PTH (1-34) analogs is 1.0% or less than the sum of an amount of the human PTH (1-34) and the total amount of the one or more human PTH (1-34) analogs, and (ii) the total amount of the one or more human PTH (1-34) analogs is 5.0% or less than a sum of the amount of the human PTH (1-34) and total amount of the one or more PTH (1-34) analogs in the freeze-dried preparation containing the human PTH (1-34).

31. A method for producing a freeze-dried preparation containing human parathyroid hormone (PTH)(1-34) and one or more analogs thereof, wherein the method is conducted in a pharmaceutical production facility that is sterilized by a disinfectant, the method comprising:
preparing a solution containing the human PTH (1-34) and the one or more analogs thereof housed in one or more containers;
loading the one or more containers containing the human PTH (1-34) and the one or more analogs thereof into a freeze-drying apparatus while controlling exposure of the solution to air environments within a pharmaceutical production facility;
producing a freeze-dried preparation containing the human PTH (1-34) and the one or more analogs thereof; and
sealing the containers,
wherein the one or more human PTH (1-34) analogs are selected from the group consisting of:
a) analog 1'
an oxide of the human PTH (1-34) in which residues corresponding to position 8 and position 18 methionine of the human PTH (1-34) are methionine sulfoxide residues and residue corresponding to a position 23 tryptophan is a residue of formula (a);
b) analog 2'
an oxide of the human PTH (1-34) in which the residues corresponding to the position 8 and position 18 methionine of the human PTH (1-34) are methionine sulfoxide residues and the residue corresponding to the position 23 tryptophan is a residue of formula (b);
c) analog 4'
an oxide of the human PTH (1-34) in which the residue corresponding to the position 8 methionine of the human PTH (1-34) is a methionine sulfoxide residue and the residue corresponding to the position 23 tryptophan is the residue of formula (a);
d) analog 5'
an oxide of the human PTH (1-34) in which the residue corresponding to the position 18 methionine of the human PTH (1-34) is a methionine sulfoxide residue and the residue corresponding to the position 23 tryptophan is the residue of formula (a);
e) analog 6'
an oxide of the human PTH (1-34) in which the residue corresponding to the position 18 methionine of the human PTH (1-34) is a methionine sulfoxide residue and the residue corresponding to the position 23 tryptophan is the residue of formula (b);

f) analog 9' an oxide of the human PTH (1-34) in which the residue corresponding to the position 23 tryptophan of the human PTH (1-34) is the residue of formula (a);

g) analog 10' an oxide of the human PTH (1-34) in which the residue corresponding to the position 23 tryptophan of the human PTH (1-34) is a tryptophan monoxide residue of formula (c-1) or (c-2) below

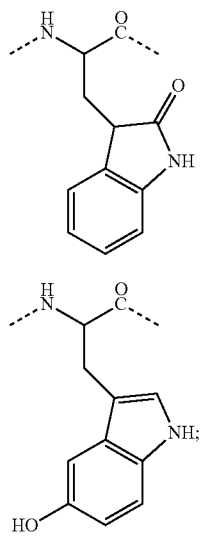

and h) analog 11' an oxide of the human PTH (1-34) in which the residue corresponding to the position 23 tryptophan of the human PTH (1-34) is the residue of formula (b);

wherein formula (a) is

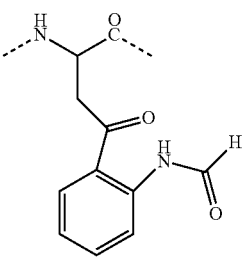

and formula (b) is

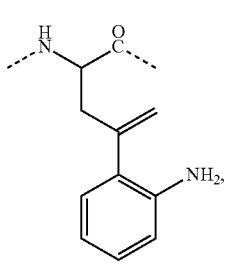

and (i) an amount of each of the one or more human PTH (1-34) analogs versus the sum of an amount of the human PTH (1-34) and the total amount of the human PTH (1-34) analogs in the preparation is 1.0% or less, and (ii) the total amount of human PTH (1-34) analogs versus the sum of the amount of the human PTH (1-34) and the total amount of human PTH (1-34) analogs is 5.0% or less.

* * * * *